United States Patent
Ye et al.

(10) Patent No.: US 8,729,084 B2
(45) Date of Patent: May 20, 2014

(54) BENZOFURANYL ANALOGUES AS GPR119 MODULATORS

(75) Inventors: Xiang-Yang Ye, Princeton, NJ (US); Dean A. Wacker, Yardley, PA (US); Jeffrey A. Robl, Newtown, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/696,131

(22) PCT Filed: May 4, 2011

(86) PCT No.: PCT/US2011/035087
§ 371 (c)(1),
(2), (4) Date: Nov. 5, 2012

(87) PCT Pub. No.: WO2011/140161
PCT Pub. Date: Nov. 10, 2011

(65) Prior Publication Data
US 2013/0059858 A1    Mar. 7, 2013

Related U.S. Application Data

(60) Provisional application No. 61/331,852, filed on May 6, 2010.

(51) Int. Cl.
*C07D 405/14*    (2006.01)
*A61K 31/506*    (2006.01)

(52) U.S. Cl.
USPC ...... 514/252.18; 514/275; 514/318; 544/295; 544/331; 544/332; 546/193

(58) Field of Classification Search
USPC .......................... 544/295, 331, 332; 546/193; 514/252.18, 275, 318
See application file for complete search history.

(56) References Cited

U.S. PATENT DOCUMENTS

| | | |
|---|---|---|
| 6,531,503 B1 | 3/2003 | Bathe et al. |
| 7,452,911 B2 | 11/2008 | Stenkamp et al. |
| 2009/0069282 A1 | 3/2009 | Stenkamp et al. |

FOREIGN PATENT DOCUMENTS

| | | |
|---|---|---|
| WO | WO 2006/044133 | 4/2006 |
| WO | WO 2007/003961 | 1/2007 |
| WO | WO 2009/127321 | 10/2009 |

OTHER PUBLICATIONS

Overton et al., GPR119, a novel G protein-coupled receptor target for the treatment of type 2 diabetes and obesity, British Journal of Pharmacology (2008) 153, pp. S76-S81.*
Damasio, Alzheimer's Disease and Related Dementias, Cecil Textbook of Medicine, 20th Edition, vol. 2, pp. 1992-1996, 1996.*
Layzer, Degenerative Diseases of the Nervous System, Cecil Textbook of Medicine, 20th Edition, vol. 2, pp. 2050-2057, 1996.*
Jones, R.M. et al., "GPR119 agonists for the treatment of type 2 diabetes", Expert Opin. Ther. Patents, vol. 19, No. 10, pp. 1339-1359 (2009).
Wu, Y et al., "2,5-Disubstituted pyridines as potent GPR119 agonists", Bioorganic & Medicinal Chemistry Letters, vol. 20, pp. 2577-2581 (2010).

* cited by examiner

*Primary Examiner* — Deepak Rao

(57) ABSTRACT

Novel compounds of structure Formula I: or an enantiomer, diastereomer, tautomer, prodrug or salt thereof, wherein A, L, m, n, o, p, $R_2$, $R_3$, $R_3$, $R_4$ and $R_5$ are defined herein, are provided which are GPR119 G protein-coupled receptor modulators. GPR119 G protein-coupled receptor modulators are useful in treating, preventing, or slowing the progression of diseases requiring GPR119 G protein-coupled receptor modulator therapy. Thus, the disclosure also concerns compositions comprising these novel compounds and methods of treating diseases or conditions related to the activity of the GPR119 G protein-coupled receptor by using any of these novel compounds or a composition comprising any of such novel compounds.

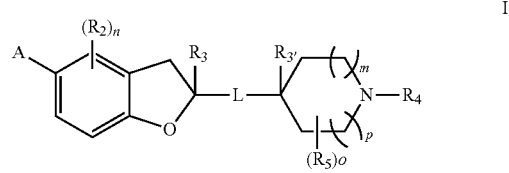

15 Claims, No Drawings

BENZOFURANYL ANALOGUES AS GPR119 MODULATORS

CROSS REFERENCES TO RELATED APPLICATIONS

This application claims the benefit of International Application No. PCT/US2011/035087, filed May 4, 2011, which claims benefit of U.S. Provisional Application Ser. No. 61/331,852, filed on May 6, 2010, The entire teachings of the referenced applications are herein incorporated by reference in their entirety.

FIELD OF THE INVENTION

The present invention provides novel benzofuranyl compounds, and analogues, which are modulators of the GPR119 G protein-coupled receptor, compositions containing them, and methods of using them, for example, for the prevention and/or treatment of diseases or disorders associated with the activity of the GPR119 G protein-coupled receptor, e.g., diabetes and obesity.

BACKGROUND OF THE INVENTION

Diabetes mellitus is a serious disease afflicting over 100 million people worldwide. In the United States, there are more than 12 million diabetics, with 600,000 new cases diagnosed each year. Diabetes mellitus is a diagnostic term for a group of disorders characterized by abnormal glucose homeostasis resulting in elevated blood sugar. There are many types of diabetes, but the two most common are Type 1 (also referred to as insulin-dependent diabetes mellitus or IDDM) and Type 2 (also referred to as non-insulin-dependent diabetes mellitus or NIDDM).

The etiology of the different types of diabetes is not the same; however, everyone with diabetes has two things in common: overproduction of glucose by the liver and little or no ability to move glucose out of the blood into the cells where it becomes the body's primary fuel.

People who do not have diabetes rely on insulin, a hormone made in the pancreas, to move glucose from the blood into the cells of the body. However, people who have diabetes either do not produce insulin or cannot efficiently use the insulin they produce; therefore, they cannot move glucose efficiently into their cells. Glucose accumulates in the blood creating a condition called hyperglycemia, and over time, can cause serious health problems.

Diabetes is a syndrome with interrelated metabolic, vascular, and neuropathic components. The metabolic syndrome, generally characterized by hyperglycemia, comprises alterations in carbohydrate, fat and protein metabolism caused by absent or markedly reduced insulin secretion and/or ineffective insulin action. The vascular syndrome consists of abnormalities in the blood vessels leading to cardiovascular, retinal and renal complications. Abnormalities in the peripheral and autonomic nervous systems are also part of the diabetic syndrome.

Diabetes has also been implicated in the development of kidney disease, eye diseases and nervous-system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

Many people with NIDDM have sedentary lifestyles and are obese; they weigh approximately 20% more than the recommended weight for their height and build. Furthermore, obesity is characterized by hyperinsulinemia and insulin resistance, a feature shared with NIDDM, hypertension and atherosclerosis.

Obesity, which is the result of an imbalance between caloric intake and energy expenditure, is highly correlated with insulin resistance and diabetes in experimental animals and human. However, the molecular mechanisms that are involved in obesity-diabetes syndromes are not clear. During early development of obesity, increased insulin secretion balances insulin resistance and protects patients from hyperglycemia (Le Stunff et al., *Diabetes,* 43:696-702 (1989)). However, over time, β-cell function deteriorates and non-insulin-dependent diabetes develops in about 20% of the obese population (Pederson, P., *Diab. Metab. Rev.,* 5:505-509 (1989)) and (Brancati, F. L. et al., *Arch. Intern. Med.,* 159:957-963 (1999)). Given its high prevalence in modern societies, obesity has thus become the leading risk factor for NIDDM (Hill, J. O. et al., *Science,* 280:1371-1374 (1998)). However, the factors which predispose a fraction of patients to alteration of insulin secretion in response to fat accumulation remain unknown. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Obesity considerably increases the risk of developing cardiovascular diseases as well. Coronary insufficiency, atheromatous disease, and cardiac insufficiency are at the forefront of the cardiovascular complication induced by obesity. It is estimated that if the entire population had an ideal weight, the risk of coronary insufficiency would decrease by 25% and the risk of cardiac insufficiency and of cerebral vascular accidents by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for NIDDM, obesity and coronary heart disease as well as the potential value of an integrated approach involving the treatment of both obesity and diabetes (Perry, I. J. et al., *BMJ,* 310:560-564 (1995)).

Type 2 diabetes results from the progressive loss of pancreatic β-cell function in the presence of insulin resistance, leading to an overall reduction in insulin output (Prentki, M. et al., "Islet failure in type 2 diabetes", *J. Clin. Invest.,* 116:1802-1812 (2006)). β-cells are the cell type that store and release insulin in response to an elevation in plasma glucose or in response to hormonal signals from the gut following the ingestion of food. Evidence suggests that in type 2 diabetics the rate of β-cell cell death (apoptosis) exceeds that of new β-cell development, yielding an overall loss in β-cell number (Butler, A. E. et al., "β-cell deficit and increased β-cell apoptosis in humans with type 2 diabetes", *Diabetes,* 52:102-110 (2003)). β-cell apoptosis may arise from persistent elevations in plasma glucose levels (glucotoxicity) and/or plasma lipid levels (lipotoxicity).

G-protein coupled receptors (GPCRs) expressed on β-cells are known to modulate the release of insulin in response to changes in plasma glucose levels (Ahren, B., "Autonomic regulation of islet hormone secretion—Implications for health and disease", *Diabetologia*, 43:393-410 (2003)). Those GPCRs specifically coupled to the elevation of cAMP via the $G_s$ alpha subunit of G-protein, have been shown to enhance glucose-stimulated insulin release from β-cells. Cyclic AMP-stimulating GPCRs on β-cells include the GLP-1, GIP, β2-adrenergic receptors and GPR119. Increasing cAMP concentration in β-cells is known to lead to the activation of PKA which is thought to prevent the opening of potassium channels on the surface of the β-cell. The reduction in $K^+$ efflux depolarizes the β-cell leading to an influx of $Ca^{++}$ which promotes the release of insulin.

GPR119 (e.g., human GPR119, GENBANK® Accession No. AAP72125 and alleles thereof; e.g., mouse GPR119, GENBANK® Accession No. AY288423 and alleles thereof) is a GPCR located at chromosome position Xp26.1 (Fredricksson, R. et al., "Seven evolutionarily conserved human rhodopsin G protein-coupled receptors lacking close relatives", *FEBS Lett.*, 554:381-388 (2003)). The receptor is coupled to Gs, and when stimulated, produces an elevation in cAMP in a variety of cell types including β-cell-derived insulinomas (Soga, T. et al., "Lysophosphatidylcholine enhances glucose-dependent insulin secretion via an orphan G-protein-coupled receptor", *Biochem. Biophys. Res. Comm.*, 326:744-751 (2005), international patent applications WO 04/065380, WO 04/076413, WO 05/007647, WO 05/007658, WO 05/121121, WO 06/083491 and EP 1338651). The receptor has been shown to be localized to the β-cells of the pancreas in a number of species as well as in specific cell types of the gastrointestinal tract. Activation of GPR119, with agonist ligands such as lysophosphatidylcholine, produce a glucose dependent increase in insulin secretion from primary mouse islets and various insulinoma cell lines such as NIT-1 and HIT-T15 (Soga, T. et al., "Lysophosphatidylcholine enhances glucose-dependent insulin secretion via an orphan G-protein-coupled receptor", *Biochem. Biophys. Res. Comm.*, 326:744-751 (2005); Chu, Z. L. et al., "A role for β-cell-expressed GPR119 in glycemic control by enhancing glucose-dependent insulin release", *Endocrinology*, doi:10.1210/en.2006-1608 (2007)).

When activators of GPR119 are administered to either normal mice or mice that are prone to diabetes due to genetic mutation, prior to an oral glucose tolerance test, improvements in glucose tolerance are observed. A short-lived increase in plasma glucagon-like peptide-1 and plasma insulin levels are also observed in these treated animals (Chu, Z. L. et al., "A role for β-cell-expressed GPR119 in glycemic control by enhancing glucose-dependent insulin release", *Endocrinology*, doi:10.1210/en.2006-1608 (2007)). In addition to effects on plasma glucose levels, GPR119 activators have also been demonstrated to produce reductions in acute food intake and to reduce body weight in rats following chronic administration (Overton, H. A. et al., "Deorphanization of a G protein-coupled receptor for oleoylethanolamide and its use in the discovery of small-molecule hypophagic agents", *Cell Metabolism*, 3:167-175 (2006), and international patent applications WO 05/007647 and WO 05/007658).

Accordingly, compounds that activate GPR119 could demonstrate a wide range of utilities in treating inflammatory, allergic, autoimmune, metabolic, cancer and/or cardiovascular diseases. PCT Publication Nos. WO 2008/137435 A1, WO 2008/137436 A1, WO 2009/012277 A1, WO 2009/012275 A1 and WO 2010/009183 A1, disclose compounds that activate GPR119. The references also disclose various processes to prepare these compounds.

SUMMARY OF THE INVENTION

In accordance with the present invention, compounds are provided that have the general structure of Formula I:

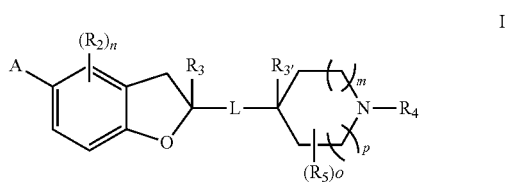

or an enantiomer, diastereomer, tautomer, prodrug or salt thereof, wherein A, L, m, n, o, p, $R_2$, $R_3$, $R_{3'}$, $R_4$ and $R_5$ are defined below.

Compounds of the present invention modulate the activity of G protein-coupled receptors. Preferably, compounds of the present invention modulate the activity of the GPR119 G protein-coupled receptor ("GPR119"). Consequently, the compounds of the present invention may be used in the treatment of multiple diseases or disorders associated with GPR119, such as diabetes and related conditions, microvascular complications associated with diabetes, the macrovascular complications associated with diabetes, cardiovascular diseases, Metabolic Syndrome and its component conditions, obesity and other maladies. Examples of diseases or disorders associated with the modulation of the GPR119 G protein-coupled receptor that can be prevented, modulated, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dislipidemia, dyslipidemia, hyperlipidemia, hypertriglyceridemia, hypercholesterolemia, low HDL, high LDL, non-cardiac ischemia, vascular restenosis, pancreatitis, neurodegenerative disease, lipid disorders, cognitive impairment and dementia, bone disease, HIV protease associated lipodystrophy and glaucoma.

In addition, the present invention relates to a formulated product wherein the selected formulation is made by using a compound of Formula I, Ia, Ib, and the examples, as the only active ingredient or by combining (a) a compound of Formula I, Ia, Ib, and the examples, (using any of the compound embodiments listed herein) and (b) an additional active ingredient, for example, dipeptidyl peptidase-IV (DPP4) inhibitor (for example a member selected from saxagliptin, sitagliptin, vildagliptin and alogliptin).

In addition, the present invention relates to a formulated product wherein the selected formulation is made by using a compound of Formula I, Ia, Ib, and the examples, as the only active ingredient or by combining (a) a compound of Formula I, Ia, Ib, and the examples, (using any of the compound embodiments listed herein) and (b) a dipeptidyl peptidase-IV (DPP4) inhibitor, wherein the DPP4 inhibitor is saxagliptin.

Therefore, in another embodiment, the present invention provides for compounds of Formula I, Ia, Ib, and the examples, pharmaceutical compositions containing such compounds, and for methods of using such compounds. In particular, the present invention provides a pharmaceutical composition comprising a therapeutically effective amount of a compound of Formula I, Ia, Ib, and the examples, alone or in combination with a pharmaceutically acceptable carrier.

Further, in another embodiment, the present invention provides a method for preventing, modulating, or treating the progression or onset of diseases or disorders associated with the activity of the GPR119 G protein-coupled receptor, such as defined above and hereinafter, wherein a therapeutically effective amount of a compound of Formula I, Ia, Ib, and the examples, is administered to a mammalian, i.e., human, patient in need of treatment.

The compounds of the invention can be used alone, in combination with other compounds of the present invention, or in combination with one or more other agent(s).

Further, the present invention provides a method for preventing, modulating, or treating the diseases as defined above and hereinafter, wherein a therapeutically effective amount of a combination of a compound of Formula I, Ia, Ib, and the examples, and another compound of Formula I, Ia, Ib, and the examples, and/or at least one other type of therapeutic agent, is administered to a mammalian, i.e., human, patient in need of treatment.

DETAILED DESCRIPTION

In one embodiment, the present invention provides a compound of Formula I:

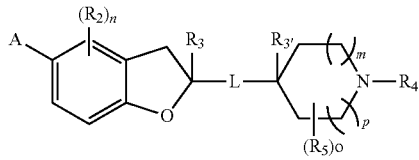

or an enantiomer, diastereomer, tautomer, prodrug or salt thereof wherein:

A is

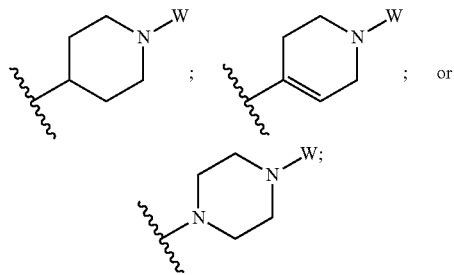

m is 0, 1 or 2;
n is 0-3;
o is 0-4;
p is 0, 1 or 2;
L is a bond, or —$CR_{1a}R_{1a}$—;
W is —$S(=O)_2$—$R_1$, —$S(=O)_2$—$NR_{1a}R_1$, —$C(=O)$-$R_1$, —$C(=O)$—O—$R_1$, —$C(=O)$—$NR_{1a}R_1$ or a 4- to 10-membered heteroaryl, which contains 1-4 heteroatoms selected from N, O, and S and may be optionally substituted with one or more $R_{20}$'s;
$R_1$ is $(C_1-C_6)$-alkyl, $(C_2-C_6)$-alkenyl, $(C_2-C_6)$-alkynyl, $(C_{6-10})$aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —$CO(C_1-C_6)$-alkyl, —$CO_2(C_1-C_6)$-alkyl, —$CONR_{18}R_{19}$, —$NR_{18}R_{19}$, —O(C=O)—$(C_1-C_6)$-alkyl, —O(C=O)$NR_{18}R_{19}$; —$(C_1-C_6)$-alkylCOOH, —$(C_1-C_6)$-alkylOH, —$(C_1-C_6)$—alkyl($NH_2$)COOH, —$(C_1-C_6)$-alkylCONR$_{18}$R$_{19}$, —$(C_1-C_6)$-alkyl-$CO_2(C_1-C_6)$-alkyl, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo($C_1-C_6$)alkyl, and halo($C_1-C_6$)alkyloxy;

$R_{1a}$, at each occurrence, is independently hydrogen or $(C_1-C_8)$alkyl;

$R_2$, at each occurrence, is independently H, halo, —OH, $(C_1-C_6)$-alkyl, $(C_2-C_6)$-alkenyl, $(C_2-C_6)$-alkynyl, $(C_1-C_6)$-alkyloxy, cyano, —$CONR_{18}R_{19}$ or —$NR_{18}R_{19}$; wherein any alkyl may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, halo($C_1-C_6$)alkyl, and halo($C_1-C_6$)alkyloxy;

$R_3$ is hydrogen or $(C_1-C_6)$-alkyl;
$R_{3'}$ is hydrogen, —OH, halo, or $(C_1-C_6)$-alkyl;
$R_4$ is $(C_1-C_6)$-alkyl, $(C_2-C_6)$-alkenyl, $(C_2-C_6)$-alkynyl, —$CO(C_1-C_6)$-alkyl, —$CO_2(C_1-C_6)$-alkyl, —$CO_2(C_3-C_{12})$-cycloalkyl, —$SO_2(C_1-C_6)$-alkyl, $(C_{6-10})$aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, nitro, —COOH, —$CO(C_1-C_6)$-alkyl, —$CO_2(C_1-C_6)$-alkyl, —$CONR_{18}R_{19}$, —$NR_{18}R_{19}$, —O(C=O)—$(C_1-C_6)$-alkyl, —O(C=O)$NR_{18}R_{19}$; —$(C_1-C_6)$-alkylCOOH, —$(C_1-C_6)$—alkylOH, —$(C_1-C_6)$-alkyl($NH_2$)COOH, —$(C_1-C_6)$-alkylCONR$_{18}$R$_{19}$, —$(C_1-C_6)$-alkyl-$CO_2(C_1-C_6)$-alkyl, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo($C_1-C_6$)alkyl, and halo($C_1-C_6$)alkyloxy;

$R_5$, at each occurrence, is independently H, halo, —OH or $(C_1-C_6)$-alkyl;

or two $R_5$'s are taken together with the atom or atoms to which both are attached to form a 3- to 8-membered ring, which may optionally contain 1-4 heteroatoms selected from N, O, and S and be optionally substituted with one or more $R_{20}$'s;

or two $R_5$'s may be taken together with the atoms to which they are attached to form a $(C_1-C_6)$-alkyl bridging group, which may optionally contain 1-4 heteroatoms selected from N, O, and S;

$R_{18}$ and $R_{19}$, at each occurrence, are independently hydrogen or $(C_1-C_8)$alkyl, wherein the alkyl may be optionally substituted with one or more $R_{20}$'s;

or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, —O—P(=O)(OH)$_2$, —O—CR$_{1a}$R$_{1a}$—P(=O)(OH)$_2$, —P(=O)(OH)$_2$, (C$_{6-10}$) aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$; —(C$_1$-C$_6$)—alkylCOOH, —(C$_1$-C$_6$)-alkylOH, —(C$_1$-C$_6$)-alkyl(NH$_2$)COOH, —(C$_1$-C$_6$)-alkylCONR$_{28}$R$_{29}$, —(C$_1$-C$_6$)-alkyl-CO$_2$(C$_1$-C$_6$)-alkyl, (C$_{6-10}$)aryl, a 5- to 10-membered heteroaryl, which contains 1-4 heteroatoms selected from N, O, and S, a 5- to 10-membered heterocyclo, which contains 1-4 heteroatoms selected from N, O, and S; halo(C$_1$-C$_6$)alkyl, and halo(C$_1$-C$_6$)alkyloxy;

R$_{28}$ and R$_{29}$, at each occurrence, are independently hydrogen or (C$_1$-C$_8$)alkyl;

or R$_{28}$ and R$_{29}$ are taken together with the nitrogen to which both are attached to form a 3- to 8-membered ring, which may optionally contain 1-4 heteroatoms selected from N, O, and S.

In another embodiment, the present invention provides compounds, enantiomers, diastereomers, tautomers, or salts thereof, wherein the compounds are compounds of formula Ia:

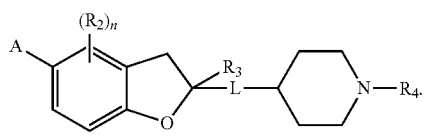

In yet another embodiment, the present invention provides compounds, enantiomers, diastereomers, tautomers, or salts thereof, wherein the compounds are compounds of formula Ib:

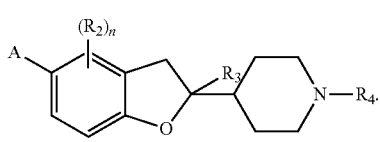

In still yet another embodiment, the present invention provides compounds, enantiomers, diastereomers, tautomers, or salts thereof, wherein:

R$_4$ is a 5- to 10-membered heteroaryl, which contains 1-4 heteroatoms selected from N, O, and S; or a 5- to 10-membered heterocyclo, which contains 1-4 heteroatoms selected from N, O, and S; wherein the heteroaryl, and heterocyclo are substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{18}$R$_{19}$, —NR$_{18}$R$_{19}$, —(C$_1$-C$_6$)-alkylCOOH, —(C$_1$-C$_6$)-alkylOH, —(C$_1$-C$_6$)-alkyl(NH$_2$) COOH, —(C$_1$-C$_6$)-alkylCONR$_{18}$R$_{19}$, —(C$_1$-C$_6$)-alkyl-CO$_2$ (C$_1$-C$_6$)-alkyl, (C$_{6-10}$)aryl, a 5- to 10-membered heteroaryl, which contains 1-4 heteroatoms selected from N, O, and S, a 5- to 10-membered heterocyclo, which contains 1-4 heteroatoms selected from N, O, and S; halo(C$_1$-C$_6$)alkyl, and halo (C$_1$-C$_6$)alkyloxy.

In one embodiment, the present invention provides compounds, enantiomers, diastereomers, tautomers, or salts thereof, wherein L is a bond.

In another embodiment, the present invention provides compounds, enantiomers, diastereomers, tautomers, or salts thereof, wherein L is —CR$_{1a}$R$_{1a}$—.

In yet another embodiment, the present invention provides compounds, enantiomers, diastereomers, tautomers, or salts thereof, wherein A is

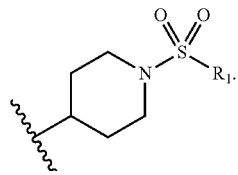

In still yet another embodiment, the present invention provides compounds, enantiomers, diastereomers, tautomers, or salts thereof, wherein A is

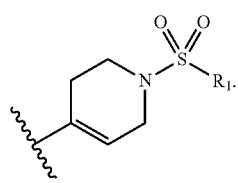

In one embodiment, the present invention provides compounds, enantiomers, diastereomers, tautomers, or salts thereof, wherein A is

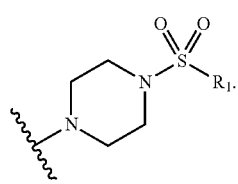

In another embodiment, the present invention provides compounds, enantiomers, diastereomers, tautomers, or salts thereof, wherein L is a bond and A is

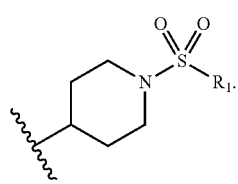

In yet another embodiment, the present invention provides compounds, enantiomers, diastereomers, tautomers, or salts thereof, wherein L is a bond and A is

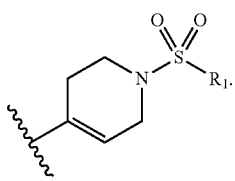

In still yet another embodiment, the present invention provides compounds, enantiomers, diastereomers, tautomers, or salts thereof, wherein L is a bond and A is

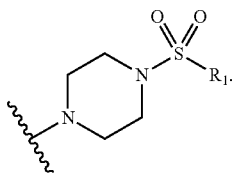

In one embodiment, the present invention provides compounds, enantiomers, diastereomers, tautomers, or salts thereof, wherein:
A is

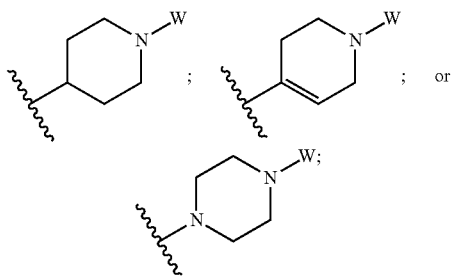

m is 0, 1 or 2;
n is 0-2;
o is 0-3;
p is 0, 1 or 2;
L is a bond, or $-CR_{1a}R_{1a}-$;
W is $-S(=O)_2-R_1$, $-C(=O)-R_1$, $-C(=O)-O-R_1$, $-C(=O)-NR_{1a}R_1$ or a 4- to 10-membered heteroaryl, which contains 1-4 heteroatoms selected from N, O, and S and may be optionally substituted with one or more $R_{20}$'s;
$R_1$ is $(C_1-C_6)$-alkyl, $(C_2-C_6)$-alkenyl, $(C_{6-10})$aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{18}$R$_{19}$, —NR$_{18}$R$_{19}$, —O(C=O)—$(C_1-C_6)$-alkyl, —O(C=O)NR$_{18}$R$_{19}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{18}$R$_{19}$, —$(C_1-C_6)$-alkyl-CO$_2$(C$_1$-C$_6$)-alkyl, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy;

$R_{1a}$, at each occurrence, is independently hydrogen or $(C_1-C_6)$alkyl;
$R_2$, at each occurrence, is independently H, halo, —OH, $(C_1-C_6)$-alkyl, $(C_2-C_6)$-alkenyl, $(C_2-C_6)$-alkynyl, $(C_1-C_6)$-alkyloxy, cyano, —CONR$_{18}$R$_{19}$ or —NR$_{18}$R$_{19}$; wherein any alkyl may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, halo$(C_1-C_6)$alkyl, and halo$(C_1-C_6)$alkyloxy;
$R_3$ is hydrogen or $(C_1-C_6)$-alkyl;
$R_{3'}$ is hydrogen, —OH or halo;
$R_4$ is $(C_1-C_6)$-alkyl, $(C_2-C_6)$-alkenyl, —CO$(C_1-C_6)$-alkyl, —CO$_2$(C$_1$-C$_6$)-alkyl, —CO$_2$(C$_3$-C$_{12}$)-cycloalkyl, —SO$_2$(C$_1$-C$_6$)-alkyl, $(C_{6-10})$aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, nitro, —COOH, —CO$(C_1-C_6)$-alkyl, —CO$_2(C_1-C_6)$-alkyl, —CONR$_{18}$R$_{19}$, —NR$_{18}$R$_{19}$, —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{18}$R$_{19}$, —$(C_1-C_6)$-alkyl-CO$_2$(C$_1$-C$_6$)-alkyl, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy;
$R_5$, at each occurrence, is independently H, halo, —OH or $(C_1-C_6)$-alkyl;
or two $R_5$'s are taken together with the atom or atoms to which both are attached to form a 3- to 8-membered ring, which may optionally contain 1-4 heteroatoms selected from N, O, and S and be optionally substituted with one or more $R_{20}$'s;
$R_{18}$ and $R_{19}$, at each occurrence, are independently hydrogen or $(C_1-C_8)$alkyl, wherein the alkyl may be optionally substituted with one or more $R_{20}$'s;
or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;
$R_{20}$ is halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{28}$R$_{29}$, —NR$_{28}$R$_{29}$, —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2$(C$_1$-C$_6$)-alkyl, —O—P(=O)(OH)$_2$, —O—CR$_{1a}$R$_{1a}$—P(=O)(OH)$_2$, —P(=O)(OH)$_2$, $(C_{6-10})$aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{28}$R$_{29}$, —NR$_{28}$R$_{29}$, —O(C=O)—$(C_1-C_6)$-alkyl, —O(C=O)NR$_{28}$R$_{29}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2$(C$_1$-C$_6$)-alkyl, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy;

$R_{28}$ and $R_{29}$, at each occurrence, are independently hydrogen or $(C_1-C_8)$alkyl;

or $R_{28}$ and $R_{29}$ are taken together with the nitrogen to which both are attached to form a 3- to 8-membered ring, which may optionally contain 1-4 heteroatoms selected from N, O, and S.

In another embodiment, the present invention provides compounds, enantiomers, diastereomers, tautomers, or salts thereof, wherein:

A is

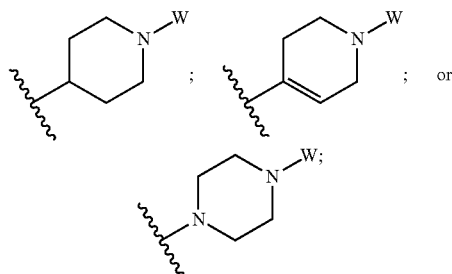

m is 0, 1 or 2;
n is 0-2;
o is 0-2;
p is 0, 1 or 2;
L is a bond, or $-CR_{1a}R_{1a}-$;
W is $-S(=O)_2-R_1$, $-C(=O)-R_1$, $-C(=O)-O-R_1$, $-C(=O)-NR_{1a}R_1$ or a 4- to 10-membered heteroaryl, which contains 1-4 heteroatoms selected from N, O, and S and may be optionally substituted with one or more $R_{20}$'s;

$R_1$ is $(C_1-C_6)$-alkyl, $(C_{6-10})$aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{18}$R$_{19}$, —NR$_{18}$R$_{19}$, —$(C_1-C_6)$-alkylCOOH, —$(C_1-C_6)$-alkylOH, —$(C_1-C_6)$-alkylCONR$_{18}$R$_{19}$, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy;

$R_{1a}$, at each occurrence, is independently hydrogen or $(C_1-C_6)$alkyl;

$R_2$, at each occurrence, is independently H, halo, —OH, $(C_1-C_6)$-alkyl, $(C_2-C_6)$-alkenyl, $(C_2-C_6)$-alkynyl, $(C_1-C_6)$-alkyloxy, cyano, —CONR$_{18}$R$_{19}$ or —NR$_{18}$R$_{19}$; wherein any alkyl may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, halo$(C_1-C_6)$alkyl, and halo$(C_1-C_6)$alkyloxy;

$R_3$ is hydrogen or $(C_1-C_6)$-alkyl;
$R_{3'}$ is hydrogen, —OH or halo;
$R_4$ is $(C_1-C_6)$-alkyl, —CO$(C_1-C_6)$-alkyl, —CO$_2(C_1-C_6)$-alkyl, —CO$_2(C_3-C_{12})$-cycloalkyl, —SO$_2(C_1-C_6)$-alkyl, $(C_{6-10})$aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, nitro, —COOH, —CO$(C_1-C_6)$-alkyl, —CO$_2(C_1-C_6)$-alkyl, —CONR$_{18}$R$_{19}$, —NR$_{18}$R$_{19}$, —$(C_1-C_6)$-alkylCOOH, —$(C_1-C_6)$-alkylOH, —$(C_1-C_6)$-alkylCONR$_{18}$R$_{19}$, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy;

$R_5$, at each occurrence, is independently H, halo, —OH or $(C_1-C_6)$-alkyl;

or two $R_5$'s are taken together with the atom or atoms to which both are attached to form a 3- to 8-membered ring, which may optionally contain 1-4 heteroatoms selected from N, O, and S and be optionally substituted with one or more $R_{20}$'s;

$R_{18}$ and $R_{19}$, at each occurrence, are independently hydrogen or $(C_1-C_8)$alkyl, wherein the alkyl may be optionally substituted with one or more $R_{20}$'s;

or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{28}$R$_{29}$, —NR$_{28}$R$_{29}$, —$(C_1-C_6)$-alkylCOOH, —$(C_1-C_6)$-alkylOH, —$(C_1-C_6)$-alkylCONR$_{28}$R$_{29}$, —O—P(=O)(OH)$_2$, —O—CR$_{1a}$R$_{1a}$—P(=O)(OH)$_2$, —P(=O)(OH)$_2$, $(C_{6-10})$aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{28}$R$_{29}$, —NR$_{28}$R$_{29}$, —O(C=O)—$(C_1-C_6)$-alkyl, —O(C=O)NR$_{28}$R$_{29}$; —$(C_1-C_6)$-alkylCOOH, —$(C_1-C_6)$-alkylOH, —$(C_1-C_6)$-alkylCONR$_{28}$R$_{29}$, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy;

$R_{28}$ and $R_{29}$, at each occurrence, are independently hydrogen or $(C_1-C_8)$alkyl;

or $R_{28}$ and $R_{29}$ are taken together with the nitrogen to which both are attached to form a 3- to 8-membered ring, which may optionally contain 1-4 heteroatoms selected from N, O, and S.

In another embodiment, the present invention provides compounds, enantiomers, diastereomers, tautomers, or salts thereof, wherein:

A is

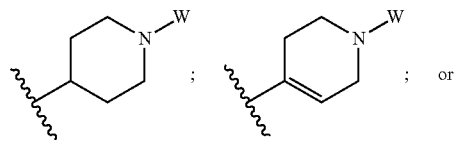

-continued

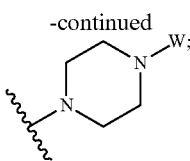

m is 0, 1 or 2;
n is 0-2;
o is 0-1;
p is 0, 1 or 2;
L is a bond, or $-CR_{1a}R_{1a}-$;
W is $-S(=O)_2-R_1$, $-C(=O)-R_1$, $-C(=O)-O-R_1$, $-C(=O)-NR_{1a}R_1$ or a 4- to 10-membered heteroaryl, which contains 1-4 heteroatoms selected from N, O, and S and may be optionally substituted with one or more $R_{20}$'s;

$R_1$ is $(C_1-C_6)$-alkyl, $(C_{6-10})$aryl, or a 5- to 10-membered heteroaryl, which contains 1-4 heteroatoms selected from N, O, and S; wherein any alkyl, aryl and heteroaryl may be optionally substituted with one or more substituents selected from the group consisting of: halo, $-OH$, $(C_1-C_6)$-alkyl, $(C_2-C_6)$-alkenyl, $(C_1-C_6)$-alkyloxy, cyano, nitro, $-COOH$, $-CO(C_1-C_6)$-alkyl, $-CO_2(C_1-C_6)$-alkyl, $-CONR_{18}R_{19}$, $-NR_{18}R_{19}$, $-(C_1-C_6)$-alkylCOOH, $-(C_1-C_6)$-alkylOH, $-(C_1-C_6)$-alkylCONR$_{18}$R$_{19}$, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo($C_1-C_6$)alkyl, and halo($C_1-C_6$)alkyloxy;

$R_{1a}$, at each occurrence, is independently hydrogen or $(C_1-C_5)$alkyl;

$R_2$, at each occurrence, is independently H, halo, $-OH$, $(C_1-C_6)$-alkyl, $(C_2-C_6)$-alkenyl, $(C_2-C_6)$-alkynyl, $(C_1-C_6)$-alkyloxy, cyano or $-NR_{18}R_{19}$; wherein any alkyl, may be optionally substituted with one or more substituents selected from the group consisting of: halo, $-OH$, $(C_1-C_6)$-alkyl, $(C_2-C_6)$-alkenyl, $(C_2-C_6)$-alkynyl, $(C_1-C_6)$-alkyloxy, cyano, nitro, $-COOH$, $-CO(C_1-C_6)$-alkyl, $-CO_2(C_1-C_6)$-alkyl, $-NR_{18}R_{19}$, $-(C_1-C_6)$-alkylCOOH, $-(C_1-C_6)$-alkylOH, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo($C_1-C_6$)alkyl, and halo($C_1-C_6$)alkyloxy;

$R_3$ is hydrogen or $(C_1-C_6)$-alkyl;
$R_{3'}$ is hydrogen, $-OH$ or halo;
$R_4$ is $(C_1-C_6)$-alkyl, $-CO_2(C_1-C_6)$-alkyl, $-CO_2(C_3-C_{12})$-cycloalkyl, $-SO_2(C_1-C_6)$-alkyl, $(C_{6-10})$aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, $-OH$, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, nitro, $-COOH$, $-CO(C_1-C_6)$-alkyl, $-CO_2(C_1-C_6)$-alkyl, $-NR_{18}R_{19}$, $-(C_1-C_6)$-alkylCOOH, $-(C_1-C_6)$-alkylOH, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo($C_1-C_6$)alkyl, and halo($C_1-C_6$)alkyloxy;

$R_5$, at each occurrence, is independently H, halo, $-OH$ or $(C_1-C_6)$-alkyl;

$R_{18}$ and $R_{19}$, at each occurrence, are independently hydrogen or $(C_1-C_8)$alkyl, wherein the alkyl may be optionally substituted with one or more $R_{20}$'s;

or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is halo, $-OH$, $(C_1-C_6)$-alkyl, $(C_2-C_6)$-alkenyl, $(C_2-C_6)$-alkynyl, $(C_1-C_6)$-alkyloxy, cyano, nitro, $-COOH$, $-CO(C_1-C_6)$-alkyl, $-CO_2(C_1-C_6)$-alkyl, $-NR_{28}R_{29}$, $-(C_1-C_6)$-alkylCOOH, $-(C_1-C_6)$-alkylOH, $-O-P(=O)(OH)_2$, $-O-CR_{1a}R_{1a}-P(=O)(OH)_2$, $-P(=O)(OH)_2$, $(C_{6-10})$aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, $-OH$, $(C_1-C_6)$-alkyl, $(C_2-C_6)$-alkenyl, $(C_2-C_6)$-alkynyl, $(C_1-C_6)$-alkyloxy, cyano, nitro, $-COOH$, $-CO(C_1-C_6)$-alkyl, $-CO_2(C_1-C_6)$-alkyl, $-NR_{28}R_{29}$, $-O(C=O)-(C_1-C_6)$-alkyl, $-(C_1-C_6)$-alkylCOOH, $-(C_1-C_6)$-alkylOH, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo($C_1-C_6$)alkyl, and halo($C_1-C_6$)alkyloxy;

$R_{28}$ and $R_{29}$, at each occurrence, are independently hydrogen or $(C_1-C_8)$alkyl;

or $R_{28}$ and $R_{29}$ are taken together with the nitrogen to which both are attached to form a 3- to 8-membered ring, which may optionally contain 1-4 heteroatoms selected from N, O, and S.

In another embodiment, the present invention provides compounds, enantiomers, diastereomers, tautomers, or salts thereof, wherein:
A is

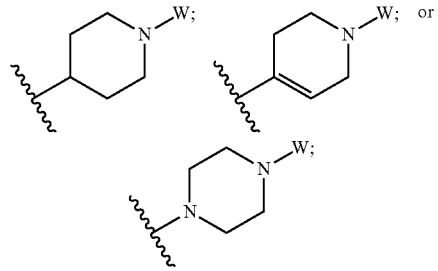

m is 0, 1 or 2;
n is 0-2;
o is 0;
p is 0, 1 or 2;
L is a bond, or $-CR_{1a}R_{1a}-$;
W is $-S(=O)_2-R_1$, $-C(=O)-R_1$, $-C(=O)-O-R_1$, or $-C(=O)-NR_{1a}R_1$;

$R_1$ is $(C_1-C_6)$-alkyl or $(C_{6-10})$aryl; wherein the alkyl and aryl may be optionally substituted with one or more substituents selected from the group consisting of: halo, $-OH$, $(C_1-C_6)$-alkyl, $(C_2-C_6)$-alkenyl, $(C_1-C_6)$-alkyloxy, cyano, nitro, $-COOH$, $-CO(C_1-C_6)$-alkyl, $-CO_2(C_1-C_6)$-alkyl, $-NR_{18}R_{19}$, $-(C_1-C_6)$-alkylCOOH, $-(C_1-C_6)$-alkylOH, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo($C_1-C_6$)alkyl, and halo($C_1-C_6$)alkyloxy;

$R_{1a}$, at each occurrence, is independently hydrogen or ($C_1$-$C_4$)alkyl;

$R_2$, at each occurrence, is independently H, halo, —OH, ($C_1$-$C_6$)-alkyl, ($C_1$-$C_6$)-alkyloxy, cyano or —$NR_{18}R_{19}$; wherein any alkyl may be optionally substituted with one or more substituents selected from the group consisting of: halo, —OH, ($C_1$-$C_6$)-alkyl, ($C_1$-$C_6$)-alkyloxy, cyano, nitro, —COOH, —CO($C_1$-$C_6$)-alkyl, —$CO_2$($C_1$-$C_6$)-alkyl, —$NR_{18}R_{19}$, —($C_1$-$C_6$)-alkylCOOH, —($C_1$-$C_6$)-alkylOH, ($C_{6-10}$)aryl, a 5- to 10-membered heteroaryl, which contains 1-4 heteroatoms selected from N, O, and S, a 5- to 10-membered heterocyclo, which contains 1-4 heteroatoms selected from N, O, and S; halo($C_1$-$C_6$)alkyl, and halo($C_1$-$C_6$)alkyloxy;

$R_3$ is hydrogen or ($C_1$-$C_6$)-alkyl;

$R_{3'}$ is hydrogen or halo;

$R_4$ is ($C_1$-$C_6$)-alkyl, —$CO_2$($C_1$-$C_6$)-alkyl, —$CO_2$($C_3$-$C_{12}$)-cycloalkyl, —$SO_2$($C_1$-$C_6$)-alkyl, ($C_{6-10}$)aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, ($C_1$-$C_6$)-alkyl, ($C_3$-$C_{12}$)-cycloalkyl, ($C_1$-$C_6$)-alkyloxy, cyano, nitro, —COOH, —CO($C_1$-$C_6$)-alkyl, —$CO_2$($C_1$-$C_6$)-alkyl, —$NR_{18}R_{19}$, —($C_1$-$C_6$)-alkylCOOH, —($C_1$-$C_6$)-alkylOH, ($C_{6-10}$)aryl, a 5- to 10-membered heteroaryl, which contains 1-4 heteroatoms selected from N, O, and S, a 5- to 10-membered heterocyclo, which contains 1-4 heteroatoms selected from N, O, and S; halo($C_1$-$C_6$)alkyl, and halo($C_1$-$C_6$)alkyloxy;

$R_{18}$ and $R_{19}$, at each occurrence, are independently hydrogen or ($C_1$-$C_8$)alkyl, wherein the alkyl may be optionally substituted with one or more $R_{20}$'s;

$R_{20}$ is halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —$CO_2$($C_1$-$C_6$)-alkyl, —$NR_{28}R_{29}$, —($C_1$-$C_6$)-alkylCOOH, —($C_1$-$C_6$)-alkylOH, ($C_{6-10}$)aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, ($C_1$-$C_6$)-alkyl, ($C_2$-$C_6$)-alkenyl, ($C_2$-$C_6$)-alkynyl, ($C_1$-$C_6$)-alkyloxy, cyano, nitro, —COOH, —CO($C_1$-$C_6$)-alkyl, —$CO_2$($C_1$-$C_6$)-alkyl, —$NR_{28}R_{29}$, —O(C=O)—($C_1$-$C_6$)-alkyl, —($C_1$-$C_6$)-alkylCOOH, —($C_1$-$C_6$)-alkylOH, ($C_{6-10}$)aryl, a 5- to 10-membered heteroaryl, which contains 1-4 heteroatoms selected from N, O, and S, a 5- to 10-membered heterocyclo, which contains 1-4 heteroatoms selected from N, O, and S; halo($C_1$-$C_6$)alkyl, and halo($C_1$-$C_6$)alkyloxy;

$R_{28}$ and $R_{29}$, at each occurrence, are independently hydrogen or ($C_1$-$C_8$)alkyl.

In one embodiment, the present invention provides compounds, enantiomers, diastereomers, tautomers, or salts thereof, wherein:

A is

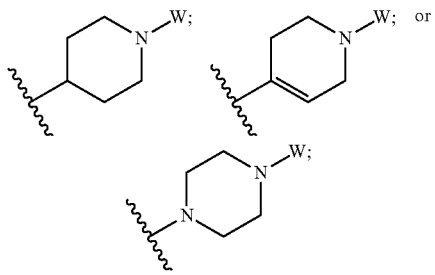

m is 0, 1 or 2;

n is 0-2;

o is 0;

p is 0, 1 or 2;

L is a bond, or —$CR_{1a}R_{1a}$—;

W is —S(=O)$_2$—$R_1$, —C(=O)—$R_1$ or —C(=O)—O—$R_1$;

$R_1$ is ($C_1$-$C_6$)-alkyl; wherein the alkyl may be optionally substituted with one or more substituents selected from the group consisting of: halo, —OH, ($C_1$-$C_6$)-alkyl, ($C_1$-$C_6$)-alkyloxy, cyano, nitro, —CO($C_1$-$C_6$)-alkyl, —$CO_2$($C_1$-$C_6$)-alkyl, —$NR_{18}R_{19}$, —($C_1$-$C_6$)-alkylCOOH, —($C_1$-$C_6$)-alkylOH, ($C_{6-10}$)aryl, a 5- to 10-membered heteroaryl, which contains 1-4 heteroatoms selected from N, O, and S, a 5- to 10-membered heterocyclo, which contains 1-4 heteroatoms selected from N, O, and S; halo($C_1$-$C_6$)alkyl, and halo($C_1$-$C_6$)alkyloxy;

$R_{1a}$, at each occurrence, is independently hydrogen or ($C_1$-$C_4$)alkyl;

$R_2$, at each occurrence, is independently H, halo, —OH, ($C_1$-$C_6$)-alkyl, ($C_1$-$C_6$)-alkyloxy, cyano or —$NR_{18}R_{19}$; wherein any alkyl may be optionally substituted with one or more substituents selected from the group consisting of: halo, —OH, ($C_1$-$C_6$)-alkyl, ($C_1$-$C_6$)-alkyloxy, cyano, nitro, —COOH, —CO($C_1$-$C_6$)-alkyl, —$CO_2$($C_1$-$C_6$)-alkyl, —$NR_{18}R_{19}$, —($C_1$-$C_6$)-alkylCOOH, —($C_1$-$C_6$)-alkylOH, ($C_{6-10}$)aryl, a 5- to 10-membered heteroaryl, which contains 1-4 heteroatoms selected from N, O, and S, a 5- to 10-membered heterocyclo, which contains 1-4 heteroatoms selected from N, O, and S; halo($C_1$-$C_6$)alkyl, and halo($C_1$-$C_6$)alkyloxy;

$R_3$ is hydrogen or ($C_1$-$C_4$)-alkyl;

$R_{3'}$ is hydrogen or halo;

$R_4$ is —$CO_2$($C_1$-$C_6$)-alkyl, —$CO_2$($C_3$-$C_{12}$)-cycloalkyl, —$SO_2$($C_1$-$C_6$)-alkyl, ($C_{6-10}$)aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, ($C_1$-$C_6$)-alkyl, ($C_3$-$C_{12}$)-cycloalkyl, ($C_1$-$C_6$)-alkyloxy, cyano, nitro, —COOH, —CO($C_1$-$C_6$)-alkyl, —$CO_2$($C_1$-$C_6$)-alkyl, —$NR_{18}R_{19}$, —($C_1$-$C_6$)-alkylCOOH, —($C_1$-$C_6$)-alkylOH, ($C_{6-10}$)aryl, a 5- to 10-membered heteroaryl, which contains 1-4 heteroatoms selected from N, O, and S, a 5- to 10-membered heterocyclo, which contains 1-4 heteroatoms selected from N, O, and S; halo($C_1$-$C_6$)alkyl, and halo($C_1$-$C_6$)alkyloxy;

$R_{18}$ and $R_{19}$, at each occurrence, are independently hydrogen or ($C_1$-$C_8$)alkyl, wherein the alkyl may be optionally substituted with one or more $R_{20}$'s;

$R_{20}$ is halo, —OH, $(C_1-C_6)$-alkyl, $(C_1-C_6)$-alkyloxy, cyano, nitro, —COOH, —CO$(C_1-C_6)$-alkyl, —CO$_2(C_1-C_6)$-alkyl, —NR$_{28}$R$_{29}$, —$(C_1-C_6)$-alkylCOOH, —$(C_1-C_6)$-alkylOH, $(C_{6-10})$aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, $(C_1-C_6)$-alkyl, $(C_1-C_6)$-alkyloxy, cyano, nitro, —COOH, —CO$(C_1-C_6)$-alkyl, —CO$_2(C_1-C_6)$-alkyl, —NR$_{28}$R$_{29}$, —O(C=O)—$(C_1-C_6)$-alkyl, —$(C_1-C_6)$-alkylCOOH, —$(C_1-C_6)$-alkylOH, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy;

$R_{28}$ and $R_{29}$, at each occurrence, are independently hydrogen or $(C_1-C_8)$alkyl.

In another embodiment, the present invention provides compounds, enantiomers, diastereomers, tautomers, or salts thereof, wherein:

A is

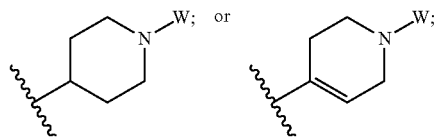

m is 0, 1 or 2;
n is 0-2;
o is 0;
p is 0 or 1;
L is a bond, or —CR$_{1a}$R$_{1a}$—;
W is —S(=O)$_2$—R$_1$ or —C(=O)—R$_1$;
R$_1$ is $(C_1-C_6)$-alkyl; wherein the alkyl may be optionally substituted with one or more substituents selected from the group consisting of: halo, —OH, $(C_1-C_6)$-alkyl, $(C_1-C_6)$-alkyloxy, cyano, nitro, —CO$(C_1-C_6)$-alkyl, —CO$_2(C_1-C_6)$-alkyl, —NR$_{18}$R$_{19}$, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy;

R$_{1a}$, at each occurrence, is independently hydrogen or $(C_1-C_4)$alkyl;

R$_2$, at each occurrence, is independently H, halo, —OH, $(C_1-C_6)$-alkyl, $(C_1-C_6)$-alkyloxy, cyano or —NR$_{18}$R$_{19}$; wherein any alkyl may be optionally substituted with one or more substituents selected from the group consisting of: halo, —OH, $(C_1-C_6)$-alkyl, $(C_1-C_6)$-alkyloxy, cyano, nitro, —CO$(C_1-C_6)$-alkyl, —CO$_2(C_1-C_6)$-alkyl, —NR$_{18}$R$_{19}$, —$(C_1-C_6)$-alkylOH, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy;

R$_3$ is hydrogen or $(C_1-C_4)$-alkyl;
R$_3'$ is hydrogen or halo;
R$_4$ is —CO$_2(C_1-C_6)$-alkyl, —CO$_2(C_3-C_{12})$-cycloalkyl, —SO$_2(C_1-C_6)$-alkyl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, heteroaryl, and heterocyclo may be optionally substituted with one or more substituents selected from the group consisting of: halo, —OH, $(C_1-C_6)$-alkyl, $(C_3-C_{12})$-cycloalkyl, $(C_1-C_6)$-alkyloxy, cyano, nitro, —CO$(C_1-C_6)$-alkyl, —CO$_2(C_1-C_6)$-alkyl, —NR$_{18}$R$_{19}$, —$(C_1-C_6)$-alkylOH, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy;

R$_{18}$ and R$_{19}$, at each occurrence, are independently hydrogen or $(C_1-C_8)$alkyl, wherein the alkyl may be optionally substituted with one or more R$_{20}$'s;

R$_{20}$ is halo, —OH, $(C_1-C_6)$-alkyl, $(C_1-C_6)$-alkyloxy, cyano, nitro, —CO$(C_1-C_6)$-alkyl, —CO$_2(C_1-C_6)$-alkyl, —NR$_{28}$R$_{29}$, —$(C_1-C_6)$-alkylOH, $(C_{6-10})$aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, $(C_1-C_6)$-alkyl, $(C_1-C_6)$-alkyloxy, cyano, nitro, —CO$(C_1-C_6)$-alkyl, —CO$_2$ $(C_1-C_6)$-alkyl, —NR$_{28}$R$_{29}$, —$(C_1-C_6)$-alkylOH, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy;

R$_{28}$ and R$_{29}$, at each occurrence, are independently hydrogen or $(C_1-C_8)$alkyl.

In another embodiment, the present invention provides compounds, enantiomers, diastereomers, tautomers, or salts thereof, wherein:

A is

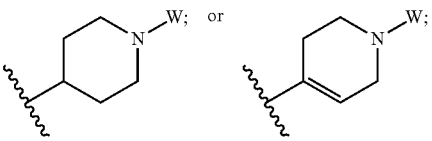

m is 0 or 1;
n is 0-2;
o is 0;
p is 0 or 1;
L is a bond, or —CR$_{1a}$R$_{1a}$—;
W is —S(=O)$_2$—R$_1$ or —C(=O)—R$_1$;
R$_1$ is $(C_1-C_6)$-alkyl; wherein the alkyl may be optionally substituted with one or more substituents selected from the group consisting of: halo, —OH, $(C_1-C_6)$-alkyl, $(C_1-C_6)$-alkyloxy, cyano, nitro, —CO$(C_1-C_6)$-alkyl, —CO$_2(C_1-C_6)$-alkyl, $(C_{6-10})$aryl, a 5- to 10-membered heteroaryl, which contains 1-4 heteroatoms selected from N, O, and S, halo$(C_1-C_6)$alkyl, and halo$(C_1-C_6)$alkyloxy;

R$_{1a}$, at each occurrence, is independently hydrogen or $(C_1-C_4)$alkyl;

R$_2$, at each occurrence, is independently H, halo, —OH, $(C_1-C_6)$-alkyl, $(C_1-C_6)$-alkyloxy or cyano; wherein any alkyl may be optionally substituted with one or more substituents selected from the group consisting of: halo, —OH, $(C_1-C_6)$-alkyl, $(C_1-C_6)$-alkyloxy, cyano, nitro, —CO$(C_1-C_6)$-alkyl, —$(C_1-C_6)$-alkylOH, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy;

$R_3$ is hydrogen or $(C_1-C_4)$-alkyl;

$R_{3'}$ is hydrogen, F, or Cl; and $R_4$ is $-CO_2(C_1-C_6)$-alkyl, $-SO_2(C_1-C_6)$-alkyl or a 5- to 10-membered heteroaryl, which contains 1-4 heteroatoms selected from N, O, and S; wherein any alkyl and heteroaryl may be optionally substituted with one or more substituents selected from the group consisting of: halo, $-OH$, $(C_1-C_6)$-alkyl, $(C_3-C_{12})$-cycloalkyl, $(C_1-C_6)$-alkyloxy, cyano, nitro, $-CO(C_1-C_6)$-alkyl, $-(C_1-C_6)$-alkylOH, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy.

In one embodiment, the present invention provides compounds, enantiomers, diastereomers, tautomers, or salts thereof, wherein:

A is

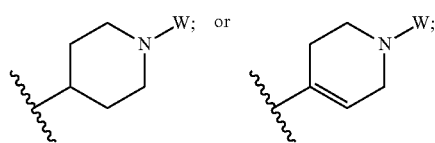

m is 1;
n is 0-2;
o is 0;
p is 1;
L is a bond, or $-CR_{1a}R_{1a}-$;
W is $-S(=O)_2-R_1$ or $-C(=O)-R_1$;
$R_1$ is $(C_1-C_6)$-alkyl; wherein the alkyl may be optionally substituted with one or more substituents selected from the group consisting of: halo, $-OH$, $(C_1-C_6)$-alkyl, $-CO_2(C_1-C_6)$-alkyl, $(C_{6-10})$aryl, a 5- to 10-membered heteroaryl, which contains 1-4 heteroatoms selected from N, O, and S, halo$(C_1-C_6)$alkyl, and halo$(C_1-C_6)$alkyloxy;

$R_{1a}$, at each occurrence, is independently hydrogen or $(C_1-C_4)$alkyl;

$R_2$, at each occurrence, is independently H, halo, $-OH$ or $(C_1-C_6)$-alkyl; wherein any alkyl may be optionally substituted with one or more substituents selected from the group consisting of: halo, $-OH$, $(C_1-C_6)$-alkyl, $(C_1-C_6)$-alkyloxy, cyano, nitro, $-CO(C_1-C_6)$-alkyl, $-(C_1-C_6)$-alkylOH, $(C_{6-10})$aryl, a 5- to 10-membered heteroaryl, which contains 1-4 heteroatoms selected from N, O, and S, halo$(C_1-C_6)$alkyl, and halo$(C_1-C_6)$alkyloxy;

$R_3$ is hydrogen or $(C_1-C_4)$-alkyl;

$R_{3'}$ is hydrogen or F; and $R_4$ is $-CO_2(C_1-C_6)$-alkyl or a 6-membered heteroaryl, which contains 1-4 heteroatoms selected from N, O, and S; wherein any heteroaryl may be optionally substituted with one or more substituents selected from the group consisting of: halo, $-OH$, $(C_1-C_6)$-alkyl, $-CO(C_1-C_6)$-alkyl, $(C_3-C_{12})$-cycloalkyl, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy.

In one embodiment, the present invention provides compounds, enantiomers, diastereomers, tautomers, or salts thereof, wherein:

A is

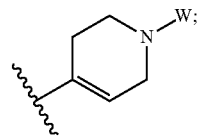

m is 1;
n is 0-2;
o is 0;
p is 1;
L is a bond, or $-CR_{1a}R_{1a}-$;
W is $-S(=O)_2-R_1$;
$R_1$ is $(C_1-C_6)$-alkyl; wherein the alkyl may be optionally substituted with one or more substituents selected from the group consisting of: F, Cl, $-OH$, $(C_1-C_6)$-alkyl, $-CO_2(C_1-C_6)$-alkyl or phenyl;

$R_{1a}$, at each occurrence, is independently hydrogen or $(C_1-C_4)$alkyl;

$R_2$, at each occurrence, is independently H, Cl, F, $-OH$ or $(C_1-C_6)$-alkyl;

$R_3$ is hydrogen or $(C_1-C_4)$-alkyl;

$R_{3'}$ is hydrogen; and $R_4$ is $-CO_2(C_1-C_6)$-alkyl, pyridinyl or pyrimidinyl, which is substituted with one or more substituents selected from the group consisting of: halo, $-OH$, $(C_1-C_6)$-alkyl, $(C_3-C_{12})$-cycloalkyl, phenyl, a 5- to 10-membered heteroaryl, which contains 1-4 heteroatoms selected from N, O, and S; halo$(C_1-C_6)$alkyl, and halo$(C_1-C_6)$alkyloxy.

The terms "Formula I", "Formula Ia", "Formula Ib" and all embodiments thereof shall include enantiomers, diastereomers, prodrugs, solvates and salts thereof (particularly enantiomers, diastereomers and pharmaceutically acceptable salts thereof).

In another embodiment, the present invention provides a compound of Formula I, or an enantiomer, a diastereomer, or a pharmaceutically acceptable salt thereof, wherein the compound is selected from one of the examples, preferably examples 4, 6, 8, 11, 37, 38, 43, 49 and 50, more preferably, examples 4, 11, 38, 43 and 49.

For each of the embodiments described in this application, further and more particular values of the terms used in each of the embodiments may be selected. These values may be used individually in any of the embodiments or in any combination. It is noted that for any occurrences of "=O", these may be used with suitable accommodation in the bond structure at that site as will be appreciated by those skilled in the art.

In one embodiment, the present invention relates to methods of modulating the activity of the GPR119 G protein-coupled receptor comprising administering to a mammalian patient, for example, a human patient, in need thereof a therapeutically effective amount of a compound of Formula I, Ia or Ib, preferably, a compound selected from one of the examples, more preferably examples 4, 6, 8, 11, 37, 38, 43, 49 and 50, even more preferably, examples 4, 11, 38, 43 and 49, alone, or optionally, in combination with another compound of the present invention and/or at least one other type of therapeutic agent.

In one embodiment, the present invention relates to a method for preventing, modulating, or treating the progression or onset of diseases or disorders associated with the activity of the GPR119 G protein-coupled receptor comprising administering to a mammalian patient, for example, a human patient, in need of prevention, modulation, or treatment a therapeutically effective amount of a compound of Formula I, Ia or Ib, preferably, a compound selected from one of the examples, more preferably examples 4, 6, 8, 11, 37, 38, 43, 49 and 50, even more preferably, examples 4, 11, 38, 43 and 49, alone, or, optionally, in combination with another compound of the present invention and/or at least one other type of therapeutic agent.

Examples of diseases or disorders associated with the activity of the GPR119 G protein-coupled receptor that can be prevented, modulated, or treated according to the present invention include, but are not limited to, diabetes, hyperglycemia, impaired glucose tolerance, insulin resistance, hyperinsulinemia, retinopathy, neuropathy, nephropathy, delayed wound healing, atherosclerosis and its sequelae, abnormal heart function, myocardial ischemia, stroke, Metabolic Syndrome, hypertension, obesity, dislipidemia, dyslipidemia, hyperlipidemia, hypertriglyceridemia, hypercholesterolemia, low HDL, high LDL, non-cardiac ischemia, infection, cancer, vascular restenosis, pancreatitis, neurodegenerative disease, lipid disorders, cognitive impairment and dementia, bone disease, HIV protease associated lipodystrophy and glaucoma.

In another embodiment, the present invention relates to a method for preventing, modulating, or treating the progression or onset of diabetes, hyperglycemia, obesity, dyslipidemia, hypertension and cognitive impairment comprising administering to a mammalian patient, for example, a human patient, in need of prevention, modulation, or treatment a therapeutically effective amount of a compound of Formula I, Ia or Ib, preferably, a compound selected from one of the examples, more preferably examples 4, 6, 8, 11, 37, 38, 43, 49 and 50, even more preferably, examples 4, 11, 38, 43 and 49, alone, or, optionally, in combination with another compound of the present invention and/or at least one other type of therapeutic agent.

In another embodiment, the present invention relates to a method for preventing, modulating, or treating the progression or onset of diabetes, comprising administering to a mammalian patient, for example, a human patient, in need of prevention, modulation, or treatment a therapeutically effective amount of a compound of Formula I, Ia or Ib, preferably, a compound selected from one of the examples, more preferably examples 4, 6, 8, 11, 37, 38, 43, 49 and 50, even more preferably, examples 4, 11, 38, 43 and 49, alone, or, optionally, in combination with another compound of the present invention and/or at least one other type of therapeutic agent.

In yet another embodiment, the present invention relates to a method for preventing, modulating, or treating the progression or onset of hyperglycemia comprising administering to a mammalian patient, for example, a human patient, in need of prevention, modulation, or treatment a therapeutically effective amount of a compound of Formula I, Ia or Ib, preferably, a compound selected from one of the examples, more preferably examples 4, 6, 8, 11, 37, 38, 43, 49 and 50, even more preferably, examples 4, 11, 38, 43 and 49, alone, or, optionally, in combination with another compound of the present invention and/or at least one other type of therapeutic agent.

In still yet another embodiment, the present invention relates to a method for preventing, modulating, or treating the progression or onset of obesity comprising administering to a mammalian patient, for example, a human patient, in need of prevention, modulation, or treatment a therapeutically effective amount of a compound of Formula I, Ia or Ib, preferably, a compound selected from one of the examples, more preferably examples 4, 6, 8, 11, 37, 38, 43, 49 and 50, even more preferably, examples 4, 11, 38, 43 and 49, alone, or, optionally, in combination with another compound of the present invention and/or at least one other type of therapeutic agent.

In one embodiment, the present invention relates to a method for preventing, modulating, or treating the progression or onset of dyslipidemia comprising administering to a mammalian patient, for example, a human patient, in need of prevention, modulation, or treatment a therapeutically effective amount of a compound of Formula I, Ia or Ib, preferably, a compound selected from one of the examples, more preferably examples 4, 6, 8, 11, 37, 38, 43, 49 and 50, even more preferably, examples 4, 11, 38, 43 and 49, alone, or, optionally, in combination with another compound of the present invention and/or at least one other type of therapeutic agent.

In another embodiment, the present invention relates to a method for preventing, modulating, or treating the progression or onset of hypertension comprising administering to a mammalian patient, for example, a human patient, in need of prevention, modulation, or treatment a therapeutically effective amount of a compound of Formula I, Ia or Ib, preferably, a compound selected from one of the examples, more preferably examples 4, 6, 8, 11, 37, 38, 43, 49 and 50, even more preferably, examples 4, 11, 38, 43 and 49, alone, or, optionally, in combination with another compound of the present invention and/or at least one other type of therapeutic agent.

In another embodiment, the present invention relates to a formulated product, for example a spray dried dispersion, wherein the selected formulation is made by combining (a) a compound of Formula I, Ia or Ib, preferably, a compound selected from one of the examples, more preferably examples 4, 6, 8, 11, 37, 38, 43, 49 and 50, even more preferably, examples 4, 11, 38, 43 and 49 (using any of the compound embodiments listed above), and (b) a dipeptidyl peptidase-IV (DPP4) inhibitor (for example, a member selected from saxagliptin, sitagliptin, vildagliptin and alogliptin).

In another embodiment, the present invention relates to a formulated product, for example a spray dried dispersion, wherein the selected formulation is made by combining (a) a compound of Formula I, Ia or Ib, preferably, a compound selected from one of the examples, more preferably examples 4, 6, 8, 11, 37, 38, 43, 49 and 50, even more preferably, examples 4, 11, 38, 43 and 49 (using any of the compound embodiments listed above), and (b) a dipeptidyl peptidase-IV (DPP4) inhibitor, wherein the DPP4 inhibitor is saxagliptin.

The invention may be embodied in other specific forms without departing from the spirit or essential attributes thereof. This invention also encompasses all combinations of alternative aspects of the invention noted herein. It is understood that any and all embodiments of the present invention may be taken in conjunction with any other embodiment to describe additional embodiments of the present invention. Furthermore, any elements of an embodiment may be combined with any and all other elements from any of the embodiments to describe additional embodiments.

Definitions

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

One enantiomer of a compound of Formula I, Ia or Ib may display superior activity compared with the other. Thus, all of the stereochemistries are considered to be a part of the present invention. When required, separation of the racemic material can be achieved by high performance liquid chromatography (HPLC) using a chiral column or by a resolution using a resolving agent such as camphonic chloride as in Young, S. D. et al., *Antimicrobial Agents and Chemotherapy*, 2602-2605 (1995).

To the extent that compounds of Formula I, Ia or Ib, and salts thereof, may exist in their tautomeric form, all such tautomeric forms are contemplated herein as part of the present invention.

The term "substituted," as used herein, means that any one or more hydrogens on the designated atom or ring is replaced with a selection from the indicated group, provided that the designated atom's or ring atom's normal valency is not exceeded, and that the substitution results in a stable compound. When a substituent is keto (i.e., =O), then 2 hydrogens on the atom are replaced.

When any variable (e.g., $R_5$) occurs more than one time in any constituent or formula for a compound, its definition at each occurrence is independent of its definition at every other occurrence. Thus, for example, if a group is shown to be substituted with $(R_5)_n$ and n is 0-3, then said group may optionally be substituted with up to three $R_5$ groups and $R_5$ at each occurrence is selected independently from the definition of $R_5$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

Unless otherwise indicated, the term "alkyl" is intended to include both branched and straight-chain saturated aliphatic hydrocarbon groups containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups may optionally include 1 to 4 substituents such as halo, for example F, Br, Cl, or I, or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl, and/or alkylthio.

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio, and/or any of the alkyl substituents set out herein.

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl, and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

Unless otherwise indicated, the term "cycloalkyl" as employed herein alone or as part of another group includes saturated or partially unsaturated (containing 1 or 2 double bonds) cyclic hydrocarbon groups containing 1 to 10 rings, preferably 1 to 3 rings, including monocyclic alkyl, bicyclic alkyl (or bicycloalkyl) and tricyclic alkyl, containing a total of 3 to 20 carbons forming the ring, preferably 3 to 15 carbons, more preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl, cyclododecyl, cyclohexenyl,

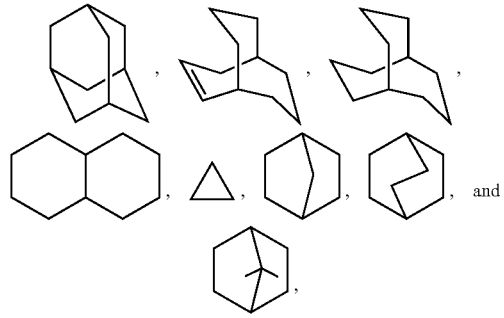

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol, and/or alkylthio, and/or any of the substituents for alkyl.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

"Halo" or "halogen" as used herein refers to fluoro, chloro, bromo, and iodo; and "haloalkyl" is intended to include both branched and straight-chain saturated aliphatic hydrocarbon groups, for example CF$_3$, having the specified number of carbon atoms, substituted with 1 or more halogen (for example —C$_v$F$_w$ where v=1 to 3 and w=1 to (2v+1)).

Unless otherwise indicated, the term "aryl" as employed herein alone or as part of another group refers to monocyclic and bicyclic aromatic groups containing 6 to 10 carbons in the ring portion (such as phenyl or naphthyl, including 1-naphthyl and 2-naphthyl) and may optionally include 1 to 3 additional rings fused to a carbocyclic ring or a heterocyclic ring (such as aryl, cycloalkyl, heteroaryl, or cycloheteroalkyl rings, for example,

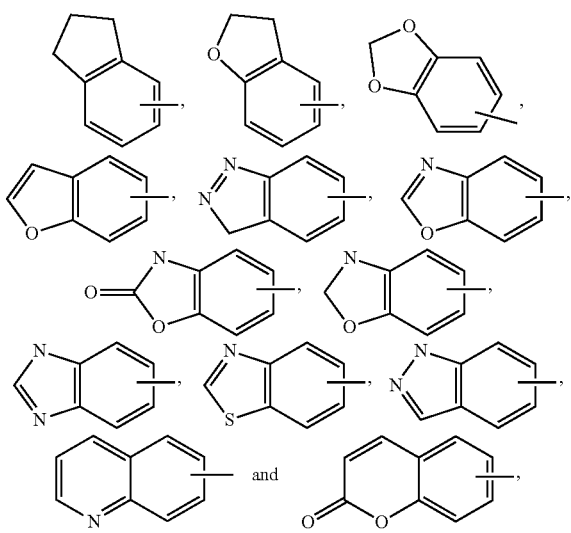

and may be optionally substituted through available carbon atoms with 1, 2, or 3 substituents, for example, hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl, or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino, or arylsulfonaminocarbonyl, and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl, or aryl groups linked to an oxygen atom.

Unless otherwise indicated, the term "amino" as employed herein alone or as part of another group refers to amino that may be substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl, or thioalkyl. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl, or hydroxy.

Unless otherwise indicated, the term "lower alkylthio," "alkylthio," "arylthio," or "aralkylthio" as employed herein alone or as part of another group includes any of the above alkyl, aralkyl, or aryl groups linked to a sulfur atom.

Unless otherwise indicated, the term "lower alkylamino," "alkylamino," "arylamino," or "arylalkylamino" as employed herein alone or as part of another group includes any of the above alkyl, aryl, or arylalkyl groups linked to a nitrogen atom.

Unless otherwise indicated, the term "heterocyclyl" is intended to mean a stable 4- to 14-membered monocyclic, bicyclic or tricyclic heterocyclic ring which is saturated or partially unsaturated and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom, which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another.

Examples of heterocycles include, but are not limited to, pyrrolidonyl, 4-piperidonyl, chromanyl, decahydroquinolinyl, dihydrofuro[2,3-b]tetrahydrofuran, indolinyl, isochromanyl, isoindolinyloctahydroisoquinolinyl, piperazinyl, piperidinyl, piperidonyl, 4-piperidonyl, tetrahydrofuranyl, tetrahydroisoquinolinyl, tetrahydroquinolinyl, morpholinyl, dihydrofuranyl, tetrahydrothiophenyl, pyranyl, dihydropyranyl, 1,4-dioxanyl and 1,3-dioxanyl. Also included are fused ring and spiro compounds containing, for example, the above heterocycles.

Unless otherwise indicated, the term "heteroaryl" is intended to mean a stable 5- to 7-membered monocyclic or bicyclic or 7- to 10-membered bicyclic heterocyclic aromatic ring which consists of carbon atoms and from 1 to 4 heteroatoms independently selected from the group consisting of N, O and S and is aromatic in nature.

Examples of heteroaryls are 1H-indazole, 2H,6H-1,5,2-dithiazinyl, indolyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro-[2,3-b]tetrahydrofuran, furanyl, furazanyl, imidazolidinyl, imidazolinyl, imidazolyl, indazolyl, indolenyl, indolinyl, indolizinyl, indolyl, isobenzofuranyl, isochromanyl, isoindazolyl, isoindolinyl, isoindolyl, isoquinolinyl(benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, pteridinyl, purinyl, pyranyl, pyrazinyl, pyrazolidinyl, pyrazolinyl, pyrazolyl, pyrazolotriazinyl, pyridazinyl, pyridooxazole, pyridoimidazole, pyridothiazole, pyridinyl, pyridyl, pyrimidinyl, pyrrolidinyl, quinazolinyl, quinolinyl, 4H-quinolizinyl, quinoxalinyl, quinuclidinyl, carbolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In another aspect of the invention, examples of heteroaryls are indolyl, benzimidazolyl, benzofuranyl, benzothiofuranyl, benzoxazolyl, benzthiazolyl, benztriazolyl, benztetrazolyl, benzisoxazolyl, benzisothiazolyl, benzimidazalonyl, cinnolinyl, furanyl, imidazolyl, indazolyl, indolyl, isoquinolinyl isothiazolyl, isoxazolyl, oxazolyl, pyrazinyl, pyrazolyl, pyrazolotriazinyl, pyridazinyl, pyridyl, pyridinyl, pyrimidinyl, pyrrolyl, quinazolinyl, quinolinyl, thiazolyl, thienyl, and tetrazolyl.

The term " heterocyclylalkyl" as used herein alone or as part of another group refers to heterocyclyl groups as defined above linked through a C atom or heteroatom to an alkyl chain.

The term "heteroarylalkyl" or "heteroarylalkenyl" as used herein alone or as part of another group refers to a heteroaryl group as defined above linked through a C atom or heteroatom to an alkyl chain, alkylene, or alkenylene as defined above.

The term "cyano" as used herein, refers to a —CN group.

The term "nitro" as used herein, refers to an —$NO_2$ group.

The term "hydroxy" as used herein, refers to an OH group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., p. 1418 (1985), the disclosure of which is hereby incorporated by reference.

Any compound that can be converted in vivo to provide the bioactive agent (i.e., a compound of Formula I, Ia or Ib) is a prodrug within the scope and spirit of the invention.

The term "prodrugs" as employed herein includes esters and carbonates formed by reacting one or more hydroxyls of compounds of Formula I, Ia or Ib with alkyl, alkoxy or aryl substituted acylating agents employing procedures known to those skilled in the art to generate acetates, pivalates, methylcarbonates, benzoates, and the like.

Various forms of prodrugs are well known in the art and are described in:

a) Wermuth, C. G. et al., *The Practice of Medicinal Chemistry*, Chapter 31, Academic Press (1996);

b) *Design of Prodrugs*, H. Bundgaard, ed., Elsevier (1985);

c) Bundgaard, H., Chapter 5, "Design and Application of Prodrugs," *A Textbook of Drug Design and Development*, pp. 113-191, P. Krosgaard-Larsen et al., eds., Harwood Academic Publishers (1991); and d) Testa, B. et al., *Hydrolysis in Drug and Prodrug Metabolism*, Wiley-VCH (2003).

Said references are incorporated herein by reference, particularly as to the description of prodrugs.

In addition, compounds of Formula I, Ia, or Ib are, subsequent to their preparation, preferably isolated and purified to obtain a composition containing an amount by weight equal to or greater than 99% of a compound of Formula I, Ia or Ib ("substantially pure" compound), which is then used or formulated as described herein. Such "substantially pure" compounds of Formula I, Ia or Ib are also contemplated herein as part of the present invention.

All stereoisomers of the compounds of the instant invention are contemplated, either in admixture or in pure or substantially pure form. The compounds of the present invention can have asymmetric centers at any of the carbon atoms including any one of the R substituents and/or exhibit polymorphism. Consequently, compounds of Formula I, Ia or Ib can exist in enantiomeric, or diastereomeric forms, or in mixtures thereof. The processes for preparation can utilize racemates, enantiomers, or diastereomers as starting materials. When diastereomeric or enantiomeric products are prepared, they can be separated by conventional methods for example, chromatographic or fractional crystallization.

The invention also includes isotopically-labeled compounds of the invention, wherein one or more atoms is replaced by an atom having the same atomic number, but an atomic mass or mass number different from the atomic mass or mass number usually found in nature. Examples of isotopes suitable for inclusion in the compounds of the invention include isotopes of hydrogen, such as $^2H$ and $^3H$, carbon such as $^{11}C$, $^{13}C$, and $^{14}C$, chlorine, such as $^{36}Cl$, fluorine such as $^{18}F$, iodine, such as $^{123}I$ and $^{125}I$ nitrogen, such as $^{13}N$ and $^{15}N$, oxygen, such as $^{15}O$, $^{17}O$, and $^{18}O$, phosphorus, such as $^{32}P$, and sulfur, such as $^{35}S$. Certain isotopically-labeled compounds of the invention, for example, those incorporating a radioactive isotope, are useful in drug and/or substrate tissue distribution studies. The radioactive isotopes tritium, $^3H$, and carbon-14, $^{14}C$, are particularly useful for this purpose in view of their ease of incorporation and ready means of detection. Substitution with heavier isotopes such as deuterium, $^2H$, may afford certain therapeutic advantages resulting from greater metabolic stability, for example, increase in vivo half-life or reduced dosage requirements, and hence may be preferred in some circumstances. Substitution with positron emitting isotopes, such as $^{11}C$, $^{18}F$, $^{15}O$, and $^{13}N$, can be useful in Positron Emission Topography (PET) studies for examining substrate receptor occupancy.

Isotopically-labeled compounds of the invention can generally be prepared by conventional techniques known to those skilled in the art or by processes analogous to those described herein, using an appropriate isotopically-labeled reagent in place of the non-labeled reagent otherwise employed.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to modulate GPR119 or effective to treat or prevent various disorders.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) modulating the disease-state, i.e., arresting it development; and/or (c) relieving the disease-state, i.e., causing regression of the disease state.

Synthesis

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereof as appreciated by those skilled in the art. Preferred methods include, but are not limited to, those described below. All references cited herein are hereby incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

The following are the definitions of symbols used throughout Schemes 1 to 7: P* is a suitable nitrogen or oxygen protecting group, exemplified by benzyl, t-butoxycarbonyl-[BOC], benzyloxycarbonyl-[CBZ], or t-butyl groups; X is a leaving group exemplified by halogen (Cl, Br, I) and OTf.

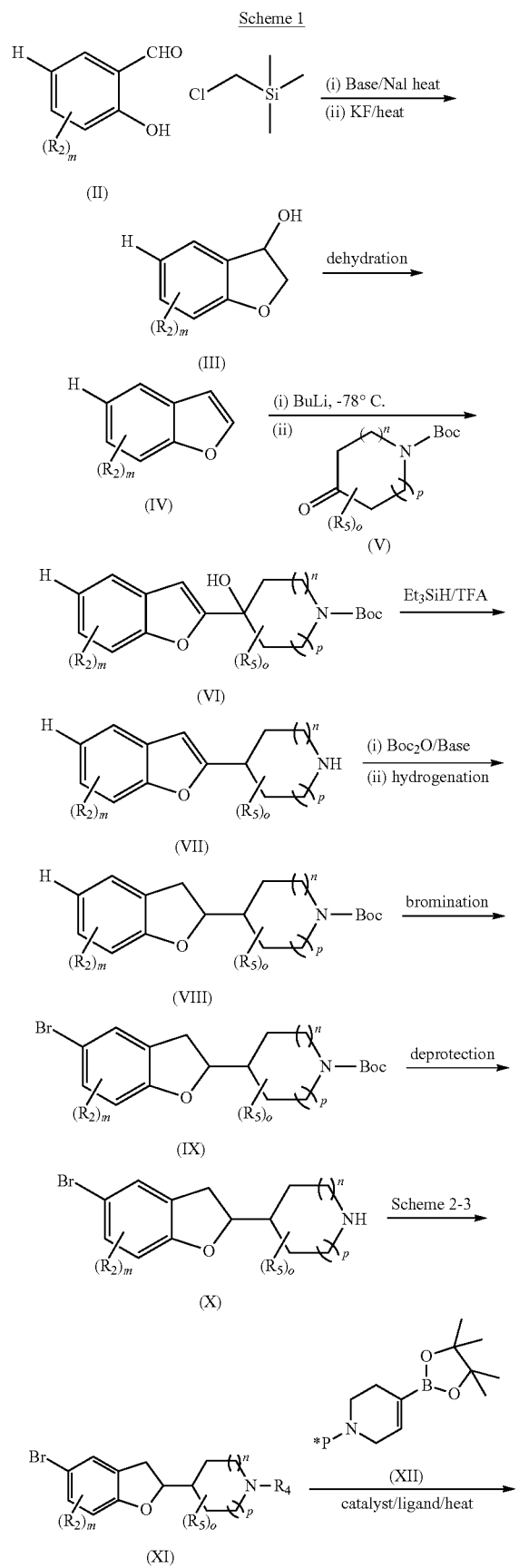

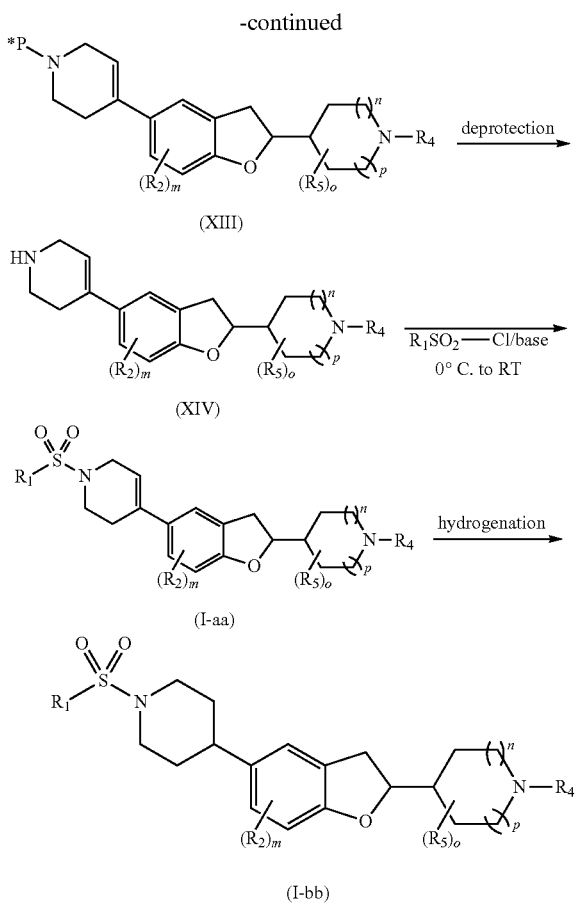

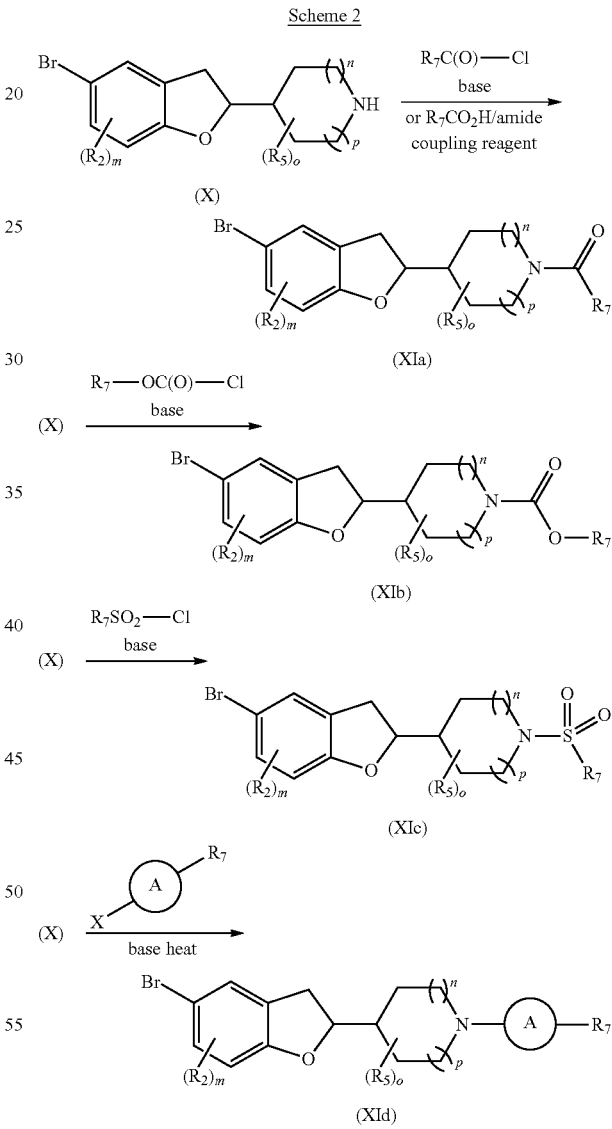

Pd(OAc)$_2$, Pd$_2$(dba)$_3$ and a suitable ligand such as PPh$_3$, AsPh$_3$, etc., or other such Pd(0) catalyst, and a base such as Na$_2$CO$_3$, K$_2$CO$_3$, Ba(OH)$_2$ or Et$_3$N in a suitable solvent such as DMF, toluene, THF, DME, 1,4-dioxane or the like, to afford XIII. The protecting group of XIII can be removed by appropriate methods well known to those skilled in the art to give secondary amine XIV, which further reacts with sulfonyl chloride R$_1$SO$_2$Cl (commercially available or can be prepared by the methods known to one skilled in the art) in the presence of base such as Et$_3$N affords sulfonamide I-aa. Compounds I-bb can be produced by reduction of I-aa under H$_2$ atmosphere with appropriate catalysts, such as Pd/C, by a number of conditions that are routine for those skilled in the art of organic synthesis.

Scheme 1 describes a method of preparing compounds of formula I-aa and I-bb (subsets of compounds of formula I). Substituted 2-hydroxybenzaldehyde II (commercially available or prepared by methods known to one skilled in the art) can be reacted with chloromethyl trimethylsilane in the presence of base (such as K$_2$CO$_3$) and NaI to afford alkylation product, which can be cyclized to III upon heating with KF. III can be dehydrated using dehydrating agent such as sulfuryl chloride or thionyl chloride to afford substituted benzofuran IV. Deprotonation at the 2-position of IV using base such as BuLi, followed by reaction with appropriate N-protected ketone V affords VI. The transformation of VI to VIII can be achieved through reduction and protecting group manipulation (all known in literature or known to one skilled in the art). For example, Et$_3$SiH/TFA can be used to remove the benzylic hydroxy group, while Pd—C/H$_2$ can be used to reduce the double bond to form the dihydrobenzofuran. Bromination of VIII can take place in Br$_2$/CHCl$_3$ or NBS/HOAc to afford IX. The deprotection of Boc-group can be achieved in TFA/CH$_2$Cl$_2$ or HCl in dioxane to afford secondary amine X. The installation of R$_4$ group on N can be achieved using the procedure depicted in Scheme 2-3. Boronic acids or borates XII with an appropriate protecting group on nitrogen (commercially available or can be prepared), can be coupled with intermediates XI via Suzuki coupling protocol. For a review and leading references of palladium catalyzed cross coupling reactions, see: (a) Miyaura, N. et al., *Chem. Rev.*, 2457 (1995); (b) Yin, L. et al., *Chem. Rev.*, 107(1):133-173 (2007). One such procedure entails treatment of the aryl bromide XI with a functionalized vinyl boronic acids in the presence of a catalytic Pd(0) species, such as Pd(PPh$_3$)$_4$, Pd(PPh$_3$)$_2$Cl$_2$, Scheme 2 describes a method of preparing intermediates XIa-XId for Suzuki coupling reaction used in Scheme 1. For example, X can react R$_7$—C(O)—Cl or R$_7$CO$_2$H (commercially available or prepared by methods known to one skilled in the art) to form amide XIa. X can react with chloroformate $R_7OC(O)$—Cl (commercially available or prepared by methods known to one skilled in the art) to form carbamate XIb. X can also react with a sulfonyl chloride $R_7SO_2Cl$ (commercially available or prepared by the methods known to one skilled in the art), in the presence of base such as $Et_3N$ to afford sulfonamide XIc. Furthermore, X can react with 5- or 6-membered ring heteroaryl halides via displacement or via metal catalyzed N-arylation reaction reported in literature or other methods known to one skilled in the art to afford XId.

vent such as xylene at an elevated temperature such as reflux, desired thiazole XIf can be obtained. In another approach, X can react with cyanogen bromide in a suitable solvent such as aqueous $Na_2CO_3$ and dichloromethane to form XIg, which can be converted to XIh by treating with hydroxylamine in an appropriate solvent such as ethanol at elevated temperature such as 60° C. Intermediate XIh can be reacted with $R_8$-AE (wherein AE stands for a functional group selected from —$CO_2H$, —$CO_2R'$, etc) using any of the protocols known in the literature (references for such transformation include *Tetrahedron Lett.*, 47:3629 (2006), and *J. Med. Chem.*, 47:5821

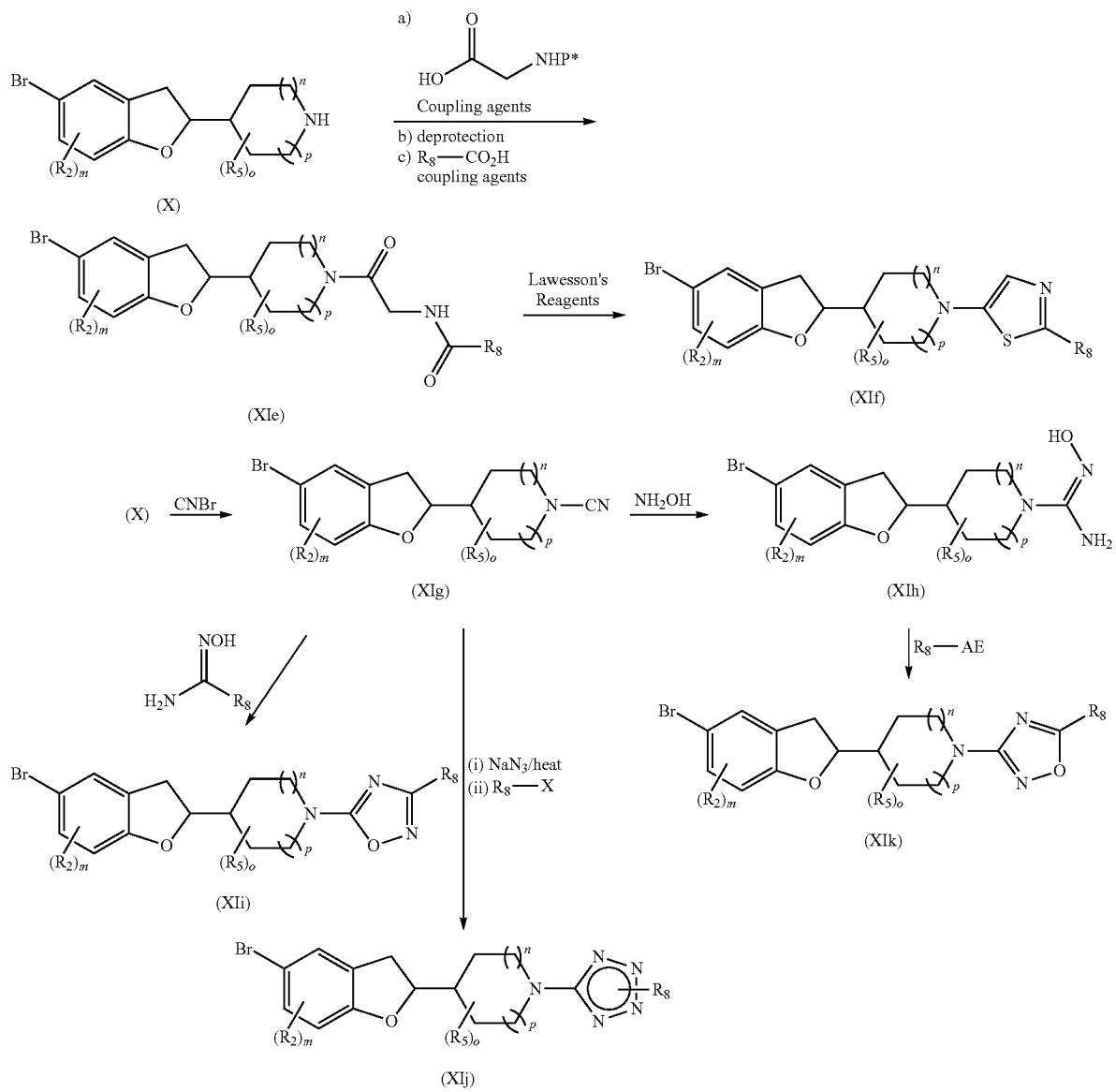

Scheme 3 describes a method of preparing intermediates XIe-XIj for Suzuki coupling reaction used in Scheme 1. For example, X can be converted to XIe through three-step reaction sequences including amide coupling and deprotection of amine protecting group both of which are known to one skilled in the art. Upon treating with Lawesson's reagent or other thiotransfer/dehydrating agents in an appropriate solvent (2004), but does not exclude others known to one skilled in the art) to afford XIk. Intermediate XIg can also be reacted with $R_8(NH_2)C$=NOH (commercially available or prepared by methods known to one skilled in the art) in the presence of a Lewis acid (such as $ZnCl_2$) at certain temperature (such as reflux) to afford XIi. Intermediate Mg can also be reacted with $NaN_3$ at elevated temperature (such as reflux) to form a tetrazole, which can be further converted to XIj via standard alkylation reaction with $R_8$—X (where X is leaving group such as Cl, Br, I, etc).

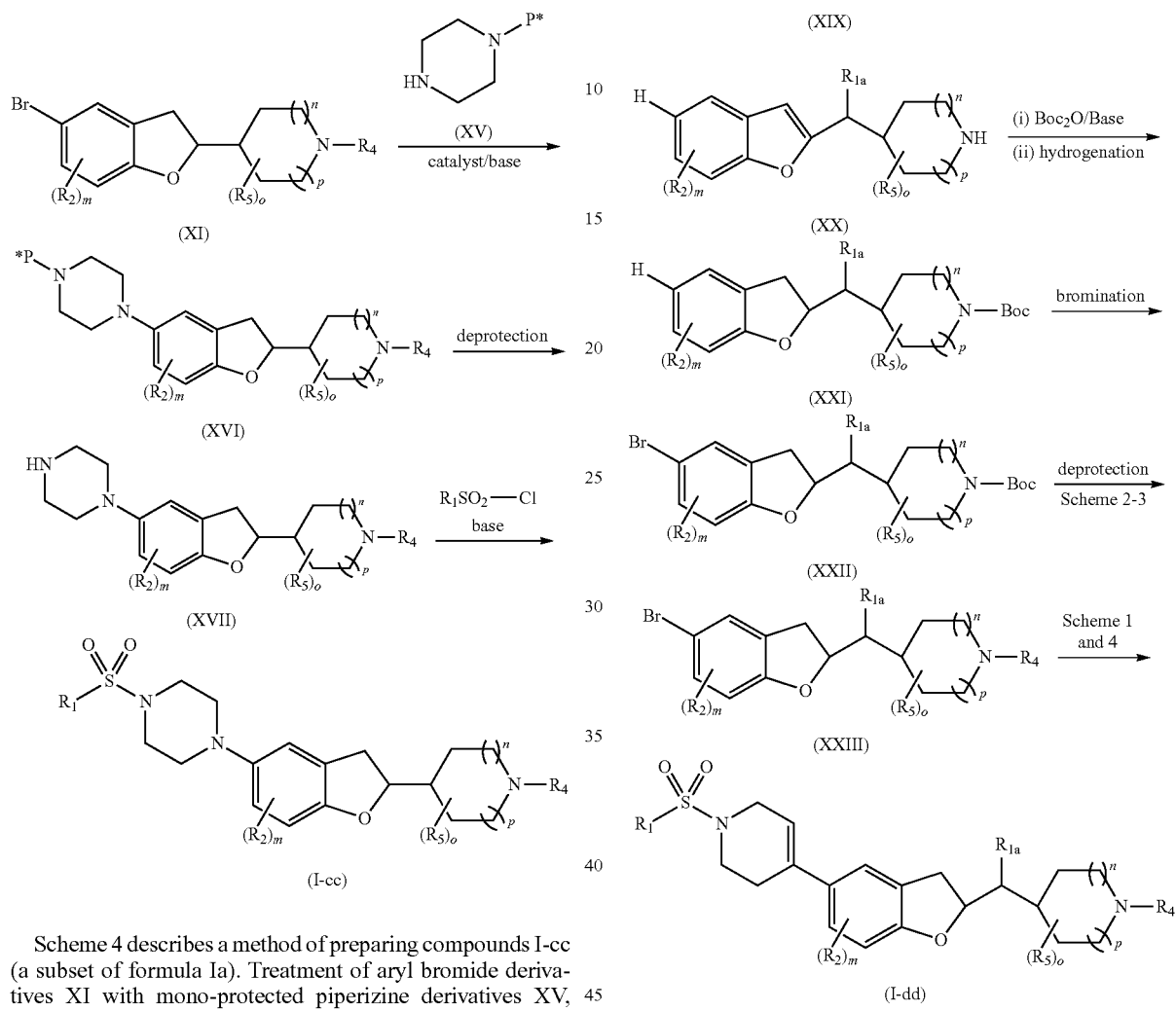

Scheme 4 describes a method of preparing compounds I-cc (a subset of formula Ia). Treatment of aryl bromide derivatives XI with mono-protected piperizine derivatives XV, which are commercially available or can be prepared by many methods known in the art, in the presence of a Pd(0) catalyst, such as $Pd_2(dba)_3$, $Pd(PPh_3)_4$ or $Pd(PPh_3)_2Cl_2$, and suitable ligand such BINAP or $PPh_3$, and a base such as t-BuONa or $Cs_2CO_3$ in a suitable solvent such as DMF, toluene, THF, DME, or the like, affords XVI. Intermediate XVI can then be deprotected to form XVII, which can be further converted to I-cc by following the procedure described in Scheme 1.

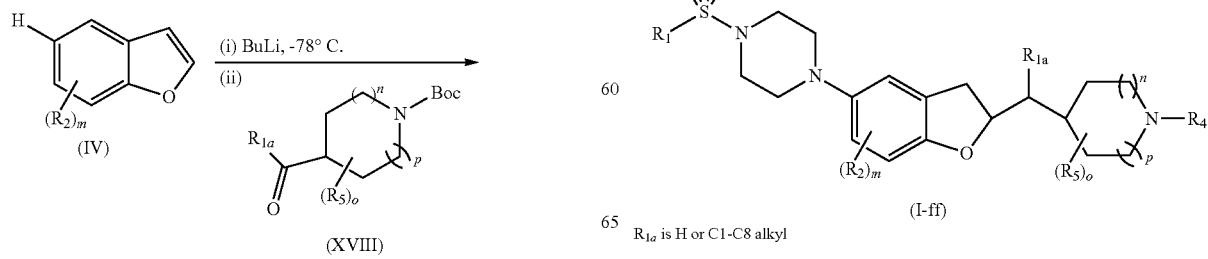

$R_{1a}$ is H or C1-C8 alkyl

Scheme 5 describes a method of preparing compounds I-dd, I-ee, and I-ff (subsets of formula Ia). The reaction sequences have been adapted from Scheme 1 except using different ketone or aldehyde XVIII to replace V. By following Scheme 1 and Scheme 4, I-dd, I-ee, and I-ff can be prepared by one skilled in the art.

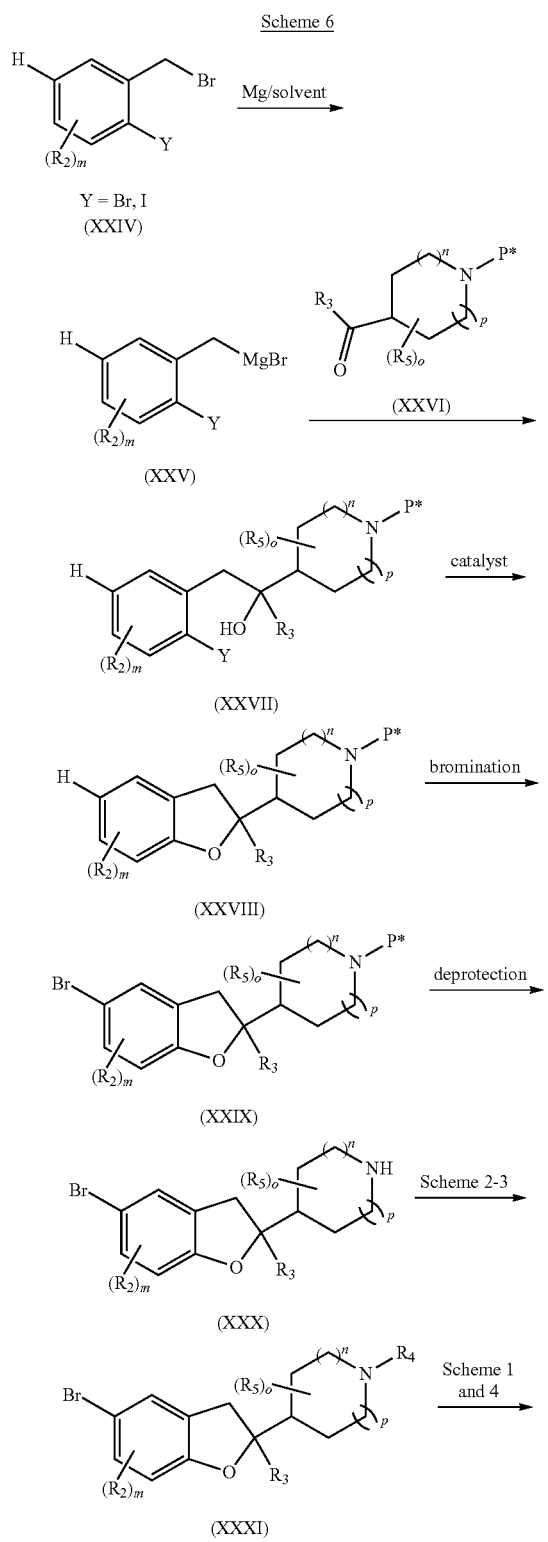

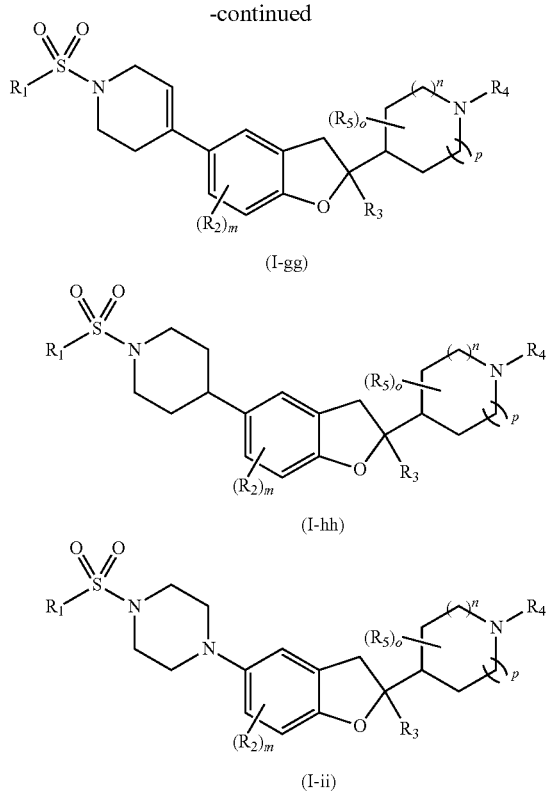

Scheme 6 describes a method of preparing compounds I-gg, I-hh, and I-ii (subsets of compounds of formula I). Grignard reagent XXV, obtained from substituted benzyl bromide XXIV (commercially available or prepared by the methods known to one skilled in the art) and magnesium, can react with ketone XXVI to form tertiary alcohol XXVII. The Ullmann type ether formation of XXVII can be catalyzed by transition metal such as Pd and Cu with appropriate ligand in elevated temperature (this type reaction has been extensively studied in literature, see: *J. Org. Chem.*, 74(14):5075-5078 (2009) and the references cited therein) to afford XXVIII. The transformation of XXVIII to I-gg, I-hh, and I-ii can be achieved using the procedure depicted in Schemes 1-4.

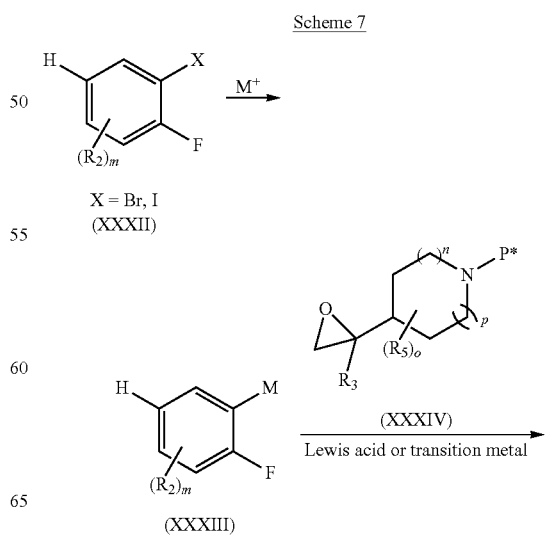

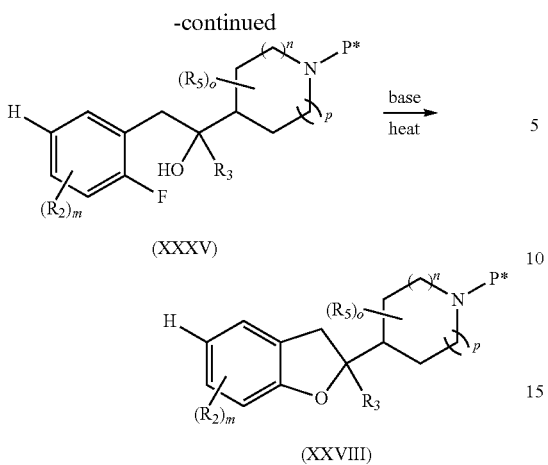

(XXXV)

(XXVIII)

Scheme 7 describes an alternative method of preparing the intermediates XXVIII used in Scheme 6. Metallation of XXXII with M+ such as BuLi or i-PrMgBr affords XXXIII in situ, which can be subjected to epoxide ring opening with XXXIV (commercially available or prepared by the method known to one skilled in the art) in the presence of Lewis acid such as $BF_3$ etherate or a transition metal such as $Cu_2S$ to afford XXXV. Upon heating XXXV with base such as KH or NaH, intermediates XXVIII can be obtained.

Abbreviations

The following abbreviations are employed in the Examples and elsewhere herein: $Ac_2O$=acetic anhydride; AcOH=acetic acid; BINAP=rac-2,2'-bis(diphenylphosphino)-1,1'-binaphthyl; BOC=tert-butoxycarbonyl; $Boc_2O$=di-tert-butyl dicarbonate; $Br_2$=bromine; CBZ=benzyloxycarbonyl; $CDCl_3$=chloroform-d; $CH_2Cl_2$=methylene chloride; $CHCl_3$=chloroform; $Cs_2CO_3$=cesium carbonate; Cs=cesium fluoride; DAST=diethylaminosulfur trifluoride; DEAD=diethyl azodicarboxylate; DIEA=diisopropylethylamine; DME=dimethoxyethane; DMF=N,N-dimethylformamide; DMSO=dimethyl sulfoxide; EtOAc=ethyl acetate; EtOH=ethanol; $Et_3N$=triethylamine; $Et_2O$=diethyl ether; $Et_3SiH$=triethylsilane; HPLC or LC=high performance liquid chromatography; $I_2$=iodine; $K_2CO_3$=potassium carbonate; KH=potassium hydride; KOH=potassium hydroxide; $LiAlH_4$ (or LAH)=lithium aluminum hydride; mCPBA=m-chloroperoxybenzoic acid; MeOH=methanol; $MgSO_4$=magnesium sulfate; MS or Mass Spec=mass spectrometry; NaCl=sodium chloride; NaH=sodium hydride; $NaHCO_3$=sodium bicarbonate; NaI=sodium iodide; $Na_2SO_4$=sodium sulfate; $Na_2CO_3$=sodium carbonate; NaOH=sodium hydroxide; $Na_2H_2S_2O_5$=sodium metabisulfite; NBS=N-bromosuccinimide; Pd—C=palladium(0) on carbon; $Pd_2(dba)_3$=tris(dibenzylideneacetone)dipalladium (0); $Pd(Ph_3P)_4$=tetrakis(triphenylphosphine)palladium (0); $Pd(dppf)Cl_2$=[1,1'-bis(diphenylphosphino)-ferrocene]dichloropalladium(II); $Pd(OAc)_2$=palladium(II) acetate; $Ph_3PCl_2$=triphenylphosphine dichloride; P*=protecting group; $POCl_3$=phosphorus oxychloride; t-BuONa=sodium tert-butoxide; TFA=trifluoroacetic acid; THF=tetrahydrofuran; $SOCl_2$=thionyl chloride; min=minute(s); h or hr=hour(s); L=liter(s); mL or ml=milliliter(s); μL or μl=microliter(s); g or gm=gram(s); mg=milligram(s); mol=moles; mmol=millimole(s); M=molar; nM=nanomolar; [M+H]=parent plus a proton; rt=room temperature; MS=low resolution mass spectrometry; and NMR=nuclear magnetic resonance.

EXAMPLE 1

4-(7-Fluoro-5-(1-(propylsulfonyl)-1,2,3,6-tetrahydropyridin-4-yl)-2,3-dihydrobenzofuran-2-yl)-1-(5-propylpyrimidin-2-yl)piperidin-4-ol

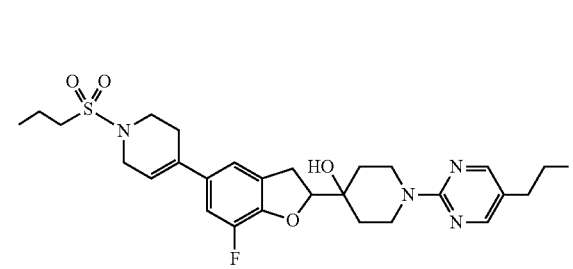 [SMILES: CCCc1cnc(N2CCC(O)(C3Cc4cc(C5=CCN(S(=O)(=O)CCC)CC5)cc(F)c4O3)CC2)nc1]

Compound 1A.
3-Fluoro-2-((trimethylsilyl)methoxy)benzaldehyde

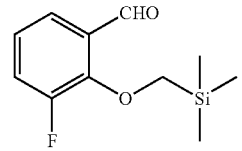

To a suspension of 3-fluoro-2-hydroxybenzaldehyde (4.18 g, 29.8 mmol) and $K_2CO_3$ (12.25 g, 89 mmol) in DMF (81 mL) was added (chloromethyl)trimethylsilane (4.06 g, 33.1 mmol) and NaI (4.96 g, 33.1 mmol). Upon completion of addition, the mixture was heated in 65° C. oil bath overnight. After this time, the mixture was cooled to rt, quenched with water (20 mL) and then extracted with $Et_2O$ (2×30 mL). The combined organic layers were washed with $H_2O$ (2×15 mL), dried ($Na_2SO_4$), filtered and concentrated to afford Compound 1A as a light yellow oil (6.7 g, 98% yield). $^1H$ NMR (500 MHz, $CDCl_3$) δ ppm 10.41 (s, 1 H), 7.60 (dd, J=9.1, 1.7 Hz, 1 H), 7.32 (ddd, J=11.8, 8.3, 1.7 Hz, 1 H), 7.01-7.12 (m, 1 H,) 4.01 (d, J=1.7 Hz, 2 H), 0.17-0.21 (m, 9 H). $^{19}F$ NMR (471 MHz, $CDCl_3$) δ ppm −129.13.

Compound 1B. 7-Fluoro-2,3-dihydrobenzofuran-3-ol

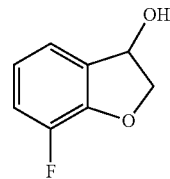 [SMILES: OC1COc2c(F)cccc21]

A mixture of 3-fluoro-2-((trimethylsilyl)methoxy)benzaldehyde (6.75 g, 29.8 mmol) and CsF (13.73 g, 90 mmol) in DMF (88 mL) were heated in 95° C. oil bath for 3 days. At the conclusion of this period, the reaction was analyzed by HPLC, which showed the starting material had disappeared. The reaction mixture was cooled to rt, diluted with aqueous NaHCO$_3$ and extracted with Et$_2$O (3×15 mL), followed by EtOAc (3×15 mL). The combined organic layers were washed with water (25 mL), brine (25 mL), dried (MgSO$_4$), and concentrated to afford Compound 1B as a brown oil (4.6 g). The crude product was used in next step without further purification.

Compound 1C. 7-Fluorobenzofuran

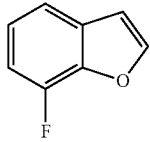

To a solution of 7-fluoro-2,3-dihydrobenzofuran-3-ol (4.6 g, 29 8 mmol) in pyridine (93 mL) at 0° C. was added SOCl$_2$ (21.7 mL, 298 mmol) dropwise. Upon completion of addition, the mixture was stirred at 0° C. for 1.5 h. At the conclusion of this period, the reaction mixture was carefully quenched with aqueous NaHCO$_3$ (saturated, 100 mL) to reach a pH=9. Once at the prescribed pH, the reaction mixture was extracted with CH$_2$Cl$_2$ (4×15 mL). The combined organic layers were washed with aqueous NaHCO$_3$ (5%, 40 mL), water (40 mL), and then concentrated to yield the crude product. The crude product was dissolved in CH$_2$Cl$_2$ (50 mL), washed with aqueous HCl (1 N, 5×10 mL), and then water (40 mL). The organic layer was separated, dried (MgSO$_4$), filtered, and concentrated to afford Compound 1C as a brown oil (2.56 g). $^1$H NMR (500 MHz, CDCl$_3$) δ ppm 7.67 (d, J=2.2 Hz, 1 H), 7.33-7.40 (m, 1 H), 7.17 (td, J=8.0, 4.4 Hz, 1 H), 7.04 (dd, J=10.7, 8.0 Hz, 1 H), 6.79-6.85 (m, 1 H).

Compound 1D. tert-Butyl 4-(7-fluorobenzofuran-2-yl)-4-hydroxypiperidine-1-carboxylate

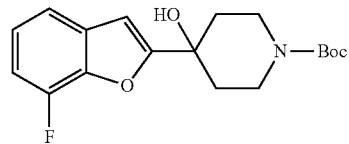 [SMILES: CC(C)(C)OC(=O)N1CCC(O)(c2cc3cccc(F)c3o2)CC1]

To a solution of 7-fluorobenzofuran (0.3 g, 1.807 mmol) in dry THF (4.8 mL) at −78° C. under an argon atmosphere was slowly added BuLi (1.3 mL, 2.078 mmol). Upon completion of addition, the mixture was stirred at −78° C. for 20 min. After this time, a solution of tert-butyl 4-oxopiperidine-1-carboxylate (0.36 g, 1.807 mmol) in THF (2.4 mL) was slowly added. The reaction mixture was warmed to −40° C., where it stirred for 2 hrs. At the conclusion of this period, the reaction mixture was quenched with aqueous NH$_4$Cl (saturated, 5 mL) and then extracted with EtOAc (3×5 mL). The combined organic layers were washed with H$_2$O (2×4 mL), brine (5 mL), dried (Na$_2$SO$_4$), filtered, and concentrated to yield a residue. The residue was purified by column chromatography (silica gel, hexanes/EtOAc gradient 0 to 60% EtOAc) to afford Compound 1D as a white solid (530 mg, 94.7% purity, 83% yield).
$^1$H NMR (400 MHz, CDCl$_3$) δ ppm 7.30 (dd, J=7.8, 1.0 Hz, 1 H), 7.14 (td, J=7.9, 4.4 Hz, 1 H), 6.96-7.07 (m, 1 H), 6.64 (d, J=2.8 Hz, 1 H), 3.86 (br. s., 2 H), 3.39 (t, J=11.1 Hz, 2 H), 2.44 (t, J=6.2 Hz, 1 H), 2.08-2.21 (m, 2 H), 1.90-2.02 (m, 2 H), 1.44-1.50 (m, 9 H). LC/MS (m/z)=336 (M+H)$^+$.

Compound 1E. tert-Butyl 4-(7-fluoro-2,3-dihydrobenzofuran-2-yl)-4-hydroxypiperidine-1-carboxylate

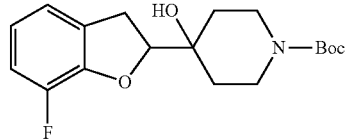 [SMILES: CC(C)(C)OC(=O)N1CCC(O)(C2Cc3cccc(F)c3O2)CC1]

To a degassed solution of tert-butyl 4-(7-fluorobenzofuran-2-yl)-4-hydroxypiperidine-1-carboxylate (0.52 g, 1.55 mmol) in EtOH (9.62 mL) was added 10% Pd—C (0.495 g, 0.465 mmol). Upon completion of addition, the reaction mixture was charged with 55 psi of H$_2$ overnight. After the conclusion of this period, the Pd—C was filtered off through a pad of CELITE®, and the filter cake was rinsed with EtOH. The solvent was removed under reduced pressure to afford Compound 1E as a light yellow solid (0.404 g, 77% yield).

Compound 1F. 4-(7-Fluoro-2,3-dihydrobenzofuran-2-yl)piperidin-4-ol hydrochloride

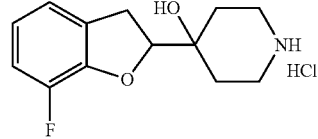 [SMILES: OC1(C2Cc3cccc(F)c3O2)CCNCC1 ; Cl]

To a solution of tert-butyl 4-(7-fluoro-2,3-dihydrobenzofuran-2-yl)-4-hydroxypiperidine-1-carboxylate (0.404 g, 1.197 mmol) in MeOH (7.04 mL) was added HCl in dioxane (4 M, 4.4 mL, 17.48 mmol). Upon completion of addition, the reaction mixture was stirred at room temperature for 5 hours. After this time, the solvent was removed under reduced pressure to afford Compound 1F as a light yellow solid (0.38 g, 100% yield). LC/MS (m/z)=238 (M+H)$^+$.

Compound 1G. 4-(5-Bromo-7-fluoro-2,3-dihydrobenzofuran-2-yl)piperidin-4-ol

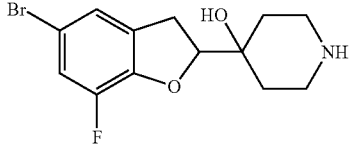 [SMILES: OC1(C2Cc3cc(Br)cc(F)c3O2)CCNCC1]

To a solution of 4-(7-fluoro-2,3-dihydrobenzofuran-2-yl)piperidin-4-ol hydrochloride (380 mg, 1.388 mmol) in MeOH (11.1 mL) at 0° C. was added NBS (235 mg, 1.319 mmol) in one portion. Upon completion of addition, the reaction mixture was stirred at room temperature for 3 hours, and then quenched with aqueous Na$_2$H$_2$S$_2$O$_5$ (10%, 5 mL). The solvent was removed under reduced pressure to yield a residue. The residue was diluted with CH$_2$Cl$_2$ (5 mL), washed with aqueous NaOH (1 N, 3 mL) and brine (3 mL). The organic layer was separated, dried (K₂CO₃), filtered, and concentrated to afford Compound 1G as a white solid (0.168 g, 38% yield). LC/MS (m/z)=317 (M+H)⁺.

Compound 1H. 4-(5-Bromo-7-fluoro-2,3-dihydrobenzofuran-2-yl)-1-(5-propylpyrimidin-2-yl)piperidin-4-ol

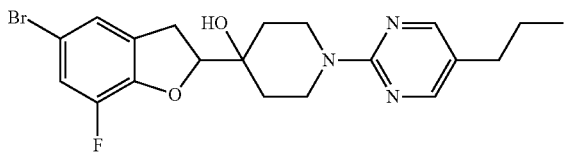 [SMILES: CCCc1cnc(N2CCC(O)(C3Cc4cc(Br)cc(F)c4O3)CC2)nc1]

A mixture of 4-(5-bromo-7-fluoro-2,3-dihydrobenzofuran-2-yl)piperidin-4-ol (0.17 g, 0.531 mmol), 2-chloro-5-propylpyrimidine (0.11 g, 0.691 mmol) and K₂CO₃ (0.22 g, 1.594 mmol) in DMF (2.6 mL) were heated in 90° C. oil bath for 10 hours. At the conclusion of this period, the reaction mixture was cooled to room temperature, quenched with H₂O (5 mL), and then extracted with EtOAc (3×5 mL). The combined organic layers were washed with H₂O (3×5 mL) and brine (5 mL), dried (Na₂SO₄), filtered, and concentrated to yield a residue. The residue was purified by column chromatography (silica gel, hexanes/EtOAc gradient 30 to 40% EtOAc) to afford Compound 1H as a light yellow solid (0.122 g, 52.6% yield). $^1$H NMR (400 MHz, CDCl₃) δ ppm 8.14 (s, 2 H), 6.99-7.10 (m, 2 H), 4.67 (t, J=9.2 Hz, 1 H), 4.47-4.62 (m, 2 H), 3.23-3.41 (m, 3 H), 3.10 (dd, J=15.8, 9.2 Hz, 1 H), 2.39 (t, J=7.6 Hz, 2 H), 1.84-2.00 (m, 2 H), 1.74 (td, J=13.1, 4.8 Hz, 1 H), 1.46-1.66 (m, 4 H), 0.93 (t, J=7.3 Hz, 3 H). LC/MS (m/z)=437 (M+H)⁺.

Compound 1I. tert-Butyl 4-(7-fluoro-2-(4-hydroxy-1-(5-propylpyrimidin-2-yl)piperidin-4-yl)-2,3-dihydrobenzofuran-5-yl)-5,6-dihydropyridine-1(2H)-carboxylate

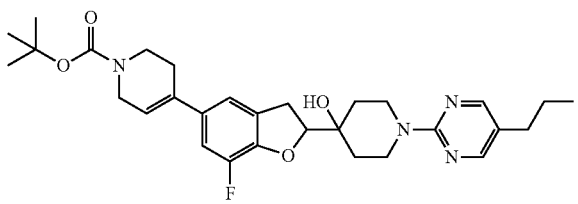 [SMILES: CCCc1cnc(N2CCC(O)(C3Cc4cc(C5=CCN(C(=O)OC(C)(C)C)CC5)cc(F)c4O3)CC2)nc1]

To a degassed solution of 4-(5-bromo-7-fluoro-2,3-dihydrobenzofuran-2-yl)-1-(5-propylpyrimidin-2-yl)piperidin-4-ol (0.122 g, 0.280 mmol), tert-butyl 4-(4,4,5,5-tetramethyl-1,3,2-dioxaborolan-2-yl)-5,6-dihydropyridine-1(2H)-carboxylate (0.112 g, 0.363 mmol), and K₂CO₃ (97 mg, 0.699 mmol) in dioxane (2.9 mL) and H₂O (1 mL) was added Pd(Ph₃P)₄ (16 mg, 0.014 mmol). Upon completion of addition, the reaction mixture was stirred at 100° C. for 15 hour under argon. At the conclusion of this period, the reaction mixture was cooled to room temperature and then diluted with EtOAc/Et₂O (5 mL, 1:1 v/v). The organic layer was washed with aqueous NaHCO₃ (saturated, 6 mL) and aqueous NaCl (saturated, 6 mL), dried (Na₂SO₄), filtered, and then concentrated to yield a residue. The residue was purified by column chromatography (silica gel, hexanes/EtOAc gradient 0 to 60% EtOAc) to afford Compound 1I as a light yellow solid (0.156 g, 97% yield). $^1$H NMR (500 MHz, CDCl₃) δ ppm 8.15 (s, 2 H), 6.96 (s, 1 H), 6.91 (d, J=12.1 Hz, 1 H), 5.90 (br. s., 1 H), 4.67 (t, J=9.1 Hz, 1 H), 4.50-4.63 (m, 2 H), 4.03 (d, J=2.8 Hz, 2 H), 3.60 (t, J=5.6 Hz, 2 H), 3.26-3.40 (m, 3 H), 3.11 (dd, J=15.7, 9.1 Hz, 1 H), 2.33-2.48 (m, 4H), 1.92-2.00 (m, 2 H), 1.68-1.81 (m, 1 H), 1.52-1.67 (m, 4 H), 1.44-1.52 (m, 9H), 0.90-0.97 (t, J=7.3 Hz, 3 H). LC/MS (m/z)=539 (M+H)⁺.

Compound 1J. 4-(7-Fluoro-5-(1,2,3,6-tetrahydropyridin-4-yl)-2,3-dihydrobenzofuran-2-yl)-1-(5-propylpyrimidin-2-yl)piperidin-4-ol

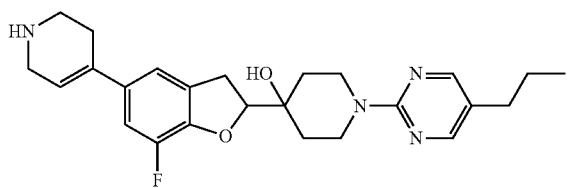 [SMILES: CCCc1cnc(N2CCC(O)(C3Cc4cc(C5=CCNCC5)cc(F)c4O3)CC2)nc1]

To a solution of tert-butyl 4-(7-fluoro-2-(4-hydroxy-1-(5-propylpyrimidin-2-yl)piperidin-4-yl)-2,3-dihydrobenzofuran-5-yl)-5,6-dihydropyridine-1(2H)-carboxylate (0.15 g, 0.278 mmol) in CH₂Cl₂ (2.3 mL) was added TFA (1.5 mL, 19.49 mmol). Upon completion of addition, the reaction mixture was stirred at room temperature for 1 hour. After this time, the solvent was removed to yield a residue. The residue was diluted with CH₂Cl₂ (4 mL), washed with aqueous NaHCO₃ (saturated, 3 mL), dried (Na₂SO₄), filtered, and concentrated to afford crude Compound 1J, which was used in next reaction without further purification. LC/MS (m/z)=439 (M+H)⁺.

EXAMPLE 1

To a solution of 4-(7-fluoro-5-(1,2,3,6-tetrahydropyridin-4-yl)-2,3-dihydrobenzofuran-2-yl)-1-(5-propylpyrimidin-2-yl)piperidin-4-ol (41 mg, 0.093 mmol) in CH₂Cl₂ (1.8 mL) at 0° C. was added Et₃N (52 μL, 0.374 mmol) followed by a slow addition of propane-1-sulfonyl chloride (10 μL, 0.09 mmol). Upon completion of addition, the reaction mixture was stirred at 0° C. for an additional 2 hours. At the conclusion of this period, the reaction mixture was quenched with H₂O (0.3 mL) and then extracted with CH₂Cl₂ (3×1 mL). The combined organic layers were dried (Na₂SO₄), filtered, and concentrated to yield a residue. The residue was purified by column chromatography (silica gel, hexanes/EtOAc gradient 0 to 80% EtOAc) to afford Example 1 as a light yellow solid (39.8 mg, 78% yield). $^1$H NMR (400 MHz, DMSO-d₆) δ ppm 8.19 (s, 2 H), 7.13 (s, 1 H), 7.09 (d, J=12.6 Hz, 1 H), 6.09 (s, 1 H), 4.80 (s, 1 H), 4.69 (t, J=8.8 Hz, 1 H), 4.42 (d, J=12.6 Hz, 2 H), 4.09 (t, J=5.2 Hz, 1H), 3.85 (d, J=2.7 Hz, 2 H), 3.24-3.46 (m, 3 H), 3.09-3.24 (m, 4 H), 2.99-3.09 (m, 2 H), 2.42-2.62 (m, 1 H), 2.28-2.40 (m, 2 H), 1.61-1.79 (m, 3 H), 1.37-1.59 (m, 5 H), 0.98 (t, J=7.4 Hz, 3 H), 0.76-0.90 (m, 3 H). LC/MS (m/z)=545 (M+H)⁺.

EXAMPLE 2

2-(4-fluoro-4-(7-fluoro-5-(1-(propylsulfonyl)-1,2,3,6-tetrahydropyridin-4-yl)-2,3-dihydrobenzofuran-2-yl)piperidin-1-yl)-5-propylpyrimidine

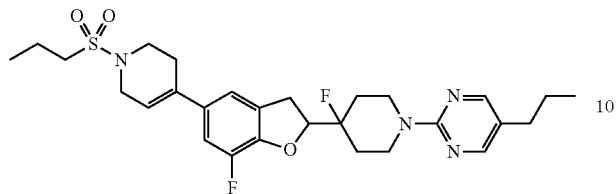

To a solution of 4-(7-fluoro-5-(1-(propylsulfonyl)-1,2,3,6-tetrahydropyridin-4-yl)-2,3-dihydrobenzofuran-2-yl)-1-(5-propylpyrimidin-2-yl)piperidin-4-ol (28.7 mg, 0.053 mmol) in $CH_2Cl_2$ (1 mL) at 0° C. was added DAST (7.7 μL, 0.058 mmol). Upon completion of addition, the reaction mixture was stirred at 0° C. for 2 hours. After this time, the reaction mixture was quenched with aqueous $NaHCO_3$ (saturated, 2 mL) and then extracted with $CH_2Cl_2$ (2×2 mL). The combined organic layers were dried ($Na_2SO_4$), filtered, and concentrated to yield a residue. The residue was purified by column chromatography (silica gel, hexanes/EtOAc gradient 0 to 70% EtOAc) to afford Example 2 as a white solid (18 mg, >90% purity, 62.5% yield). $^1$H NMR (400 MHz, DMSO-$d_6$) δ ppm 8.23 (s, 2 H), 7.06-7.17 (m, 2 H), 6.10 (s, 1 H), 4.83-5.04 (m, 1 H), 4.40-4.61 (m, 2 H), 3.85 (d, J=2.7 Hz, 2 H), 3.18-3.47 (m, 5 H), 2.97-3.17 (m, 4 H), 2.36 (t, J=7.7 Hz, 2 H), 2.06 (t, J=11.3 Hz, 1 H), 1.56-1.87 (m, 6 H), 1.50 (sxt, J=7.5 Hz, 2 H), 0.97 (t, J=7.4 Hz, 3 H), 0.86 (t, J=7.4 Hz, 3 H). $^{19}$F NMR (376 MHz, DMSO-$d_6$) δ ppm −139.03, −175.93. LC/MS (m/z)=547 (M+H)$^+$.

EXAMPLE 3

Methyl 4-(4-(7-fluoro-2-(1-(5-propylpyrimidin-2-yl)piperidin-4-yl)-2,3-dihydrobenzofuran-5-yl)-5,6-dihydropyridin-1(2H)-ylsulfonyl)butanoate

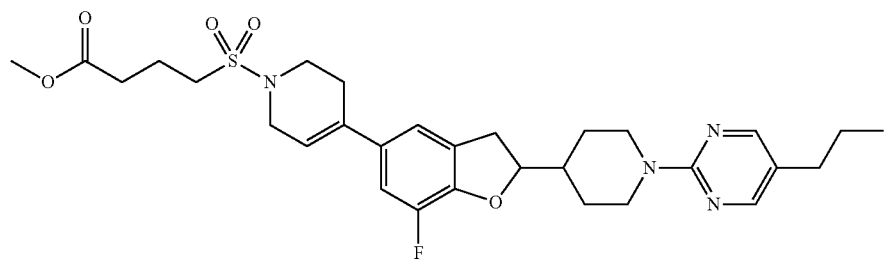 [SMILES: CCCc1cnc(N2CCC(C3Cc4cc(C5=CCN(S(=O)(=O)CCCC(=O)OC)CC5)cc(F)c4O3)CC2)nc1]

Compound 3A.
4-(7-Fluorobenzofuran-2-yl)piperidine

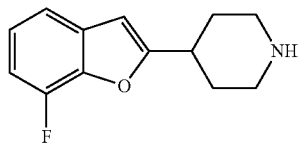 [SMILES: Fc1cccc2cc(C3CCNCC3)oc12]

To a solution of tert-butyl 4-(7-fluorobenzofuran-2-yl)-4-hydroxypiperidine-1-carboxylate (Compound 1D, 3.3 g, 9.84 mmol) in $CH_2Cl_2$ (19.68 mL) at 0° C. was added $Et_3SiH$ (6.29 mL, 39.4 mmol) followed by the slow addition of TFA (18.95 mL, 246 mmol). Upon completion of addition, the reaction mixture was stirred at 0° C. for 30 min, and then gradually warmed to room temperature overnight. Once at the prescribed temperature, the solvent was removed under reduced pressure to afford crude Compound 3A, which was used in the next reaction without further purification. LC/MS (m/z)=220 (M+H)$^+$.

Compound 3B. tert-Butyl 4-(7-fluorobenzofuran-2-yl)piperidine-1-carboxylate

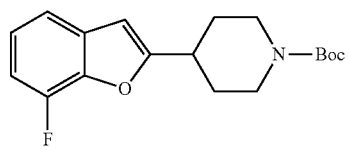 [SMILES: CC(C)(C)OC(=O)N1CCC(c2cc3cccc(F)c3o2)CC1]

To a solution of 4-(7-fluorobenzofuran-2-yl)piperidine (2.1 g, 9.58 mmol) in THF (19.2 mL) and aqueous $K_2CO_3$ (saturated, 19.2 mL) at 0° C. was added $Boc_2O$ (2.7 mL, 11.49 mmol). Upon completion of addition, the reaction mixture was gradually warmed to room temperature, where it stirred for 1 hour. After this time, the reaction mixture was extracted with $Et_2O$ (3×15 ml). The combined organic layers were washed with $H_2O$ (3×10 mL) and brine (20 mL), dried ($Na_2SO_4$), filtered, and then concentrated to yield a residue. The residue was purified by column chromatography (silica gel, hexanes/EtOAc gradient 0 to 40% EtOAc) to afford Compound 3B as a light yellow oil (2.69 g, 88% yield).

Compound 3C. tert-Butyl 4-(7-fluoro-2,3-dihydrobenzofuran-2-yl)piperidine-1-carboxylate To a degassed solution of tert-butyl 4-(7-fluorobenzofuran-2-yl)piperidine-1-carboxylate (3.4 g, 8.41 mmol) in EtOH (54.3 mL) was added 10% Pd—C (2.69 g, 2.52 mmol). Upon completion of addition, the reaction mixture was charged with 55 psi of H$_2$ overnight. At the conclusion of this period, the Pd—C was filtered off through a pad of CELITE®, and the filter cake was rinsed with EtOH. The filtrate was concentrated under reduced pressure to afford Compound 3C as a colorless oil (2.36 g, 87% yield), which was used in next step without further purification. LC/MS (m/z)=344 (M+Na)$^+$.

Compound 3D.
4-(7-Fluoro-2,3-dihydrobenzofuran-2-yl)piperidine hydrochloride

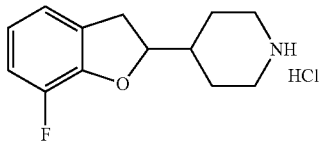 [SMILES: Fc1cccc2c1OC(C1CCNCC1)C2 ; Cl]

To a solution of tert-butyl 4-(7-fluoro-2,3-dihydrobenzofuran-2-yl)piperidine-1-carboxylate (2.36 g, 7.34 mmol) in MeOH (43.2 mL) was added HCl in dioxane (4 M, 26.8 mL, 107 mmol). Upon completion of addition, the mixture was stirred at room temperature for 5 h. After this time, the solvent was removed under reduced pressure to afford Compound 3D as a yellow oil (1.826 g, 97% yield), which was used in the next reaction without further purification. LC/MS (m/z)=222 (M+H)$^+$.

Compound 3E. 4-(5-Bromo-7-fluoro-2,3-dihydrobenzofuran-2-yl)piperidine

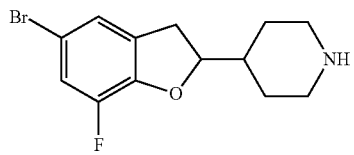 [SMILES: Fc1cc(Br)cc2c1OC(C1CCNCC1)C2]

To a solution of 4-(7-fluoro-2,3-dihydrobenzofuran-2-yl)piperidine hydrochloride (1.18 g, 4.58 mmol) in MeOH (36.6 mL) at 0° C. was added NBS (0.815 g, 4.58 mmol) in one portion. Upon completion of addition, the reaction mixture was immediately warmed to room temperature, where it stirred for 3 hours. At the conclusion of this period, the reaction mixture was quenched with aqueous Na$_2$H$_2$S$_2$O$_5$ (5%, 5 mL). The solvent was removed under reduced pressure to yield a residue. The residue was diluted with CH$_2$Cl$_2$ (5 mL), washed with NaHCO$_3$ (aq, sat, 3 mL) and brine (3 mL). The organic layer was separated, dried (Na$_2$SO$_4$), filtered, and concentrated to afford Compound 3E as a colorless oil (1.3 g, 95% yield). LC/MS (m/z)=301 (M+H)$^+$.

Compound 3F. 2-(4-(5-Bromo-7-fluoro-2,3-dihydrobenzofuran-2-yl)piperidin-1-yl)-5-propylpyrimidine

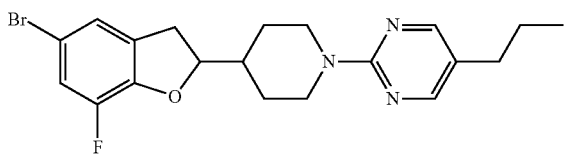 [SMILES: CCCc1cnc(N2CCC(C3Cc4cc(Br)cc(F)c4O3)CC2)nc1]

Compound 3F was prepared from Compound 3E and 2-chloro-5-propylpyrimidine in a similar manner to the procedure described in Compound 1H, Example 1. LC/MS (m/z)=421 (M+H)$^+$.

Compound 3G. tert-Butyl 4-(7-fluoro-2-(1-(5-propylpyrimidin-2-yl)piperidin-4-yl)-2,3-dihydrobenzofuran-5-yl)-5,6-dihydropyridine-1(2H)-carboxylate

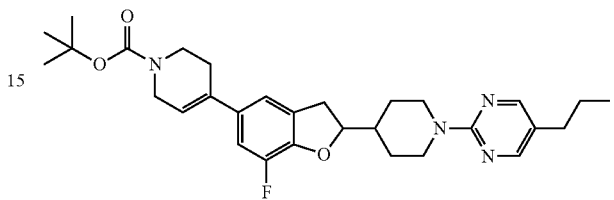

Compound 3G was prepared from Compound 3F and tert-butyl 4-(4,4,5,5-tetramethyl-1,3,2-dioxaborolan-2-yl)-5,6-dihydropyridine-1(2H)-carboxylate in a similar manner to the procedure described for Compound 1I in Example 1. $^1$H NMR (500 MHz, CDCl$_3$) δ ppm 8.15 (s, 2 H), 6.96 (s, 1 H), 6.92 (d, J=12.1 Hz, 1 H), 5.91 (br. s., 1 H), 4.81 (dd, J=13.3, 1.2 Hz, 2 H), 4.61-4.71 (m, 1 H), 4.04 (d, J=1.9 Hz, 2H), 3.61 (t, J=5.6 Hz, 2 H), 3.24 (dd, J=15.7, 9.1 Hz, 1 H), 3.04 (dd, J=15.7, 8.3 Hz, 1 H), 2.78-2.91 (m, J=12.8, 12.8, 6.1, 2.8 Hz, 2 H), 2.34-2.50 (m, 4 H), 2.01-2.09 (m, 1 H), 1.91-2.01 (m, 1 H), 1.70-1.79 (m, 1 H), 1.53-1.62 (m, 2 H), 1.49 (s, 9 H), 1.32-1.44 (m, 2 H), 0.93 (t, J=7.3 Hz, 3 H). 19F NMR (471 MHz, CDCl$_3$) δ ppm −138.98. LC/MS (m/z)=523 (M+H)$^+$.

Compound 3H. 2-(4-(7-Fluoro-5-(1,2,3,6-tetrahydropyridin-4-yl)-2,3-dihydrobenzofuran-2-yl)piperidin-1-yl)-5-propylpyrimidine

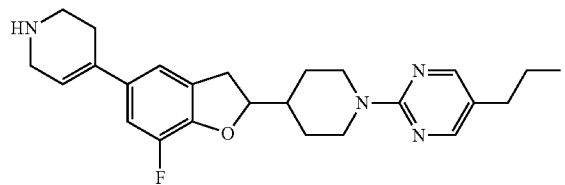 [SMILES: CCCc1cnc(N2CCC(C3Cc4cc(C5=CCNCC5)cc(F)c4O3)CC2)nc1]

Compound 3H was prepared from Compound 3G and TFA in a similar manner to the procedure described for Compound 1J in Example 1. LC/MS (m/z)=423 (M+H)$^+$.

EXAMPLE 3

Example 3 was prepared from Compound 3H and methyl 4-(chlorosulfonyl)butanoate in a similar manner to the procedure described in Example 1. $^1$H NMR (500 MHz, CDCl$_3$) δ ppm 8.15 (s, 2 H), 6.95 (s, 1 H), 6.92 (d, J=12.1 Hz, 1 H), 5.93 (dt, J=3.4, 1.8 Hz, 1 H), 4.77-4.85 (m, 2 H), 4.62-4.73 (m, 1 H), 3.95-4.01 (m, 2 H), 3.68 (s, 3 H), 3.54 (t, J=5.8 Hz, 2 H), 3.24 (dd, J=15.7, 9.1 Hz, 1 H), 3.00-3.11 (m, 3 H), 2.79-2.91 (m, J=12.9, 12.9, 6.2, 2.8 Hz, 2 H), 2.48-2.60 (m, 4 H), 2.39 (t, J=7.4 Hz, 2 H), 2.14 (qd, J=7.3, 7.2 Hz, 2 H), 2.01-2.08 (m, 1 H), 1.97 (dddd, J=11.4, 7.9, 7.7, 3.6 Hz, 1 H), 1.75 (d, J=12.7 Hz, 1 H), 1.50-1.63 (m, J=7.4, 7.4, 7.4, 7.4, 7.2 Hz, 2 H), 1.39 (qd, J=12.4, 4.3 Hz, 2 H), 0.93 (t, J=7.3 Hz, 3 H). $^{19}$F NMR (471 MHz, CDCl$_3$) δ ppm −138.74. LC/MS (m/z)=587 (M+H)$^+$.

EXAMPLE 4

4-(4-(7-Fluoro-2-(1-(5-propylpyrimidin-2-yl)piperidin-4-yl)-2,3-dihydrobenzofuran-5-yl)-5,6-dihydropyridin-1(2H)-ylsulfonyl)butan-1-ol

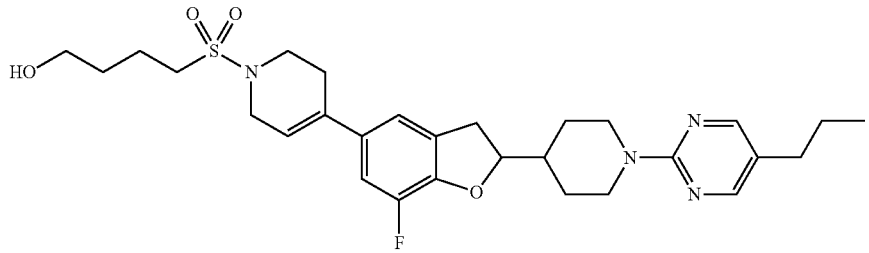 [SMILES: CCCc1cnc(N2CCC(C3Cc4cc(C5=CCN(S(=O)(=O)CCCCO)CC5)cc(F)c4O3)CC2)nc1]

To a solution of Example 3 (23 mg, 0.039 mmol) in THF (980 µL) at 0° C. was added LAH (47 µL, 0.047 mmol). Upon completion of addition, the reaction mixture was stirred at room temperature for 1 hour, and then quenched with aqueous HCl (1 N, 0.5 mL). The resulting mixture was diluted with EtOAc (4 mL) and washed with H$_2$O (2 mL) and brine (2 mL). The organic layer was separated, dried (Na$_2$SO$_4$), filtered, and concentrated to yield a residue. The residue was purified by column chromatography (silica gel, CH$_2$Cl$_2$/EtOAc gradient 0 to 100% EtOAc) to afford Example 4 as a white solid (17.7 mg, 78% yield). $^1$H NMR (400 MHz, CDCl$_3$) δ ppm 8.15 (s, 2 H), 6.96 (s, 1 H), 6.92 (d, J=12.1 Hz, 1 H), 5.94 (s, 1 H), 4.81 (d, J=13.2 Hz, 2 H), 4.64-4.73 (m, 1 H), 3.98 (d, J=2.7 Hz, 2 H), 3.70 (t, J=5.8 Hz, 2H), 3.54 (t, J=5.5 Hz, 2 H), 3.25 (dd, J=15.7, 9.1 Hz, 1 H), 2.99-3.09 (m, 3 H), 2.78-2.91 (m, 2 H), 2.56 (br. s., 2 H), 2.39 (t, J=7.7 Hz, 2 H), 2.05 (d, J=13.2 Hz, 1 H), 1.89-2.01 (m, 3 H), 1.49-1.81 (m, 6 H), 1.39 (qd, J=12.5, 4.4 Hz, 2 H), 0.93 (t, J=7.4 Hz, 3 H). LC/MS (m/z)=559 (M+H)$^+$.

EXAMPLE 5

(±)-2-(4-(7-Fluoro-5-(1-(propylsulfonyl)-1,2,3,6-tetrahydropyridin-4-yl)-2,3-dihydrobenzofuran-2-yl)piperidin-1-yl)-5-propylpyrimidine

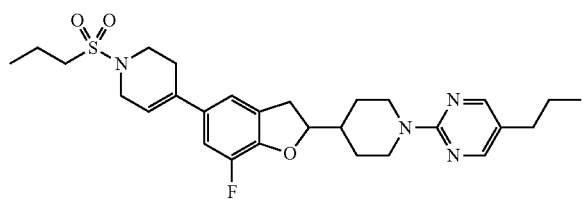

Example 5 was prepared from Compound 3H and propane-1-sulfonyl chloride in a similar manner to the procedure described in Example 1. $^1$H NMR (500 MHz, CDCl$_3$) δ ppm 8.15 (s, 2 H), 6.95 (s, 1 H), 6.92 (d, J=12.1 Hz, 1 H), 5.94 (ddd, J=3.4, 1.9, 1.8 Hz, 1 H), 4.76-4.87 (m, 2 H), 4.63-4.73 (m, 1 H), 3.97 (q, J=2.8 Hz, 2 H), 3.53 (t, J=5.6 Hz, 2 H), 3.24 (dd, J=15.7, 9.1 Hz, 1 H), 3.04 (dd, J=15.7, 8.3 Hz, 1 H), 2.91-2.98 (m, 2 H), 2.78-2.89 (m, J=12.9, 12.9, 6.1, 2.8 Hz, 2 H), 2.52-2.59 (m, 2 H), 2.39 (t, J=7.4 Hz, 2 H), 2.05 (d, J=13.2 Hz, 1 H), 1.97 (dddd, J=11.4, 7.9, 7.7, 3.6 Hz, 1 H), 1.82-1.91 (m, 2 H), 1.75 (d, J=12.9 Hz, 1 H), 1.57 (sxt, J=7.4 Hz, 2 H), 1.39 (qd, J=12.4, 4.3 Hz, 2 H), 1.07 (t, J=7.4 Hz, 3 H), 0.93 (t, J=7.4 Hz, 3 H).

$^{19}$F NMR (471 MHz, CDCl$_3$) δ ppm −138.73. LC/MS (m/z)=529 (M+H)$^+$.

EXAMPLES 6 AND 7

(S)-2-(4-(7-Fluoro-5-(1-(propylsulfonyl)-1,2,3,6-tetrahydropyridin-4-yl)-2,3-dihydrobenzofuran-2-yl)piperidin-1-yl)-5-propylpyrimidine, and (R)-2-(4-(7-Fluoro-5-(1-(propylsulfonyl)-1,2,3,6-tetrahydropyridin-4-yl)-2,3-dihydrobenzofuran-2-yl)piperidin-1-yl)-5-propylpyrimidine

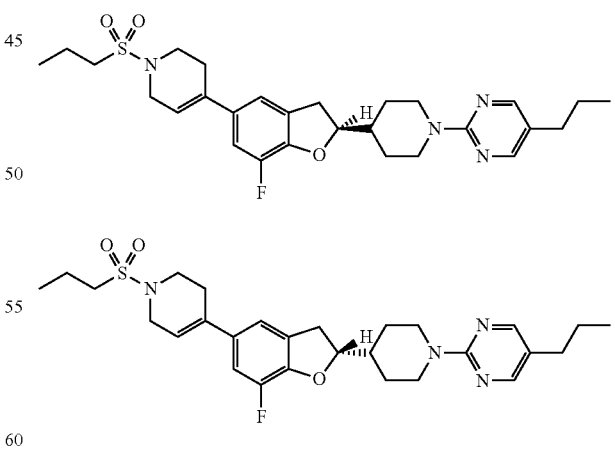

Compound 6A and Compound 7A. (S)-2-(4-(7-Fluoro-5-(1,2,3,6-tetrahydropyridin-4-yl)-2,3-dihydrobenzofuran-2-yl)piperidin-1-yl)-5-propylpyrimidine, and (R)-2-(4-(7-Fluoro-5-(1,2,3,6-tetrahydropyridin-4-yl)-2,3-dihydrobenzofuran-2-yl)piperidin-1-yl)-5-propylpyrimidine

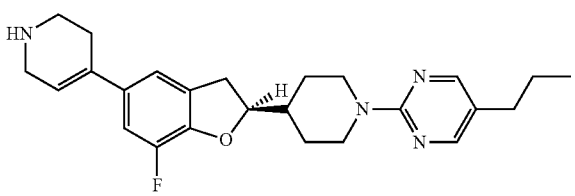

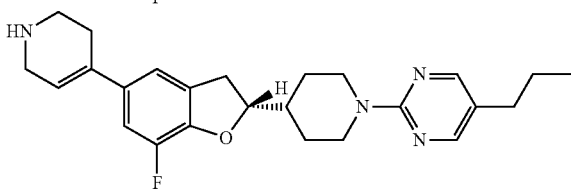

Compound 3H (24 mg) was subjected to SFC purification (CHIRALCEL® OJ-H SFC, 250×21 mm ID, 5 μm, Flow rate: 18 mL/min, Mobile phase: 50:50 Methanol-Ethanol-0.1% DEA, Detector: 254 nm) to afford Compound 6A (enantiomer I, 7.5 mg, 99.4% e.e) and Compound 7A (enantiomer II, 8.5 mg, 98.6% e.e). Enantiomer I has retention time=15.7 min; LC/MS (m/z)=423 (M+H)$^+$. Enantiomer II retention time=23.5 min; LC/MS (m/z)=423 (M+H)$^+$.

EXAMPLES 6 AND 7

Examples 6 and 7 were prepared from Compounds 6A and 7A, respectively, in a similar manner to the procedure described in Example 1. $^1$H NMR data are identical to those reported in Example 5.

EXAMPLE 8

2-(4-(7-Fluoro-5-(1-(propylsulfonyl)piperidin-4-yl)-2,3-dihydrobenzofuran-2-yl)piperidin-1-yl)-5-propylpyrimidine

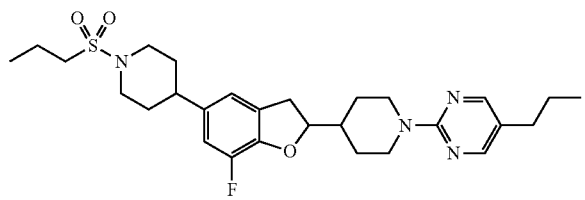 [SMILES: CCCc1cnc(N2CCC(C3Cc4cc(C5CCN(S(=O)(=O)CCC)CC5)cc(F)c4O3)CC2)nc1]

To a degassed solution of Example 5 (13 mg, 0.025 mmol) in EtOAc (0.77 mL) was added 10% Pd—C (10.5 mg, 9.84 μmol), and the mixture was stirred under H$_2$ (1 atm) at room temperature overnight. At the conclusion of this period, the Pd—C was filtered off through a pad of CELITE® and the solvent was evaporated off. The resulting residue was purified by column chromatography (silica gel, CH$_2$Cl$_2$/EtOAc gradient 0 to 100% EtOAc) to afford Example 8 as a white solid (11 mg, 83% yield).

$^1$H NMR (500 MHz, CDCl$_3$) δ ppm 8.15 (s, 2 H), 6.77 (s, 1 H), 6.73 (d, J=11.8 Hz, 1 H), 4.81 (dd, J=13.2, 1.7 Hz, 2 H), 4.62-4.70 (m, 1 H), 3.92 (dd, J=10.0, 2.1 Hz, 2 H), 3.23 (dd, J=15.7, 9.1 Hz, 1 H), 3.03 (dd, J=15.7, 8.5 Hz, 1 H), 2.79-2.96 (m, 6 H), 2.52 (tt, J=12.1, 3.6 Hz, 1 H), 2.40 (t, J=7.4 Hz, 2 H), 2.06 (d, J=13.2 Hz, 1 H), 1.93-2.01 (m, 1 H), 1.84-1.92 (m, 4 H), 1.67-1.79 (m, 3 H), 1.52-1.62 (m, 2 H), 1.33-1.44 (m, 2 H), 1.08 (t, J=7.4 Hz, 3 H), 0.92-0.97 (m, 3 H). $^{19}$F NMR (471 MHz, CDCl$_3$) δ ppm −138.70. LC/MS (m/z)=531 (M+H)$^+$.

EXAMPLE 9

5-Propyl-2-(4-(5-(4-(propylsulfonyl)piperazin-1-yl)-2,3-dihydrobenzofuran-2-yl)piperidin-1-yl)pyrimidine

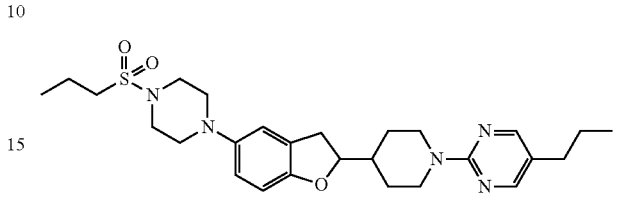

Compound 9A.
4-(5-Bromo-2,3-dihydrobenzofuran-2-yl)piperidine

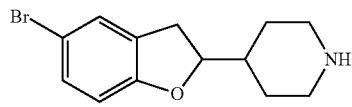 [SMILES: Brc1ccc2c(c1)CC(C1CCNCC1)O2]

To a solution of 4-(2,3-dihydrobenzofuran-2-yl)piperidine hydrochloride (0.566 g, 2.362 mmol) in MeOH (9.5 mL) at 0° C. was added NBS (0.42 g, 2.362 mmol) in one portion. Upon completion of addition, the reaction mixture was warmed to room temperature, where it stirred for 3 h. After this time, the solvent was removed under reduced pressure to yield a residue. The residue was diluted with CH$_2$Cl$_2$ (5 mL), washed with aqueous NaHCO$_3$ (saturated, 5 mL), and then brine (5 mL). The organic layer was separated, dried (K$_2$CO$_3$), filtered, and concentrated to afford crude Compound 9A as a brown oil (0.65 g, 92% yield), which was used in next reaction without further purification. $^1$H NMR (500 MHz, CDCl$_3$) δ ppm 7.26 (s, 1 H), 7.16 (dd, J=8.5, 2.2 Hz, 1 H), 6.59 (d, J=8.3 Hz, 1 H), 4.44-4.57 (m, 1 H), 3.20 (dd, J=16.1, 9.2 Hz, 1 H), 3.08 (dd, J=8.7, 3.7 Hz, 2 H), 2.98 (dd, J=16.1, 8.1 Hz, 1 H), 2.67 (s, 1 H), 2.53-2.64 (m, 2 H), 1.85-1.93 (m, 1 H), 1.70-1.81 (m, J=15.1, 7.6, 7.6, 3.6 Hz, 1 H), 1.66 (d, J=13.2 Hz, 1 H), 1.21-1.40 (m, 2 H).

Compound 9B. 2-(4-(5-Bromo-2,3-dihydrobenzofuran-2-yl)piperidin-1-yl)-5-propylpyrimidine

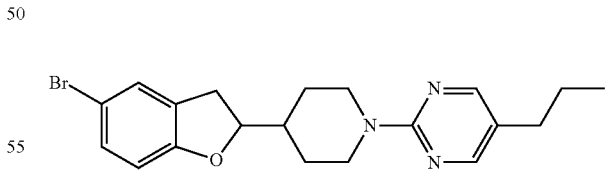

Compound 9B was prepared from Compound 9A and 2-chloro-5-propylpyrimidine in a similar manner to the procedure described for Compound 1H in Example 1. $^1$H NMR (400 MHz, CDCl$_3$) δ ppm 8.15 (s, 2 H), 7.24 (s, 1 H), 7.19 (d, J=9.3 Hz, 1 H), 6.62 (d, J=8.2 Hz, 1 H), 4.79 (d, J=13.2 Hz, 2 H), 4.56 (q, J=8.2 Hz, 1 H), 3.14-3.25 (m, 1 H), 2.99 (dd, J=15.9, 8.2 Hz, 1 H), 2.76-2.91 (m, 2 H), 2.39 (t, J=7.4 Hz, 2 H), 2.01 (d, J=13.2 Hz, 1 H), 1.90 (td, J=7.7, 3.8 Hz, 1 H), 1.62-1.78 (m, 1 H), 1.50-1.61 (m, 2 H), 1.29-1.43 (m, 2 H), 0.93 (t, J=7.4 Hz, 3 H). LC/MS (m/z)=402 (M+H)$^+$.

Compound 9C. tert-Butyl 4-(2-(1-(5-propylpyrimidin-2-yl)piperidin-4-yl)-2,3-dihydrobenzofuran-5-yl)piperazine-1-carboxylate

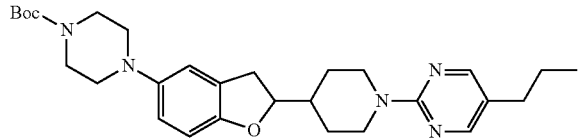 [SMILES: CCCc1cnc(N2CCC(C3Cc4cc(N5CCN(C(=O)OC(C)(C)C)CC5)ccc4O3)CC2)nc1]

To a degassed solution of 2-(4-(5-bromo-2,3-dihydrobenzofuran-2-yl)piperidin-1-yl)-5-propylpyrimidine (280 mg, 0.522 mmol), tert-butyl piperazine-1-carboxylate (389 mg, 2.088 mmol), t-BuONa (251 mg, 2.61 mmol), and BINAP (6.5 mg, 10.44 μmol) in toluene (5 mL) was added Pd$_2$(dba)$_3$ (28.7 mg, 0.031 mmol). Upon completion of addition, the reaction mixture was stirred in a sealed vial at 80° C. overnight. At the conclusion of this period, the reaction mixture was allowed to cool to room temperature. Once at the prescribed temperature, the reaction mixture was diluted with water (3 mL) and extracted with EtOAc (3×5 mL). The combined organic layers were washed with aqueous NaHCO$_3$ (saturated, 5 mL) and then brine (5 mL). The organic layer was separated, dried (Na$_2$SO$_4$), filtered, and concentrated to yield a residue. The residue was purified by column chromatography (silica gel, CH$_2$Cl$_2$/EtOAc gradient 0 to 50% EtOAc) to afford Compound 9C as a light yellow solid (201 mg, 76% yield). $^1$H NMR (500 MHz, CDCl$_3$) δ ppm 8.15 (s, 2 H), 6.83 (d, J=1.9 Hz, 1 H), 6.70-6.75 (m, 1 H), 6.66-6.69 (m, 1 H), 4.80 (dd, J=13.2, 2.5 Hz, 2 H), 4.48-4.56 (m, 1 H), 3.53-3.61 (m, 4 H), 3.18 (dd, J=15.5, 8.9 Hz, 1 H), 2.94-3.02 (m, 4 H), 2.80-2.90 (m, J=12.9, 12.9, 7.6, 2.8 Hz, 2 H), 2.40 (t, J=7.4 Hz, 2 H), 2.00-2.07 (m, 1 H), 1.91 (dddd, J=11.5, 8.0, 7.7, 3.6 Hz, 1 H), 1.74 (br. s., 1 H), 1.53-1.62 (m, 2 H), 1.47-1.51 (m, 9 H), 1.32-1.43 (m, 2 H), 0.94 (t, J=7.3 Hz, 3 H). LC/MS (m/z)=508 (M+H)$^+$.

Compound 9D. 2-(4-(5-(Piperazin-1-yl)-2,3-dihydrobenzofuran-2-yl)piperidin-1-yl)-5-propylpyrimidine

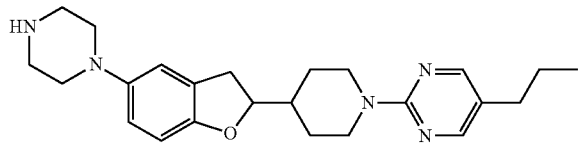 [SMILES: CCCc1cnc(N2CCC(C3Cc4cc(N5CCNCC5)ccc4O3)CC2)nc1]

Compound 9D was prepared from Compound 9C and TFA by in a similar manner to the procedure described for Compound 1J in Example 1. LC/MS (m/z)=408 (M+H)$^+$.

EXAMPLE 9

Example 9 was prepared from Compound 9D and propane-1-sulfonyl chloride in a similar manner to the procedure described in Example 1. $^1$H NMR (500 MHz, CDCl$_3$) δ ppm 8.15 (s, 2 H), 6.83 (d, J=2.2 Hz, 1 H), 6.70-6.75 (m, 1 H), 6.65-6.70 (m, 1 H), 4.80 (dd, J=13.5, 2.2 Hz, 2 H), 4.49-4.57 (m, 1 H), 3.40-3.47 (m, 4 H), 3.18 (dd, J=15.7, 8.8 Hz, 1 H), 3.07-3.13 (m, 4 H), 2.90-3.02 (m, 3 H), 2.80-2.89 (m, J=12.8, 12.8, 7.6, 2.6 Hz, 2 H), 2.40 (t, J=7.6 Hz, 2 H), 2.03 (d, J=12.4 Hz, 1 H), 1.84-1.95 (m, 3 H), 1.75 (d, J=13.2 Hz, 1 H), 1.53-1.63 (m, 2 H), 1.31-1.44 (m, J=12.4, 12.4, 12.3, 4.4 Hz, 2 H), 1.09 (t, J=7.4 Hz, 3 H), 0.94 (t, J=7.3 Hz, 3 H). LC/MS (m/z)=514 (M+H)$^+$.

EXAMPLE 10

1-(Propylsulfonyl)-4-(2-(1-(propylsulfonyl)piperidin-4-yl)-2,3-dihydrobenzofuran-5-yl)-1,2,3,6-tetrahydropyridine

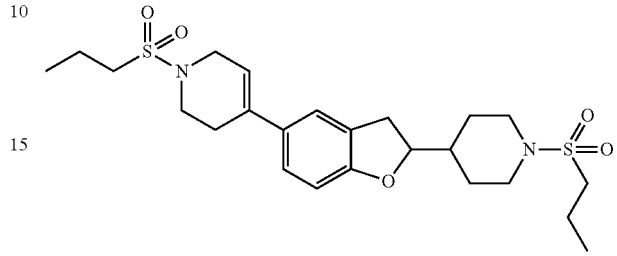

Compound 10A. 4-(5-Bromo-2,3-dihydrobenzofuran-2-yl)-1-(propylsulfonyl)piperidine

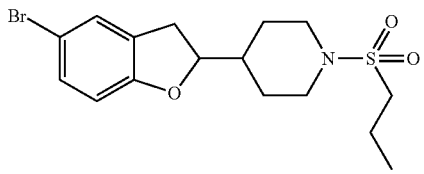 [SMILES: CCCS(=O)(=O)N1CCC(C2Cc3cc(Br)ccc3O2)CC1]

To a solution of 4-(5-bromo-2,3-dihydrobenzofuran-2-yl)piperidine (Compound 9A, 185 mg, 0.656 mmol) and Et$_3$N (0.18 mL, 1.311 mmol) in CH$_2$Cl$_2$ (6 mL) at 0° C. was added propane-1-sulfonyl chloride (140 mg, 0.983 mmol). Upon completion of addition, the reaction mixture was warmed to room temperature, where it stirred for 2 hours. After this time, the reaction mixture was diluted with CH$_2$Cl$_2$ (5 mL) and washed with aqueous NaHCO$_3$ (saturated, 5 mL). The organic layer was separated, dried (Na$_2$SO$_4$), filtered, and concentrated to yield a residue. The residue was purified by column chromatography (silica gel, hexanes/EtOAc gradient 0 to 50% EtOAc) to afford Compound 10A as a white solid (213 mg, 0.549 mmol, 84% yield). $^1$H NMR (500 MHz, CDCl$_3$) δ ppm 7.27-7.25 (m, 1 H), 7.21 (dd, J=8.4, 2.1 Hz, 1 H), 6.63 (d, J=8.3 Hz, 1 H), 4.63-4.53 (m, 1 H), 3.93-3.84 (m, 2 H), 3.22 (dd, J=15.7, 9.1 Hz, 1 H), 2.96 (dd, J=15.8, 8.1 Hz, 1 H), 2.91-2.86 (m, 2 H), 2.80-2.71 (m, 2 H), 2.05-1.99 (m, 1 H), 1.90-1.81 (m, 2 H), 1.80-1.71 (m, 2 H), 1.53-1.41 (m, 2 H), 1.07 (t, J=7.4 Hz, 3 H). LC/MS (m/z)=389 (M+H)$^+$.

Compound 10B. tert-Butyl 4-(2-(1-(propylsulfonyl)piperidin-4-yl)-2,3-dihydrobenzofuran-5-yl)-5,6-dihydropyridine-1(2H)-carboxylate

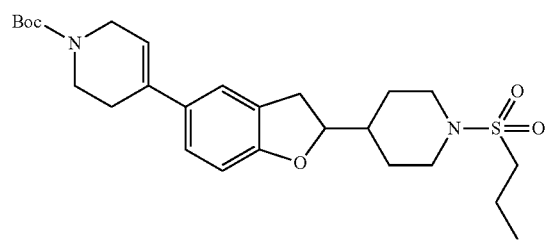 [SMILES: CCCS(=O)(=O)N1CCC(C2Cc3cc(C4=CCN(C(=O)OC(C)(C)C)CC4)ccc3O2)CC1]

Compound 10B was prepared from Compound 10A and tert-butyl 4-(4,4,5,5-tetramethyl-1,3,2-dioxaborolan-2-yl)-5,6-dihydropyridine-1(2H)-carboxylate in a similar manner to the procedure described for Compound 1I in Example 1.

Compound 10C. 4-(2-(1-(Propylsulfonyl)piperidin-4-yl)-2,3-dihydrobenzofuran-5-yl)-1,2,3,6-tetrahydropyridine

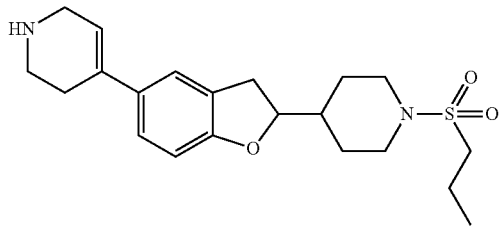 [SMILES: CCCS(=O)(=O)N1CCC(C2Cc3cc(C4=CCNCC4)ccc3O2)CC1]

Compound 10C was prepared from Compound 10B and TFA in a similar manner to the procedure described for Compound 1J in Example 1.

EXAMPLE 10

Example 10 was prepared from Compound 10C and propane-1-sulfonyl chloride in a similar manner to the procedure described in Example 1. $^1$H NMR (500 MHz, CDCl$_3$) δ ppm 7.19 (s, 1 H), 7.13 (dd, J=8.4, 1.8 Hz, 1 H), 6.72 (d, J=8.5 Hz, 1 H), 5.93 (ddd, J=3.2, 1.9, 1.7 Hz, 1 H), 4.53-4.63 (m, 1 H), 3.98 (q, J=2.8 Hz, 2 H), 3.84-3.93 (m, 2 H), 3.55 (t, J=5.8 Hz, 2 H), 3.23 (dd, J=15.4, 9.1 Hz, 1 H), 2.92-3.01 (m, 3 H), 2.85-2.92 (m, 2 H), 2.70-2.81 (m, 2 H), 2.55-2.63 (m, 2 H), 1.98-2.07 (m, 1 H), 1.81-1.94 (m, 4 H), 1.70-1.80 (m, 2 H), 1.41-1.53 (m, 2 H), 1.07 (td, J=7.4, 3.0 Hz, 6 H). LC/MS (m/z)=497 (M+H)$^+$.

EXAMPLE 11

4-(4-(2-(1-(5-Cyclopropylpyrimidin-2-yl)piperidin-4-yl)-2-methyl-2,3-dihydrobenzofuran-5-yl)-5,6-dihydropyridin-1(2H)-ylsulfonyl)butan-1-ol

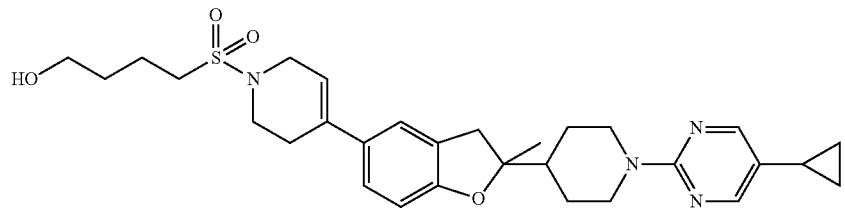 [SMILES: CC1(C2CCN(c3ncc(C4CC4)cn3)CC2)Cc2cc(C3=CCN(S(=O)(=O)CCCCO)CC3)ccc2O1]

Compound 11A. tert-Butyl 4-(1-(2-bromophenyl)-2-hydroxypropan-2-yl)piperidine-1-carboxylate

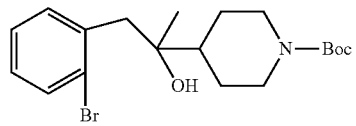 [SMILES: CC(C)(C)OC(=O)N1CCC(C(C)(O)Cc2ccccc2Br)CC1]

A mixture of 1-bromo-2-(bromomethyl)benzene (4.40 g, 17.60 mmol), magnesium (0.984 g, 40.5 mmol), and I$_2$ (2.2 mg, 8.80 μmol) in Et$_2$O (87 mL) was heated to reflux under argon until the reaction initiated (indicated by decolorization of I$_2$) and then stirred at room temperature for 2 hours. After this time, the reaction mixture was added to a solution of tert-butyl 4-acetylpiperidine-1-carboxylate (2 g, 8.80 mmol) in Et$_2$O (1.2 mL) and then stirred for 19 hours. At the conclusion of this period, the reaction mixture was quenched with aqueous NH$_4$Cl (saturated, 20 mL) and extracted with EtOAc (3×25 mL). The combined organic layers were washed with H$_2$O (3×15 mL) and brine (15 mL). The resulted organic layer was separated, dried (Na$_2$SO$_4$), filtered, and concentrated to yield a residue. The residue was purified by column chromatography (silica gel, hexanes/EtOAc gradient 0 to 60% EtOAc) to afford Compound 11A as a white semi-solid (1.14 g, 31% yield).

Compound 11B. tert-Butyl 4-(2-methyl-2,3-dihydrobenzofuran-2-yl)piperidine-1-carboxylate

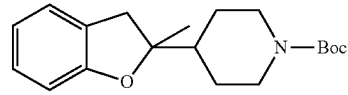 [SMILES: CC(C)(C)OC(=O)N1CCC(C2(C)Cc3ccccc3O2)CC1]

A mixture of tert-butyl 4-(1-(2-bromophenyl)-2-hydroxypropan-2-yl)piperidine-1-carboxylate (1.14 g, 2.86 mmol), BINAP (0.266 g, 0.427 mmol), Pd(OAc)$_2$ (93 mg, 0.412 mmol), and K$_2$CO$_3$ (1.188 g, 8.59 mmol) in toluene (14.3 mL) was degassed for 10 min. After this time, the reaction mixture was heated in 110° C. oil bath overnight. At the conclusion of this period, the resulting solid was collected by filtration and rinsed with CH$_2$Cl$_2$. The filtrate was concentrated to afford the crude product, which was purified by column chromatography (silica gel, hexanes/EtOAc gradient 0 to 25% EtOAc) to afford Compound 11B as a colorless oil (0.959 g, 97% yield). LC/MS (m/z)=657 (2M+Na)$^+$.

Compound 11C. tert-Butyl 4-(5-bromo-2-methyl-2,3-dihydrobenzofuran-2-yl)piperidine-1-carboxylate

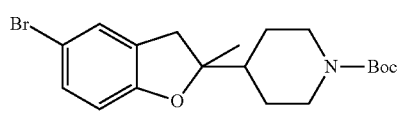 [SMILES: CC(C)(C)OC(=O)N1CCC(C2(C)Cc3cc(Br)ccc3O2)CC1]

To a solution of tert-butyl 4-(2-methyl-2,3-dihydrobenzofuran-2-yl)piperidine-1-carboxylate (0.66 g, 2.079 mmol) in CHCl$_3$ (8.3 mL) at 0° C. was slowly added Br$_2$ (107 μL, 2.079 mmol). After completion of addition, the reaction mixture was warmed to room temperature, where it stirred for 3 hours. After this time, the reaction mixture was cooled to 0° C. and quenched with aqueous NaHCO₃ (saturated, 6 mL) and sodium metasulfite (15 mg). The resulting mixture was extracted with EtOAc (3×3 mL). The combined organic layers were dried (Na₂SO₄), filtered, and concentrated to afford crude Compound 11C, which was used in next reaction without further purification.

Compound 11D. 4-(5-Bromo-2-methyl-2,3-dihydrobenzofuran-2-yl)piperidine

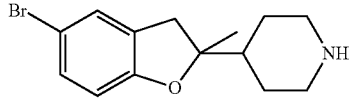 [SMILES: CC1(C2CCNCC2)Cc2cc(Br)ccc2O1]

Compound 11D was prepared from Compound 11C and TFA in a similar manner to the procedure described for Compound 1J in Example 1. LC/MS (m/z)=296 (M+H)⁺.

Compound 11E. 2-(4-(5-Bromo-2-methyl-2,3-dihydrobenzofuran-2-yl)piperidin-1-yl)-5-cyclopropylpyrimidine

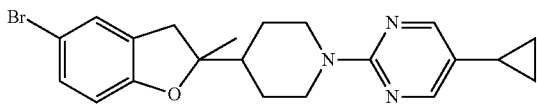 [SMILES: CC1(C2CCN(c3ncc(C4CC4)cn3)CC2)Cc2cc(Br)ccc2O1]

A mixture of 4-(5-bromo-2-methyl-2,3-dihydrobenzofuran-2-yl)piperidine (0.3 g, 1.013 mmol), 2-chloro-5-cyclopropylpyrimidine (0.204 g, 1.317 mmol) and K₂CO₃ (0.42 g, 3.04 mmol) in DMF (5 mL) was heated in 90° C. oil bath overnight. At the conclusion of this period, the reaction mixture was cooled to room temperature, quenched with H₂O (5 mL), and then extracted with EtOAc (3×5 mL). The combined organic layers were washed with H₂O (3×5 mL) and brine (5 mL). The organic layer was separated, dried (Na₂SO₄), filtered, and concentrated to yield a residue. The residue was purified by column chromatography (silica gel, hexanes/EtOAc gradient 0 to 35% EtOAc) to afford Compound 11E as white solid (0.315 g, 31% yield). LC/MS (m/z)=414 (M+H)⁺.

Compound 11F. tert-Butyl 4-(2-(1-(5-cyclopropylpyrimidin-2-yl)piperidin-4-yl)-2-methyl-2,3-dihydrobenzofuran-5-yl)-5,6-dihydropyridine-1(2H)-carboxylate

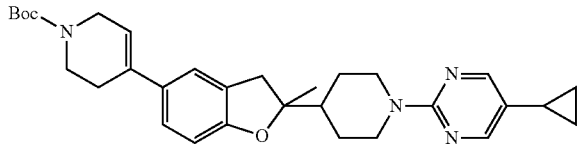 [SMILES: CC(C)(C)OC(=O)N1CC=C(c2ccc3c(c2)CC(C)(C2CCN(c4ncc(C5CC5)cn4)CC2)O3)CC1]

To a degassed solution of 2-(4-(5-bromo-2-methyl-2,3-dihydrobenzofuran-2-yl)piperidin-1-yl)-5-cyclopropylpyrimidine (424 mg, 1.02 mmol), tert-butyl 4-(4,4,5,5-tetramethyl-1,3,2-dioxaborolan-2-yl)-5,6-dihydropyridine-1(2H)-carboxylate (380 mg, 1.23 mmol), and K₂CO₃ (424 mg, 3.07 mmol) in dioxane (6 mL) and water (2 mL) was added Pd(Ph₃P)₄ (59.1 mg, 0.051 mmol). Upon completion of addition, the reaction mixture was heated in 100° C. oil bath for 3 hours. After this time, the reaction mixture was cooled to room temperature, diluted with water, and extracted with CH₂Cl₂ (3×5 mL). The combined organic layers were dried (Na₂SO₄), filtered, and concentrated to yield a residue. The residue was purified by column chromatography (silica gel, hexanes/EtOAc gradient 0 to 50% EtOAc) to afford Compound 11F as a white solid (360 mg, 0.697 mmol, 68% yield). ¹H NMR (500 MHz, CDCl₃) δ ppm 8.11 (s, 2 H), 7.15 (s, 1 H), 7.13 (d, J=8.5 Hz, 1 H), 6.65-6.71 (m, 1 H), 5.88 (br. s., 1 H), 4.75-4.87 (m, 2 H), 4.05 (br. s., 2 H), 3.73 (t, J=6.2 Hz, 1 H), 3.62 (t, J=5.5 Hz, 2 H), 3.16 (d, J=15.7 Hz, 1 H), 2.74-2.87 (m, 2 H), 2.39-2.54 (m, 2 H), 1.86-1.96 (m, 2 H), 1.76-1.84 (m, 1 H), 1.67-1.74 (m, 1 H), 1.61 (m, 1 H), 1.49 (s, 9 H), 1.37-1.41 (m, 3 H), 1.23-1.36 (m, 1 H), 0.84-0.92 (m, 2 H), 0.54-0.60 (m, 2 H). LC/MS (m/z)=517 (M+H)⁺.

Compound 11G. 5-Cyclopropyl-2-(4-(2-methyl-5-(1,2,3,6-tetrahydropyridin-4-yl)-2,3-dihydrobenzofuran-2-yl)piperidin-1-yl)pyrimidine

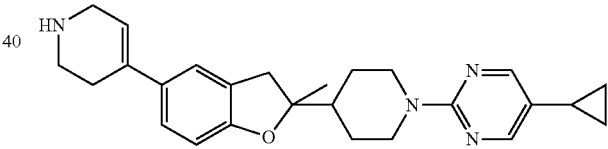

Compound 11G was prepared from Compound 11F and TFA in a similar manner to the procedure described for Compound 1J in Example 1. LC/MS (m/z)=417 (M+H)⁺.

Compound 11H. Methyl 4-(4-(2-(1-(5-cyclopropylpyrimidin-2-yl)piperidin-4-yl)-2-methyl-2,3-dihydrobenzofuran-5-yl)-5,6-dihydropyridin-1(2H)-ylsulfonyl)butanoate

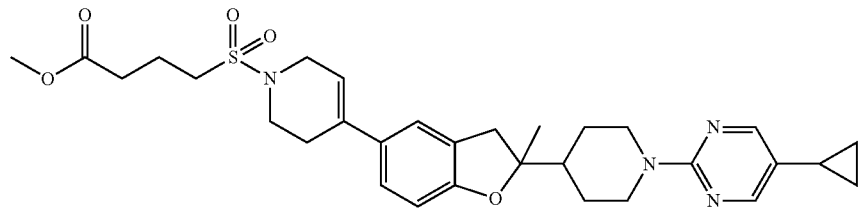 [SMILES: COC(=O)CCCS(=O)(=O)N1CC=C(c2ccc3c(c2)CC(C)(C2CCN(c4ncc(C5CC5)cn4)CC2)O3)CC1]

To a solution of 5-cyclopropyl-2-(4-(2-methyl-5-(1,2,3,6-tetrahydropyridin-4-yl)-2,3-dihydrobenzofuran-2-yl)piperidin-1-yl)pyrimidine (90 mg, 0.216 mmol) and triethylamine (0.061 mL, 0.432 mmol) in CH$_2$Cl$_2$ (2 mL) at 0° C. was added methyl 4-(chlorosulfonyl)butanoate (65 mg, 0.324 mmol). Upon completion of addition, the reaction mixture was warmed to room temperature, where it stirred for 3 h. After this time, the reaction mixture was diluted with CH$_2$Cl$_2$ (4 mL), and the resulting mixture was washed with aqueous NaHCO$_3$ (saturated, 3×3 mL). The organic layer was separated, dried (Na$_2$SO$_4$), filtered, and concentrated to yield a residue. The residue was purified via preparative HPLC (solvent A: 10% MeOH/H$_2$O with 0.1% TFA; solvent B: 90% MeOH/H$_2$O with 0.1% TFA; Column: PHENOMENEX® Axia 5μ C18 30×100 mm, flow rate=40 mL/min) to afford Compound 11H as a white solid (46 mg, 0.079 mmol, 36.7% yield). $^1$H NMR (500 MHz, CDCl$_3$) δ ppm 8.02 (s, 2 H), 7.06 (s, 1 H), 7.01-7.05 (m, 1 H), 6.60 (d, J=8.3 Hz, 1 H), 5.82 (ddd, J=3.2, 1.9, 1.7 Hz, 1 H), 4.65-4.78 (m, 2 H), 3.85-3.92 (m, 2 H), 3.60 (s, 3 H), 3.46 (t, J=5.8 Hz, 2 H), 3.08 (d, J=15.7 Hz, 1 H), 2.98 (dd, J=8.4, 6.7 Hz, 2 H), 2.65-2.78 (m, 3 H), 2.50 (d, J=1.7 Hz, 2 H), 2.44 (t, J=7.0 Hz, 2 H), 2.01-2.13 (m, 2 H), 1.76-1.87 (m, 2 H), 1.67-1.75 (m, 1 H), 1.56-1.65 (m, 1 H), 1.30 (s, 3 H), 1.15-1.28 (m, 2 H), 0.76-0.83 (m, 2 H), 0.45-0.51 (m, 2 H). LC/MS (m/z)=581 (M+H)$^+$.

EXAMPLE 11

To a solution of methyl 4-(4-(2-(1-(5-cyclopropylpyrimidin-2-yl)piperidin-4-yl)-2-methyl-2,3-dihydrobenzofuran-5-yl)-5,6-dihydropyridin-1(2H)-ylsulfonyl)butanoate (46 mg, 0.079 mmol) in THF (1 mL) at 0° C. was added a solution of LAH in THF (0.079 mL, 2 M, 0.158 mmol). Upon completion of addition, the reaction mixture was stirred at 0° C. for 1 hour. After this time, the reaction mixture was diluted with CH$_2$Cl$_2$ (5 mL), washed with aqueous HCl (1 N, 3 mL), and then brine (3 mL). The organic layer was separated and concentrated to afford the crude product, which was purified by preparative HPLC (solvent A: 10% MeOH/H$_2$O with 0.1% TFA; solvent B: 90% MeOH/H$_2$O with 0.1% TFA; Column: PHENOMENEX® Axia 5μ C18 30×100 mm, flow rate=40 mL/min) to afford Example 11 as a white solid (19 mg, 0.034 mmol, 43.4% yield). $^1$H NMR (500 MHz, CDCl$_3$) δ ppm 8.13 (s, 2 H), 7.16 (s, 1 H), 7.11-7.15 (m, 1 H), 6.71 (d, J=8.3 Hz, 1 H), 5.93 (ddd, J=3.2, 1.9, 1.7 Hz, 1 H), 4.78-4.89 (m, 2 H), 3.97-4.03 (m, 2 H), 3.67-3.77 (m, 2 H), 3.57 (t, J=5.6 Hz, 2 H), 3.18 (d, J=16.0 Hz, 1 H), 3.01-3.09 (m, 2 H), 2.75-2.88 (m, 3 H), 2.55-2.65 (m, 2 H), 1.87-2.03 (m, 4 H), 1.82 (dd, J=12.9, 2.5 Hz, 1 H), 1.68-1.78 (m, 3 H), 1.41 (s, 3 H), 1.26-1.39 (m, 3 H), 0.87-0.93 (m, 2 H), 0.56-0.62 (m, 2 H). LC/MS (m/z)=553 (M+H)$^+$.

EXAMPLES 12 TO 50

Examples 12 to 50 set forth in Table 1 were synthesized according to the procedures described in Examples 1 to 11, the schemes, or by other similar methods known to one skilled in the art, with other appropriate reagents.

TABLE 1

| Example | Structure | LC/MS (m/z) |
|---|---|---|
| 12 | 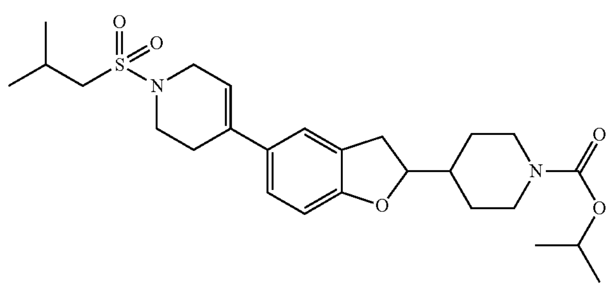 [SMILES: CC(C)CS(=O)(=O)N1CC=C(c2ccc3c(c2)CC(C2CCN(C(=O)OC(C)C)CC2)O3)CC1] | 491 |
| 13 | 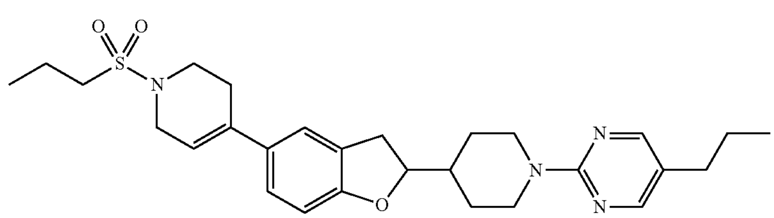 [SMILES: CCCc1cnc(N2CCC(C3Cc4cc(C5=CCN(S(=O)(=O)CCC)CC5)ccc4O3)CC2)nc1] | 511 |
| 14 | 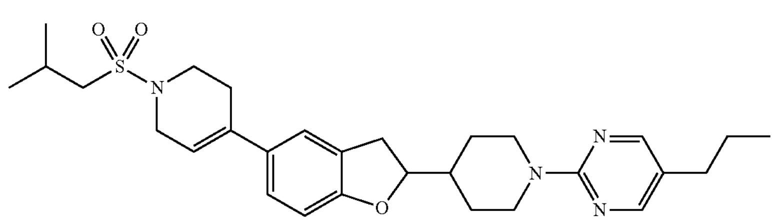 | 525 |

TABLE 1-continued

| Example | Structure | LC/MS (m/z) |
|---|---|---|
| 15 | 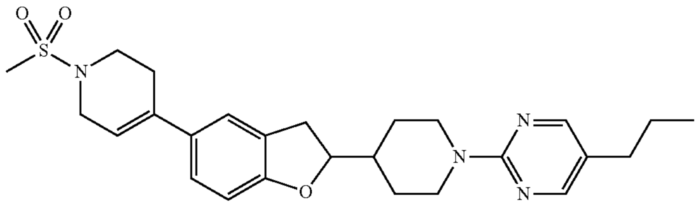 [SMILES: CCCc1cnc(N2CCC(C3Cc4cc(C5=CCN(S(C)(=O)=O)CC5)ccc4O3)CC2)nc1] | 483 |
| 16 | 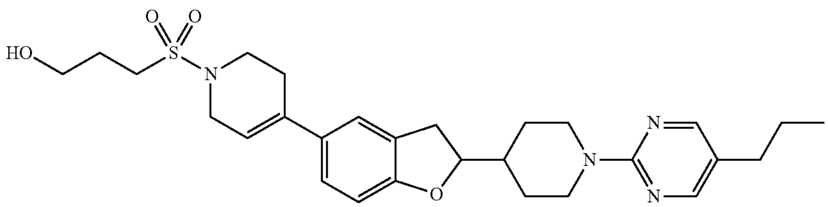 [SMILES: CCCc1cnc(N2CCC(C3Cc4cc(C5=CCN(S(=O)(=O)CCCO)CC5)ccc4O3)CC2)nc1] | 527 |
| 17 | 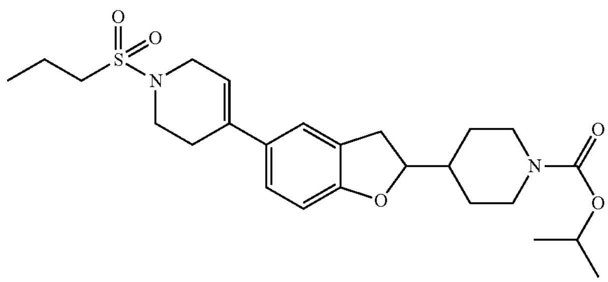 [SMILES: CCCS(=O)(=O)N1CC=C(c2ccc3c(c2)CC(C2CCN(C(=O)OC(C)C)CC2)O3)CC1] | 477 |
| 18 | 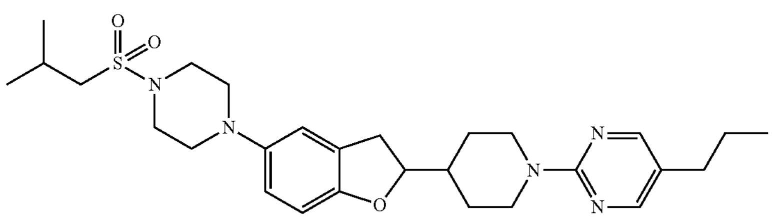 [SMILES: CCCc1cnc(N2CCC(C3Cc4cc(N5CCN(S(=O)(=O)CC(C)C)CC5)ccc4O3)CC2)nc1] | 528 |
| 19 | 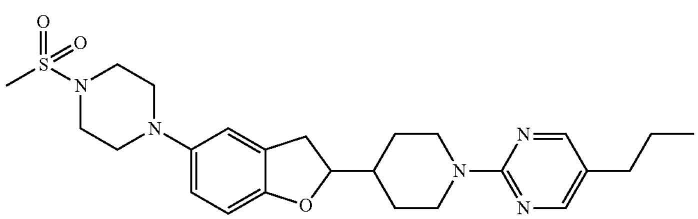 [SMILES: CCCc1cnc(N2CCC(C3Cc4cc(N5CCN(S(C)(=O)=O)CC5)ccc4O3)CC2)nc1] | 486 |
| 20 | 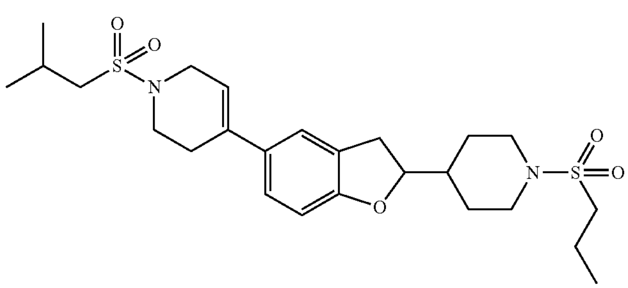 [SMILES: CCCS(=O)(=O)N1CCC(C2Cc3cc(C4=CCN(S(=O)(=O)CC(C)C)CC4)ccc3O2)CC1] | 511 |

TABLE 1-continued

| Example | Structure | LC/MS (m/z) |
|---|---|---|
| 21 | 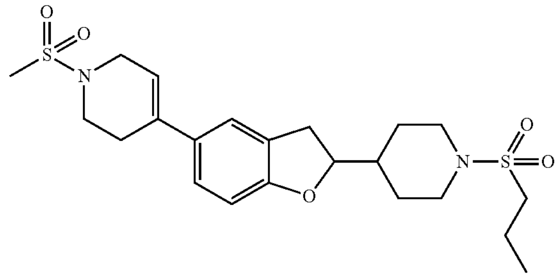 [SMILES: CCCS(=O)(=O)N1CCC(C2Cc3cc(C4=CCN(S(C)(=O)=O)CC4)ccc3O2)CC1] | 469 |
| 22 | 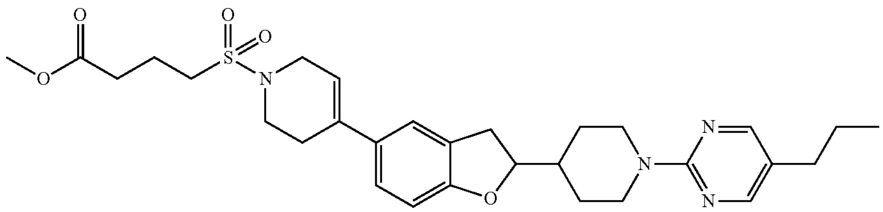 [SMILES: CCCc1cnc(N2CCC(C3Cc4cc(C5=CCN(S(=O)(=O)CCCC(=O)OC)CC5)ccc4O3)CC2)nc1] | 569 |
| 23 | 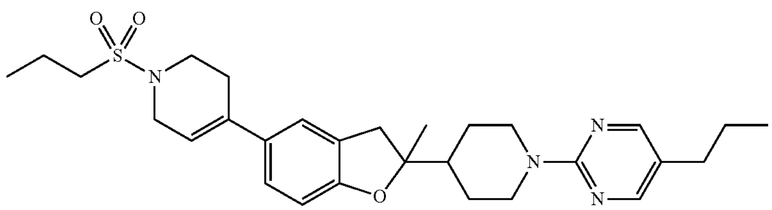 [SMILES: CCCc1cnc(N2CCC(C3(C)Cc4cc(C5=CCN(S(=O)(=O)CCC)CC5)ccc4O3)CC2)nc1] | 525 |
| 24 | 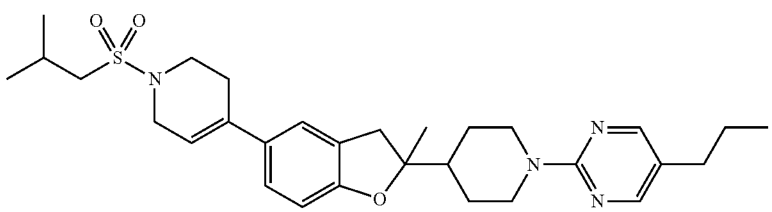 [SMILES: CCCc1cnc(N2CCC(C3(C)Cc4cc(C5=CCN(S(=O)(=O)CC(C)C)CC5)ccc4O3)CC2)nc1] | 539 |
| 25 | 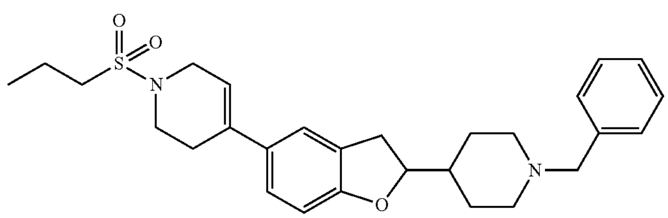 [SMILES: CCCS(=O)(=O)N1CC=C(c2ccc3c(c2)CC(C2CCN(Cc4ccccc4)CC2)O3)CC1] | 481 |
| 26 | 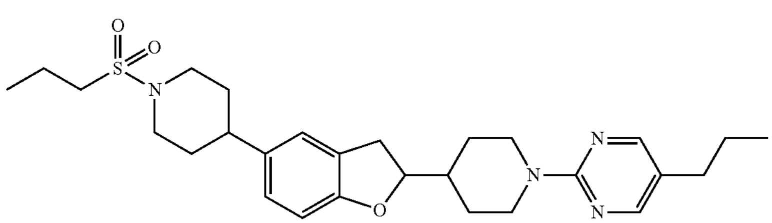 | 513 |
| 27 | 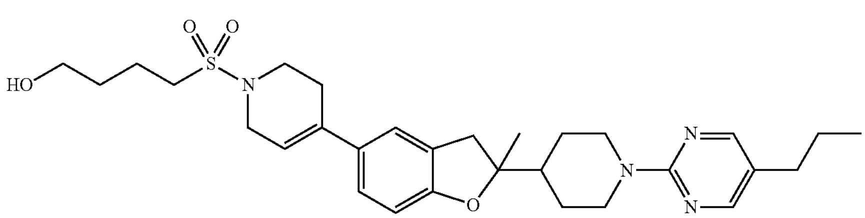 [SMILES: CCCc1cnc(N2CCC(C3(C)Cc4cc(C5=CCN(S(=O)(=O)CCCCO)CC5)ccc4O3)CC2)nc1] | 555 |

TABLE 1-continued

| Example | Structure | LC/MS (m/z) |
| --- | --- | --- |
| 28 | 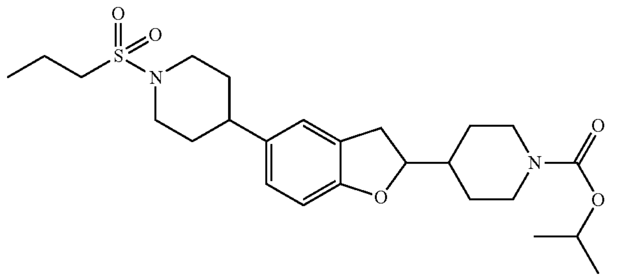 [SMILES: CCCS(=O)(=O)N1CCC(c2ccc3c(c2)CC(C2CCN(C(=O)OC(C)C)CC2)O3)CC1] | 479 |
| 29 | 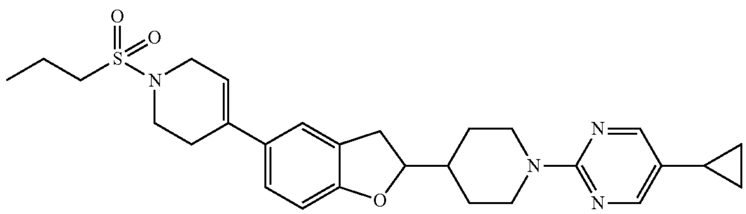 [SMILES: CCCS(=O)(=O)N1CC=C(c2ccc3c(c2)CC(C2CCN(c4ncc(C5CC5)cn4)CC2)O3)CC1] | 509 |
| 30 | 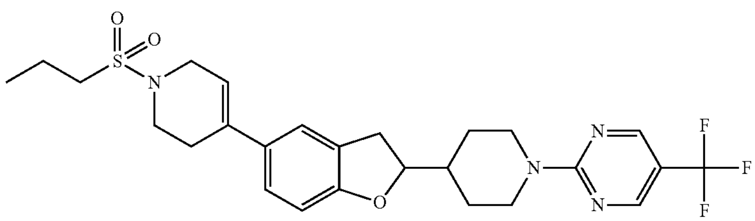 [SMILES: CCCS(=O)(=O)N1CC=C(c2ccc3c(c2)CC(C2CCN(c4ncc(C(F)(F)F)cn4)CC2)O3)CC1] | 537 |
| 31 | 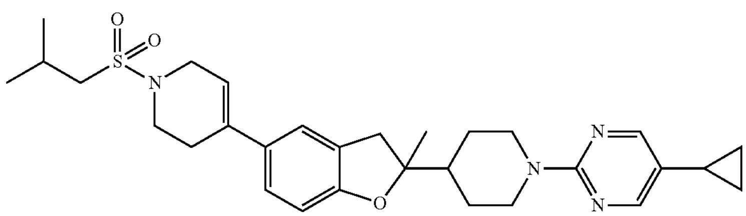 [SMILES: CC(C)CS(=O)(=O)N1CC=C(c2ccc3c(c2)CC(C)(C2CCN(c4ncc(C5CC5)cn4)CC2)O3)CC1] | 537 |
| 32 | 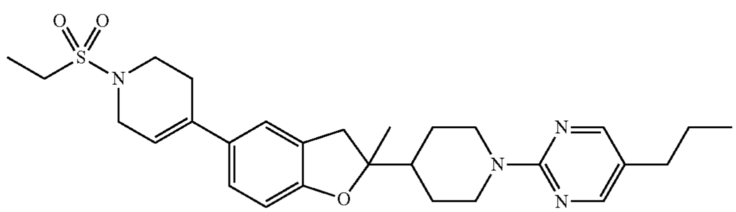 [SMILES: CCCc1cnc(N2CCC(C3(C)Cc4cc(C5=CCN(S(=O)(=O)CC)CC5)ccc4O3)CC2)nc1] | 511 |
| 33 | 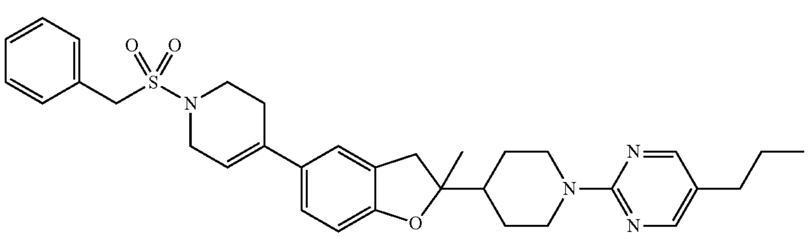 [SMILES: CCCc1cnc(N2CCC(C3(C)Cc4cc(C5=CCN(S(=O)(=O)Cc6ccccc6)CC5)ccc4O3)CC2)nc1] | 573 |
| 34 | 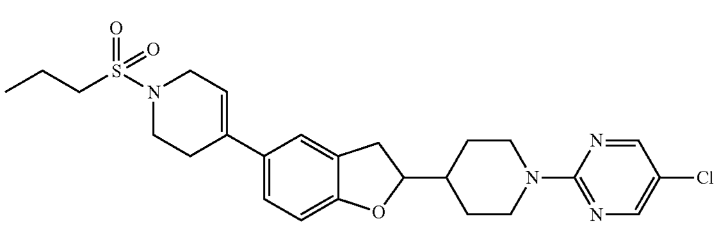 | 504 |

TABLE 1-continued
| Example | Structure | LC/MS (m/z) |
|---|---|---|
| 35 | 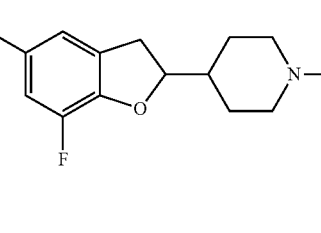 | 543 |
| 36 | 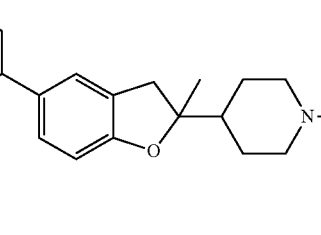 | 523 |
| 37 | 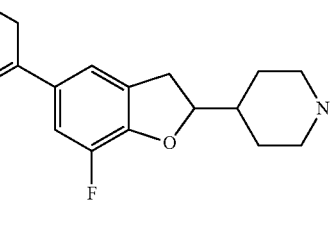 | 545 |
| 38 | 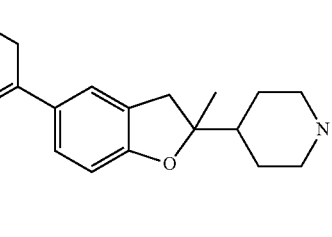 | 541 |
| 39 | 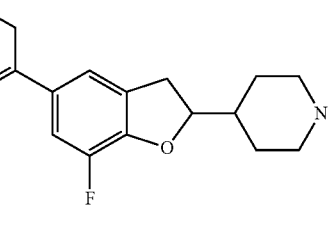 | 522 |
| 40 | 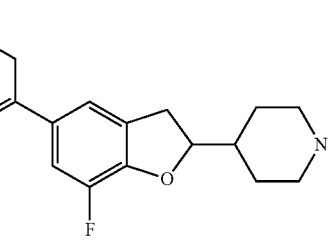 | 536 |

TABLE 1-continued
| Example | Structure | LC/MS (m/z) |
|---|---|---|
| 41 | 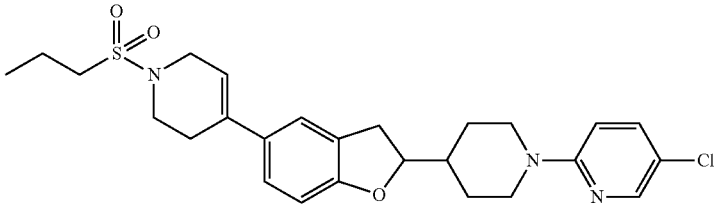 [SMILES: CCCS(=O)(=O)N1CC=C(c2ccc3c(c2)CC(C2CCN(c4ccc(Cl)cn4)CC2)O3)CC1] | 503 |
| 42 | 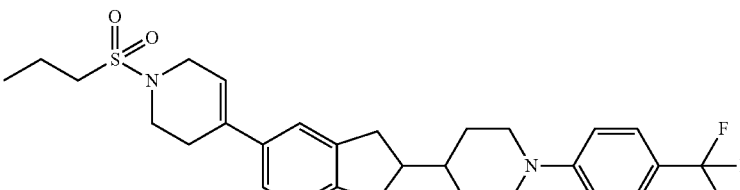 | 536 |
| 43 | 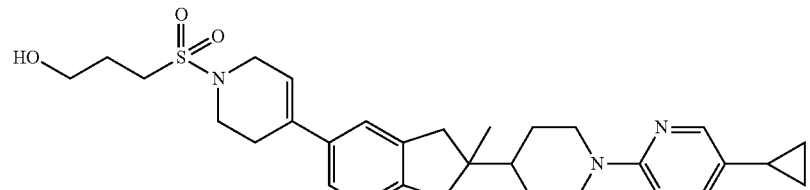 | 539 |
| 44 | 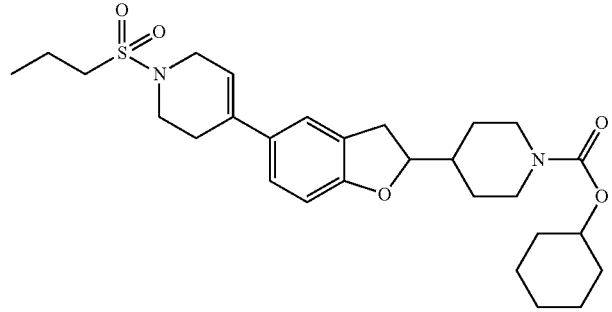 [SMILES: CCCS(=O)(=O)N1CC=C(c2ccc3c(c2)CC(C2CCN(C(=O)OC4CCCCC4)CC2)O3)CC1] | 517 |
| 45 | 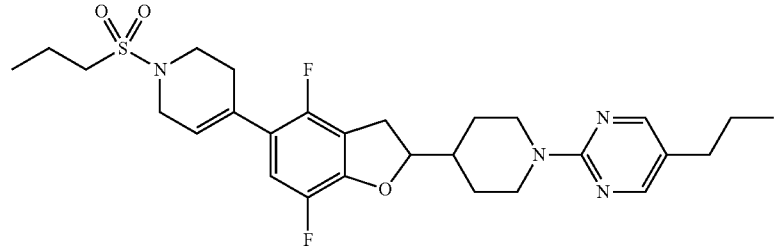 [SMILES: CCCc1cnc(N2CCC(C3Cc4c(F)c(C5=CCN(S(=O)(=O)CCC)CC5)cc(F)c4O3)CC2)nc1] | 547 |
| 46 | 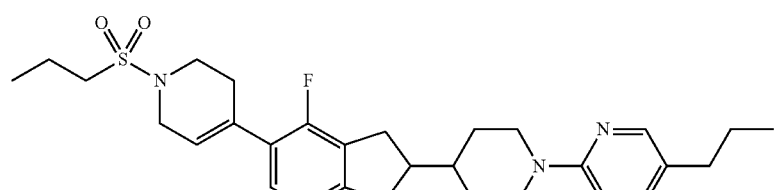 | 529 |

TABLE 1-continued

| Example | Structure | LC/MS (m/z) |
|---------|-----------|-------------|
| 47 | 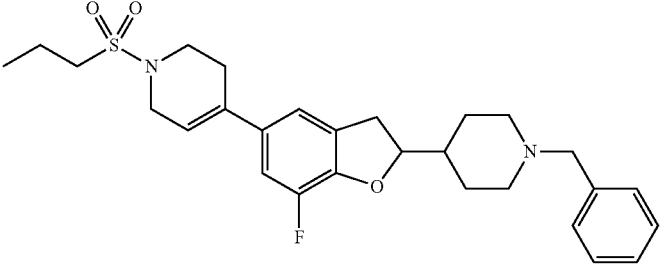 [SMILES: CCCS(=O)(=O)N1CC=C(c2cc(F)c3c(c2)CC(C2CCN(Cc4ccccc4)CC2)O3)CC1] | 499 |
| 48 | 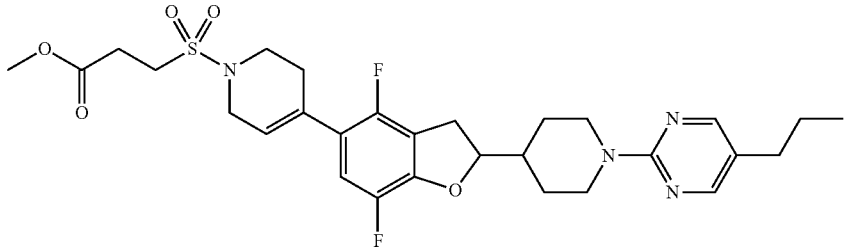 [SMILES: CCCc1cnc(N2CCC(C3Cc4c(F)c(C5=CCN(S(=O)(=O)CCC(=O)OC)CC5)cc(F)c4O3)CC2)nc1] | 591 |
| 49 | 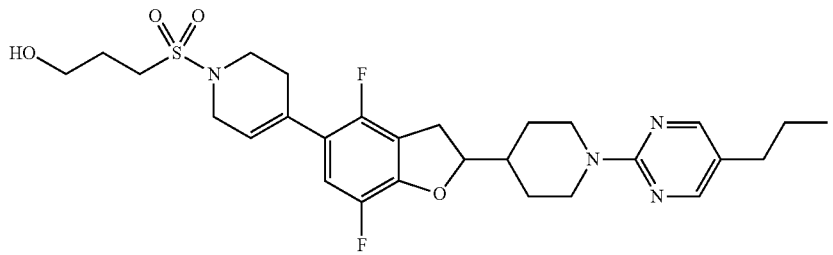 [SMILES: CCCc1cnc(N2CCC(C3Cc4c(F)c(C5=CCN(S(=O)(=O)CCCO)CC5)cc(F)c4O3)CC2)nc1] | 563 |
| 50 | 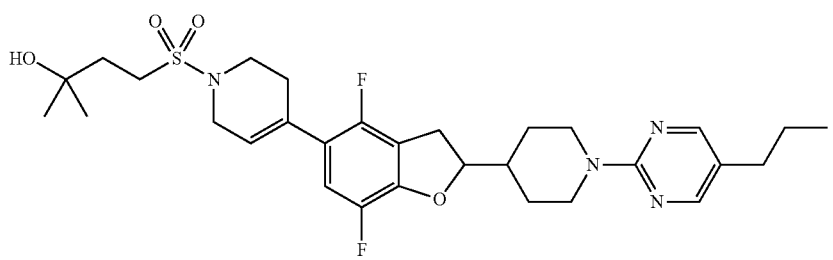 [SMILES: CCCc1cnc(N2CCC(C3Cc4c(F)c(C5=CCN(S(=O)(=O)CCC(C)(C)O)CC5)cc(F)c4O3)CC2)nc1] | 591 |

Assay(s) for GPR119 G Protien-Coupled Receptor Activity

The in vitro modulation of recombinant human GPR119 was determined as follows.

Tet-inducible cAMP Assay

A human-mouse chimeric GPR119 expression construct encoding 3 copies of the FLAG epitope tag, the first 198 amino acids of human GPR119 and the C-terminal 137 amino acids of the mouse receptor was cloned into a tetracycline inducible vector pcDNA5/FRT/TO (Invitrogen #V6520-20), which includes a hygromycin-resistance marker. Tightly controlled receptor expression was achieved by stable integration of this construct into the genome of a specific host cell line, Flp-In-T-Rex-HEK293, expressing the tetracycline repressor (Invitrogen). Once a stable hygromycin-resistant cell line was generated, the cells were maintained at 37° C. in a humidified 5% $CO_2$ atmosphere in culture medium consisting of Dulbecco's modified Eagle's medium (DMEM; Invitrogen #11960) supplemented with 2 mM L-glutamine, 10% fetal bovine serum, 200 μg/ml hygromycin B, and 15 μg/ml blasticidin.

Forty-eight hours prior to the cAMP accumulation assay, cells stably expressing the chimeric human/mouse GPR119 construct were seeded at a density of $4 \times 10^3$ cells/well in 384 well poly-D-lysine coated solid white plates (BD #35-6661) and grown at 37° C. in a humidified 5% $CO_2$ atmosphere in culture medium supplemented with 1 μg/ml tetracycline to induce expression of the receptor. On the day of the assay, medium was removed and cells were incubated for 50 min. at 37° C. in a humidified 5% $CO_2$ atmosphere in 20 μl/well of assay buffer (phosphate-buffered saline with $Ca^{2+}$ and $Mg^{2+}$, 12 mM glucose, 0.1 mM isobutyl-methyl-xanthine, 0.1% fatty-acid free bovine serum albumin) with the desired concentration of compound added from a concentrated stock dissolved in dimethyl sulfoxide (DMSO) to give a final concentration of 1% DMSO in the assay. cAMP accumulation was measured using the CisBio homogeneous time resolved fluorescence (HTRF) assay kit (#62AM2PEC) following the manufacturer's protocol. Briefly, 10 μl each of the cAMP-HTRF fluorescence detection reagents were added to each well, and the samples were incubated for 40 min. at room temperature. Fluorescence was excited at 320 nm and measured at 665 and 620 nm using the Envision instrument (Perkin Elmer), the fluorescence ratio of 665/620 was calculated and converted to nanomolar concentrations of cAMP in each well by interpolation from a cAMP standard curve. The concentration-response curves and $EC_{50}$ values were calculated with a four parameter logistic curve fit equation utilizing Excel/XLfit software (Microsoft and IDBS). The $EC_{50}$ value was calculated as the concentration of agonist which increased the cAMP concentration to a value halfway between the baseline and the maximum.

Compounds of the present invention were tested in the Tet-inducible cAMP assay described immediately above and the results shown in Table 2 below were obtained.

TABLE 2

| Compound | GPR119 $EC_{50}$ (nM) |
|---|---|
| Example 4 | 167.9 |
| Example 5 | 61.8 |
| Example 9 | 1061 |
| Example 11 | 8.9 |
| Example 21 | 2432 |
| Example 39 | 3.1 |
| Example 40 | 3.4 |
| Example 41 | 82.7 |
| Example 44 | 9.7 |

Utilities and Combinations

A. Utilities

The compounds of the present invention possess activity as agonists of the GPR119 receptor, and, therefore, may be used in the treatment of diseases associated with GPR119 receptor activity. Via the activation of GPR119 receptor, the compounds of the present invention may preferably be employed to increase insulin production or increase GLP-1 secretion or both.

Accordingly, the compounds of the present invention can be administered to mammals, preferably humans, for the treatment of a variety of conditions and disorders, including, but not limited to, treating, preventing, or slowing the progression of diabetes and related conditions, microvascular complications associated with diabetes, macrovascular complications associated with diabetes, cardiovascular diseases, Metabolic Syndrome and its component conditions, inflammatory diseases and other maladies. Consequently, it is believed that the compounds of the present invention may be used in preventing, inhibiting, or treating diabetes, hyperglycemia, impaired glucose tolerance, insulin resistance, hyperinsulinemia, retinopathy, neuropathy, nephropathy, wound healing, atherosclerosis and its sequelae (acute coronary syndrome, myocardial infarction, angina pectoris, peripheral vascular disease, intermittent claudication, myocardial ischemia, stroke, heart failure), Metabolic Syndrome, hypertension, obesity, dyslipidemia, hyperlipidemia, hypertriglyceridemia, hypercholesterolemia, low HDL, high LDL, vascular restenosis, peripheral arterial disease, lipid disorders, bone disease (including osteoporosis), PCOS, HIV protease associated lipodystrophy, and glaucoma, and treatment of side-effects related to diabetes, lipodystrophy and osteoporosis from corticosteroid treatment.

Metabolic Syndrome or "Syndrome X" is described in Ford et al., *J. Am. Med. Assoc.*, 287:356-359 (2002) and Arbeeny et al., *Curr. Med. Chem.—Imm., Endoc. & Metab. Agents,* 1:1-24 (2001).

B. Combinations

The present invention includes within its scope pharmaceutical compositions comprising, as an active ingredient, a therapeutically effective amount of at least one of the compounds of Formula I, Ia, or Ib, alone or in combination with a pharmaceutical carrier or diluent. Optionally, compounds of the present invention can be used alone, in combination with other compounds of the invention, or in combination with one or more other therapeutic agent(s), e.g., an antidiabetic agent or other pharmaceutically active material.

The compounds of the present invention may be employed in combination with one or more other suitable therapeutic agents useful in the treatment of the aforementioned disorders including: anti-diabetic agents, anti-hyperglycemic agents, anti-hyperinsulinemic agents, anti-retinopathic agents, anti-neuropathic agents, anti-nephropathic agents, anti-atherosclerotic agents, anti-ischemic agents, anti-hypertensive agents, anti-obesity agents, anti-dyslipidemic agents, anti-dyslipidemic agents, anti-hyperlipidemic agents, anti-hypertriglyceridemic agents, anti-hypercholesterolemic agents, anti-restenotic agents, anti-pancreatic agents, lipid lowering agents, appetite suppressants, treatments for heart failure, treatments for peripheral arterial disease and anti-inflammatory agents.

Examples of suitable anti-diabetic agents for use in combination with the compounds of the present invention include insulin and insulin analogs (e.g., LysPro insulin, inhaled formulations comprising insulin); glucagon-like peptides; sulfonylureas and analogs (e.g., chlorpropamide, glibenclamide, tolbutamide, tolazamide, acetohexamide, glypizide, glyburide, glimepiride, repaglinide, meglitinide); biguanides (e.g., metformin, phenformin, buformin); alpha2-antagonists and imidazolines (e.g., midaglizole, isaglidole, deriglidole, idazoxan, efaroxan, fluparoxan); other insulin secretagogues (e.g., linogliride, insulinotropin, exendin-4, N,N-dimethyl-N'-[2-(4-morpholinyl)phenyl]guanidine (E)-2-butenedioate salt (BTS-675820), (−)-N-(trans-4-isopropylcyclohexanecarbonyl)-D-phenylalanine (A-4166)); thiazolidinediones and PPAR-gamma agonists (e.g., ciglitazone, pioglitazone, troglitazone, rosiglitazone); PPAR-alpha agonists e.g., fenofibrate, gemfibrozil); PPAR alpha/gamma dual agonists (e.g., muraglitazar, peliglitazar, aleglitazar); SGLT2 inhibitors (e.g., 3-(benzo[b]furan-5-yl)-2',6'-dihydroxy-4'-methylpropiophenone-2'-O-(6-O-methoxycarbonyl)-β-d-glucopyranoside (T-1095 Tanabe Seiyaku), phlorizin, TS-033 (Taisho), dapagliflozin (BMS), sergiflozin (Kissei), AVE 2268 (Sanofi-Aventis)), canagliflozin; 11-beta-hydroxysteriod dehydrogenase type I inhibitors (e.g., AMG221, INCB13739); dipeptidyl peptidase-IV (DPP4) inhibitors (e.g., saxagliptin, sitagliptin, vildagliptin, alogliptin and denagliptin); glucagon-like peptide-1 (GLP-1) receptor agonists (e.g., Exenatide (Byetta), NN2211 (Liraglutide, Novo Nordisk), AVE0010 (Sanofi-Aventis), R1583 (Roche/Ipsen), SUN E7001 (Daiichi/Santory), GSK-716155 (GSK/Human Genome Sciences) and Exendin-4 (PC-DACTM); aldose reductase inhibitors (e.g., those disclosed in WO 99/26659); R×R agonists (e.g., reglitazar (JTT-501), 5-[[6-[(2-fluorophenyl)methoxy]-2-naphthalenyl]methyl]-2,4-thiazolidinedione (MCC-555), 5-[[3-(5,6,7,8-tetrahydro-3,5,5,8,8-pentamethyl-2-naphthalenyl)-4-(trifluoromethoxy)-phenyl]methylene]-2,4-thiazolidinedione (MX-6054), DRF2593, farglitazar, (±)-5-[(2,4-dioxothiazolidin-5-yl)methyl]-2-methoxy-N-[[(4-trifluoromethyl)phenyl]-methyl]benzamide (KRP-297), 6-[1-(5,6,7,8-tetrahydro-3,5,5,8,8-pentamethyl-2-naphthalenyl)cyclopropyl]-3-pyridinecarboxylic acid (LG100268)); fatty acid oxidation inhibitors (e.g., clomoxir, etomoxir; α-glucosidase inhibitors: precose, acarbose, miglitol, emiglitate, voglibose, 2,6-dideoxy-2,6-imino-7-O-β-D-glucopyranosyl-D-glycero-L-gulo-heptitol (MDL-25,637), camiglibose); beta-agonists (e.g., methyl ester [4-[(2R)-2-[[(2R)-2-(3-chlorophenyl)-2-hydroxyethyl]amino]propyl]phenoxy]-acetic acid (BRL 35135), 2-[4-[(2S)-2-[[(2S)-2-(3-chlorophenyl)-2-hydroxyethyl]amino]propyl]phenoxy]-acetic acid (BRL 37344), 4-[(3R)-3-[bis[(2R)-2-hydroxy-2-phenylethyl]amino]butyl]-benzamide (Ro 16-8714), 2-[4-[2-[[(2S)-2-hydroxy-3-phenoxypropyl]amino]ethoxy]phenoxy]-N-(2-methoxyethyl)-acetamide (ICI D7114), 5-[(2R)-2-[[(2R)-2-(3-chlorophenyl)-2-hydroxyethyl]amino]propyl]-3-benzodioxole-2,2-dicarboxylic acid, disodium salt (CL 316,243), TAK-667, AZ40140); phosphodiesterase inhibitors, both cAMP and cGMP type (e.g., sildenafil, 9-((1S,2R)-2-fluoro-1-methylpropyl)-2-methoxy-6-(1-piperazinyl)purine hydrochloride (L-686398), L-386,398); amylin agonists (e.g., pramlintide); lipoxygenase inhibitors (e.g., masoprocal); somatostatin analogs (e.g., lanreotide, seglitide, octreotide); glucagon antagonists (e.g., BAY 276-9955); insulin signaling agonists, insulin mimetics, PTP1B inhibitors (e.g., 2-[2-(1,1-dimethyl-2-propenyl)-1H-indol-3-yl]-3,6-dihydroxy-5-[7-(3-methyl-2-butenyl)-1H-indol-3-yl]-2,5-cyclohexadiene-1,4-dione (L-783281), TER17411, TER17529); gluconeogenesis inhibitors (e.g., GP3034); somatostatin analogs and antagonists; antilipolytic agents (e.g., nicotinic acid, acipimox, N-cyclohexyl-2'-O-methyl-adenosine (WAG 994)); glucose transport stimulating agents (e.g., 4-chloro-α-[(4-methylphenyl)sulfonyl]-benzeneheptanoic acid (BM-130795)); glucose synthase kinase inhibitors (e.g., lithium chloride, CT98014, CT98023); galanin receptor agonists; Chemokine receptor antagonist CCR2/5 (e.g., NCB3284, MK-0812, INCB8696, maraviroc (Pfizer) and vicriviroc); thyroid receptor agonists (e.g., KB-2115 (KaroBio)); glucokinase activators (e.g., RO-27-4375, RO-28-1675 (Roche), 6-[[3-[(1S)-2-methoxy-1-methylethoxy]-5-[(1S)-1-methyl-2-phenylethoxy]benzoyl]amino]-3-pyridinecarboxylic acid (GKA-50 AstraZeneca)); GPR40 modulators(e.g., (S)-4-(dimethylamino)-3-(4-((4-methyl-2-p-tolylthiazol-5-yl)methoxy)phenyl)-4-oxobutanoic acid, 6-chloro-2-(4-chlorobenzylthio)-1-(4-(methoxymethoxy)phenyl)-1H-benzo[d]imidazole, TAK-875, CNX011, and P1736).

Examples of suitable lipid lowering agents and anti-atherosclerotic agents for use in combination with the compounds of the present invention include one or more MTP/ApoB secretion inhibitors (e.g., dirlopatide, N-(2,2,2-trifluoroethyl)-9-[4-[4-[[[4'-(trifluoromethyl)[1,1'-biphenyl]-2-yl]carbonyl-]amino]-1-piperidinyl]butyl]-9H-fluorene-9-carboxamide, methanesulfonate, CP-741952 (Pfizer), SLx-4090 (Surface Logix)); HMG CoA reductase inhibitors (e.g., atorvastatin, rosuvastatin, simvastatin, pravastatin, lovastatin, fluvastatin); squalene synthetase inhibitors, PPAR alpha agonists and fibric acid derivatives (e.g., fenofibrate, gemfibrozil); ACAT inhibitors; lipoxygenase inhibitors; cholesterol absorption inhibitors (e.g., ezetimibe); thyroid receptor agonists (e.g., as set forth above); Ileal Na+/bile acid cotransporter inhibitors (e.g., compounds as disclosed in Drugs of the Future, 24:425-430 (1999); upregulators of LDL receptor activity (e.g., (3R)-3-[(13R)-13-hydroxy-10-oxotetradecyl]-5,7-dimethoxy-1(3H)-isobenzofuranone (Taisho Pharmaceutical Co. Ltd.) and (3α,4α,5α)-4-(2-propenyl)-cholestan-3-ol (Eli Lilly); bile acid sequestrants (e.g., WELCHOL®, COLESTID®, LoCholest and QUESTRAN®; and fibric acid derivatives, such as Atromid, LOPID® and Tricot); cholesterol ester transfer protein inhibitors (e.g., torcetrapib and (2R)-3-{[3-(4-chloro-3-ethyl-phenoxy)-phenyl]-[[3-(1,1,2,2-tetrafluoroethoxy)phenyl]methyl]amino}-1,1,1-trifluoro-2-propanol); nicotinic acid and derivatives thereof (e.g., niacin, acipimox); PCSK9 inhibitors; L×R agonists (e.g., those disclosed in U.S. Patent Application Publication Nos. 2003/01814206, 2005/0080111, and 2005/0245515); lipoxygenase inhibitors (e.g., such as benzimidazole derivatives, as disclosed in WO 97/12615, 15-LO inhibitors, as disclosed in WO 97/12613, isothiazolones, as disclosed in WO 96/38144, and 15-LO inhibitors, as disclosed by Sendobry et al., "Attenuation of diet-induced atherosclerosis in rabbits with a highly selective 15-lipoxygenase inhibitor lacking significant antioxidant properties", Brit. J. Pharmacology, 120:1199-1206 (1997), and Cornicelli et al., "15-Lipoxygenase and its Inhibition: A Novel Therapeutic Target for Vascular Disease", Current Pharmaceutical Design, 5:11-20 (1999)).

Preferred hypolipidemic agents are pravastatin, lovastatin, simvastatin, atorvastatin, fluvastatin, cerivastatin, atavastatin, and rosuvastatin.

Examples of suitable anti-hypertensive agents for use in combination with the compounds of the present invention include beta adrenergic blockers, calcium channel blockers (L-type and T-type; e.g., diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors (e.g., aliskiren), ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan, and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopeptidase inhibitors (dual NEP-ACE inhibitors) (e.g., omapatrilat and gemopatrilat), nitrates, central alpha agonists (e.g., clonidine), alpha1 blockers (e.g., prazosine), arterial vasodilators (e.g., minoxidil), sympatolytics (e.g., resperine), renin inhibitors (e.g., Aliskiren (Novartis)).

Examples of suitable anti-obesity agents for use in combination with the compounds of the present invention include a cannabinoid receptor 1 antagonist or inverse agonist (e.g., rimonabant, (4S)-3-(4-chlorophenyl)-N-[(4-chlorophenyl)sulfonyl]-4,5-dihydro-N'-methyl-4-phenyl-1H-pyrazole-1-carboximidamide (SLV 319), CP-945598 (Pfizer), Surinabant (SR-147778, Sanofi-Aventis), N-[(1S,2S)-3-(4-chlorophenyl)-2-(3-cyanophenyl)-1-methylpropyl]-2-methyl-2-{[5-(trifluoromethyl)pyridin-2-yl]oxy}propanamide (Merck) and those discussed in Hertzog, D. L., Expert Opin. Ther. Patents, 14:1435-1452 (2004)); a beta 3 adrenergic agonist (e.g., rafabegron (AJ9677, Takeda/Dainippon), N-[4-[2-[[(2S)-3-[(6-amino-3-pyridinyl)oxy]-2-hydroxypropyl]amino]ethyl]phenyl]-4-(1-methylethyl)-benzenesulfonamide (L750355, Merck), or CP331648 (Pfizer) or other known beta 3 agonists, as disclosed in U.S. Pat. Nos. 5,541,204, 5,770,615, 5,491,134, 5,776,983, and 5,488,064, with rafabegron, N-[4-[2-[[(2S)-3-[(6-amino-3-pyridinyl)oxy]-2-hydroxypropyl]amino]ethyl]phenyl]-4-(1-methylethyl)-benzenesulfonamide, and CP331648 being preferred); a lipase inhibitor (e.g., orlistat or cetilistat, with orlistat being preferred); a serotonin and norepinephrine reuptake inhibitor (e.g., sibutramine, Abbott and tesofensine, Neurosearch) with sibutramine being preferred; a dopamine reuptake inhibitor (e.g., buproprion, GSK); or 5-HT$_{2C}$ agonist, (e.g., lorcaserin hydrochloride (Arena), WAY-163909 [(7bR,10aR)-1,2,3,4,8,9,10,10a-octahydro-7bH-cyclopenta-[b] [1,4]diazepino[6,7,1hi]indole], with lorcaserin hydrochloride being preferred); 5-HT6 receptor antagonists (Suven, Biovitrum, Epix), anti-epileptics topiramate (Johnson & Johnson) and zonisamide, a ciliary neurotrophic factor agonist (e.g., AXOKINE® (Regeneron)); brain-derived neurotrophic factor (BDNF), orexin antagonists, histamine receptor-3 (H3) modulators, melanin-concentrating hormone receptor (MCHR) antagonists (e.g., GSK-856464 (GlaxoSmithKline), T-0910792 (Amgen)); diacylglycerol acyltransferase (DGAT) inhibitors (e.g., BAY-74-4113 (Bayer), PF-04620110, and LCQ908); acetyl-CoA carboxylase (ACC) inhibitors (e.g., N-(4-(4-(4-isopropoxyphenoxy)phenyl)but-3-yn-2-yl)acetamide (A-80040, Abbott), (R)-anthracen-9-yl(3-(morpholine-4-carbonyl)-1,4'-bipiperidin-1'-yl) methanone (CP-640186, Pfizer)); SCD-1 inhibitors as described by Jiang et al., *Diabetes,* 53 (2004), (abs 653-p); amylin receptor agonists (e.g., compounds disclosed in WO 2005/025504); thyroid receptor agonists (e.g., as set forth above); growth hormone secretagogue receptor (GHSR) antagonists (e.g., A-778193 (Abbott); leptin and leptin mimetics (e.g., OB-3 (Aegis/Albany Medical College); leptin analogs A-100 and A-200 (Amgen), CBT-001452 (Cambridge Biotechnology), ML-22952 (Millennium)), PYY receptor agonist (e.g., AC-162352 (Amylin), PYY-3-36 (Emishere), PYY(3-36)NH2 (Unigene)); NPY-Y4 agonists (7TM Pharma WO 2005/089786(A2,A3)-1), NPY-5 antagonists (e.g., NPYSRA-972 (AstraZeneca), GW-594884A (GlaxoSmithKline), J-104870 (Banyu)); MTP/apoB secretion inhibitors (as set forth above), and/or an anorectic agent.

The anorectic agent which may be optionally employed in combination with compounds of the present invention include dexamphetamine, phentermine, phenylpropanolamine, or mazindol, with dexamphetamine being preferred.

Other compounds that can be used in combination with the compounds of the present invention include CCK receptor agonists (e.g., SR-27895B); galanin receptor antagonists; MCR-4 antagonists (e.g., N-acetyl-L-norleucyl-L-glutaminyl-L-histidyl-D-phenylalanyl-L-arginyl-D-tryptophyl-glycinamide, (HP-228)); urocortin mimetics, CRF antagonists, and CRF binding proteins (e.g., mifepristone (RU-486), urocortin).

Further, the compounds of the present invention may be used in combination with HIV protease inhibitors, including but not limited to REYATAZ® and KALETRA®.

Examples of suitable memory enhancing agents, anti-dementia agents, or cognition promoting agents for use in combination with the compounds of the present invention include, but are not limited to ARICEPT®, razadyne, donepezil, rivastigmine, galantamine, memantine, tacrine, metrifonate, muscarine, xanomelline, deprenyl and physostigmine.

Examples of suitable anti-inflammatory agents for use in combination with the compounds of the present invention include, but are not limited to, NSAIDS, prednisone, acetaminophen, aspirin, codeine, fentanyl, ibuprofen, indomethacin, ketorolac, morphine, naproxen, phenacetin, piroxicam, sufentanyl, sunlindac, interferon alpha, prednisolone, methylprednisolone, dexamethazone, flucatisone, betamethasone, hydrocortisone, beclomethasone, REMICADE®, ORENCIA®, and ENBREL®.

The aforementioned patents and patent applications are incorporated herein by reference.

The above other therapeutic agents, when employed in combination with the compounds of the present invention may be used, for example, in those amounts indicated in the *Physicians' Desk Reference,* as in the patents set out above, or as otherwise determined by one of ordinary skill in the art.

Dosage and Formulation

The compounds of this disclosure can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the disorder.

By way of general guidance, the daily oral dosage of each active ingredient, when used for the indicated effects, will range between about 0.001 to 1000 mg/kg of body weight, or between about 0.01 to 100 mg/kg of body weight per day, or alternatively, between about 1.0 to 20 mg/kg/day. Compounds of this invention may be administered in a single daily dose, or the total daily dosage may be administered in divided doses of two, three, or four times daily. In one embodiment, the daily oral dosage of the active ingredient is between 3 and 600 mg either administered once daily or in divided doses administered twice daily. Alternatively, the active ingredient may be administered in doses of 10-20 mg administered twice daily or 40 to 100 mg administered once daily. Alternatively, the active ingredient may be administered a dose of 12.5 mg twice a day or 75 mg once a day. Alternatively, the active ingredient may be administered in doses of 3, 10, 30, 100, 300, and 600 mg administered either once or twice a day.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration may contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Representative useful pharmaceutical dosage-forms for administration of the compounds of this invention can be illustrated as follows:

Capsules

A large number of unit capsules can be prepared by filling standard two-piece hard gelatin capsules each with 100 milligrams of powdered active ingredient, 150 milligrams of lactose, 50 milligrams of cellulose, and 6 milligrams magnesium stearate.

Soft Gelatin Capsules

A mixture of active ingredient in a digestible oil such as soybean oil, cottonseed oil or olive oil may be prepared and injected by means of a positive displacement pump into gelatin to form soft gelatin capsules containing 100 milligrams of the active ingredient. The capsules should be washed and dried.

Tablets

Tablets may be prepared by conventional procedures so that the dosage unit is 100 milligrams of active ingredient, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

Dispersion

A spray dried dispersion can be prepared for oral administration by methods know to one skilled in the art.

Injectable

A parenteral composition suitable for administration by injection may be prepared by stirring 1.5% by weight of active ingredient in 10% by volume propylene glycol and water. The solution should be made isotonic with sodium chloride and sterilized.

Suspension

An aqueous suspension can be prepared for oral administration so that each 5 mL contain 100 mg of finely divided active ingredient, 200 mg of sodium carboxymethyl cellulose, 5 mg of sodium benzoate, 1.0 g of sorbitol solution, U.S.P., and 0.025 mL of vanillin.

Where two or more of the foregoing second therapeutic agents are administered with the compound of the examples, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of the examples and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material which effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Additionally, certain compounds disclosed herein may be useful as metabolites of other compounds. Therefore, in one embodiment, compounds may be useful either as a substantially pure compound, which may also then be incorporated into a pharmaceutical composition, or may be useful as metabolite which is generated after administration of the prodrug of that compound. In one embodiment, a compound may be useful as a metabolite by being useful for treating disorders as described herein.

What is claimed is:
1. A compound of formula I

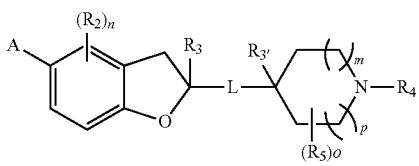

I or an enantiomer, diastereomer, tautomer or salt thereof wherein:

A is

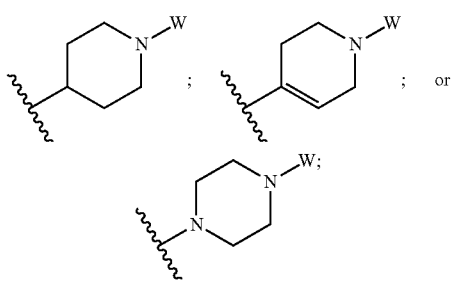

m is 0, 1 or 2;
n is 0-3;
o is 0-4;
p is 0, 1 or 2;
L is a bond, or —$CR_{1a}R_{1a}$—;
W is —$S(=O)_2$—$R_1$, —$S(=O)_2$—$NR_{1a}R_1$, —$C(=O)$—$R_1$, —$C(=O)$—O—$R_1$, —$C(=O)$—$NR_{1a}R_1$ or a 4- to 10-membered heteroaryl, which contains 1-4 heteroatoms selected from N, O, and S and may be optionally substituted with one or more $R_{20}$'s;
$R_1$ is $(C_1-C_6)$-alkyl, $(C_2-C_6)$-alkenyl, $(C_2-C_6)$-alkynyl, $(C_{6-10})$aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{18}$R$_{19}$, —NR$_{18}$R$_{19}$, —O(C=O)—$(C_1-C_6)$-alkyl, —O(C=O)NR$_{18}$R$_{19}$; —$(C_1-C_6)$-alkyl-COOH, —$(C_1-C_6)$-alkylOH, —$(C_1-C_6)$-alkyl(NH$_2$)COOH, —$(C_1-C_6)$-alkylCONR$_{18}$R$_{19}$, —$(C_1-C_6)$-alkyl-CO$_2(C_1-C_6)$-alkyl, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy;

$R_{1a}$, at each occurrence, is independently hydrogen or $(C_1-C_8)$alkyl;

$R_2$, at each occurrence, is independently H, halo, —OH, $(C_1-C_6)$-alkyl, $(C_2-C_6)$-alkenyl, $(C_2-C_6)$-alkynyl, $(C_1-C_6)$-alkyloxy, cyano, —CONR$_{18}$R$_{19}$ or —NR$_{18}$R$_{19}$; wherein any alkyl may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, halo$(C_1-C_6)$alkyl, and halo$(C_1-C_6)$alkyloxy;

$R_3$ is hydrogen or $(C_1-C_6)$-alkyl;
$R_{3'}$ is hydrogen, —OH, halo, or $(C_1-C_6)$-alkyl;
$R_4$ is $(C_1-C_6)$-alkyl, $(C_2-C_6)$-alkenyl, $(C_2-C_6)$-alkynyl, —CO$(C_1-C_6)$-alkyl, —CO$_2(C_1-C_6)$-alkyl, —CO$_2(C_3-C_{12})$-cycloalkyl, —SO$_2(C_1-C_6)$-alkyl, $(C_{6-10})$aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, nitro, —COOH, —CO$(C_1-C_6)$-alkyl, —CO$_2(C_1-C_6)$-alkyl, —CONR$_{18}$R$_{19}$, —NR$_{18}$R$_{19}$, —O(C=O)—$(C_1-C_6)$-alkyl, —O(C=O)NR$_{18}$R$_{19}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{18}$R$_{19}$, —$(C_1-C_6)$-alkyl-CO$_2(C_1-C_6)$-alkyl, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy;

$R_5$, at each occurrence, is independently H, halo, —OH or $(C_1-C_6)$-alkyl;

or two $R_5$'s are taken together with the atom or atoms to which both are attached to form a 3- to 8-membered ring, which may optionally contain 1-4 heteroatoms selected from N, O, and S and be optionally substituted with one or more $R_{20}$'s;

or two $R_5$'s may be taken together with the atoms to which they are attached to form a $(C_1-C_6)$-alkyl bridging group, which may optionally contain 1-4 heteroatoms selected from N, O, and S;

$R_{18}$ and $R_{19}$, at each occurrence, are independently hydrogen or $(C_1-C_8)$alkyl, wherein the alkyl may be optionally substituted with one or more $R_{20}$'s;

or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{28}$R$_{29}$, —NR$_{28}$R$_{29}$, —O(C=O)—$(C_1-C_6)$-alkyl, —O(C=O)NR$_{28}$R$_{29}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2$$(C_1-C_6)$-alkyl, —O—P(=O)(OH)$_2$, —O—CR$_{1a}$R$_{1a}$—P(=O)(OH)$_2$, —P(=O)(OH)$_2$, $(C_{6-10})$aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{28}$R$_{29}$, —NR$_{28}$R$_{29}$, —O(C=O)—$(C_1-C_6)$-alkyl, —O(C=O)NR$_{28}$R$_{29}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{28}$R$_{29}$, —$(C_1-C_6)$-alkyl-CO$_2$$(C_1-C_6)$-alkyl, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy;

$R_{28}$ and $R_{29}$, at each occurrence, are independently hydrogen or $(C_1-C_8)$alkyl;

or $R_{28}$ and $R_{29}$ are taken together with the nitrogen to which both are attached to form a 3- to 8-membered ring, which may optionally contain 1-4 heteroatoms selected from N, O, and S.

2. The compound, enantiomer, diastereomer, tautomer, or salt thereof, of claim 1, wherein the compound is a compound of formula Ia:

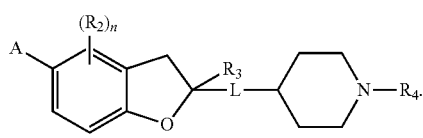

Ia

3. The compound, enantiomer, diastereomer, tautomer, or salt thereof, of claim 1, wherein:

$R_4$ is a 5- to 10-membered heteroaryl, which contains 1-4 heteroatoms selected from N, O, and S; or a 5- to 10-membered heterocyclo, which contains 1-4 heteroatoms selected from N, O, and S; wherein the heteroaryl, and heterocyclo are substituted with one or more substituents selected from the group consisting of: halo, —OH, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, nitro, —COOH, —CO$(C_1-C_6)$-alkyl, —CO$_2(C_1-C_6)$-alkyl, —CONR$_{18}$R$_{19}$, —NR$_{18}$R$_{19}$, —$(C_1-C_6)$-alkyl-COOH, —$(C_1-C_6)$-alkylOH, —$(C_1-C_6)$-alkyl(NH$_2$)COOH, —$(C_1-C_6)$-alkylCONR$_{18}$R$_{19}$, —$(C_1-C_6)$-alkyl-CO$_2(C_1-C_6)$-alkyl, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy.

4. The compound, enantiomer, diastereomer, tautomer, or salt thereof, of claim 1, wherein:

A is

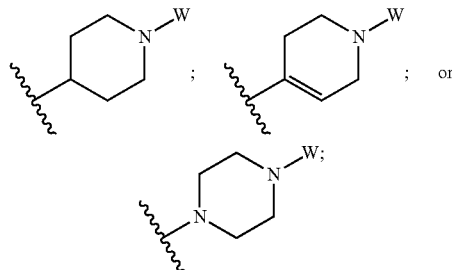

m is 0, 1 or 2;
n is 0-2;
o is 0-3;
p is 0, 1 or 2;
L is a bond, or —CR$_{1a}$R$_{1a}$—;
W is —S(=O)$_2$—R$_1$, —C(=O)—R$_1$, —C(=O)—O—R$_1$, —C(=O)—NR$_{1a}$R$_1$ or a 4- to 10-membered heteroaryl, which contains 1-4 heteroatoms selected from N, O, and S and may be optionally substituted with one or more R$_{20}$'s;

R$_1$ is $(C_1-C_6)$-alkyl, $(C_2-C_6)$-alkenyl, $(C_{6-10})$aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —CONR$_{18}$R$_{19}$, —NR$_{18}$R$_{19}$, —(C=O)—$(C_1-C_6)$-alkyl, —O(C=O)NR$_{18}$R$_{19}$; —$(C_1-C_6)$-alkylCOOH, —$(C_1-C_6)$-alkylOH, —$(C_1-C_6)$-alkyl(NH$_2$)COOH, —$(C_1-C_6)$-alkylCONR$_{18}$R$_{19}$, —$(C_1-C_6)$-alkyl-CO$_2$$(C_1-C_6)$-alkyl, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy;

$R_{1a}$, at each occurrence, is independently hydrogen or $(C_1-C_6)$alkyl;

$R_2$, at each occurrence, is independently H, halo, —OH, $(C_1-C_6)$-alkyl, $(C_2-C_6)$-alkenyl, $(C_2-C_6)$-alkynyl, $(C_1-C_6)$-alkyloxy, cyano, —CONR$_{18}$R$_{19}$ or —NR$_{18}$R$_{19}$; wherein any alkyl may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, halo$(C_1-C_6)$alkyl, and halo$(C_1-C_6)$alkyloxy;

$R_3$ is hydrogen or $(C_1-C_6)$-alkyl;
$R_{3'}$ is hydrogen, —OH or halo;
$R_4$ is $(C_1-C_6)$-alkyl, $(C_2-C_6)$-alkenyl, —CO$(C_1-C_6)$-alkyl, —CO$_2(C_1-C_6)$-alkyl, —CO$_2(C_3-C_{12})$-cycloalkyl, —SO$_2(C_1-C_6)$-alkyl, $(C_{6-10})$aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, nitro, —COOH, —CO($C_1-C_6$)-alkyl, —CO$_2$($C_1-C_6$)-alkyl, —CONR$_{18}$R$_{19}$, —NR$_{18}$R$_{19}$, —($C_1-C_6$)-alkylCOOH, —($C_1-C_6$)-alkylOH, —($C_1-C_6$)-alkyl(NH$_2$)COOH, —($C_1-C_6$)-alkylCONR$_{18}$R$_{19}$, —($C_1-C_6$)-alkyl-CO$_2$($C_1-C_6$)-alkyl, ($C_{6-10}$)aryl, a 5- to 10-membered heteroaryl, which contains 1-4 heteroatoms selected from N, O, and S, a 5- to 10-membered heterocyclo, which contains 1-4 heteroatoms selected from N, O, and S; halo($C_1-C_6$)alkyl, and halo($C_1-C_6$)alkyloxy;

$R_5$, at each occurrence, is independently H, halo, —OH or $(C_1-C_6)$-alkyl;

or two $R_5$'s are taken together with the atom or atoms to which both are attached to form a 3- to 8-membered ring, which may optionally contain 1-4 heteroatoms selected from N, O, and S and be optionally substituted with one or more $R_{20}$'s;

$R_{18}$ and $R_{19}$, at each occurrence, are independently hydrogen or $(C_1-C_8)$alkyl, wherein the alkyl may be optionally substituted with one or more $R_{20}$'s;

or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO($C_1-C_6$)-alkyl, —CO$_2$($C_1-C_6$)-alkyl, —CONR$_{28}$R$_{29}$, —NR$_{28}$R$_{29}$, —($C_1-C_6$)-alkylCOOH, —($C_1-C_6$)-alkylOH, —($C_1-C_6$)-alkyl(NH$_2$)COOH, —($C_1-C_6$)-alkylCONR$_{28}$R$_{29}$, —($C_1-C_6$)-alkyl-CO$_2$($C_1-C_6$)-alkyl, —O—P(=O)(OH)$_2$, —O—CR$_{1a}$R$_{1a}$P(=O)(OH)$_2$, —P(=O)(OH)$_2$, ($C_{6-10}$)aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO($C_1-C_6$)-alkyl, —CO$_2$($C_1-C_6$)-alkyl, —CONR$_{28}$R$_{29}$, —NR$_{28}$R$_{29}$, —O(C=O)—($C_1-C_6$)-alkyl, —O(C=O)NR$_{28}$R$_{29}$; —($C_1-C_6$)-alkylCOOH, —($C_1-C_6$)-alkylOH, —($C_1-C_6$)-alkyl(NH$_2$)COOH, —($C_1-C_6$)-alkylCONR$_{28}$R$_{29}$, —($C_1-C_6$)-alkyl-CO$_2$($C_1-C_6$)-alkyl, ($C_{6-10}$)aryl, a 5- to 10-membered heteroaryl, which contains 1-4 heteroatoms selected from N, O, and S, a 5- to 10-membered heterocyclo, which contains 1-4 heteroatoms selected from N, O, and S; halo($C_1-C_6$)alkyl, and halo($C_1-C_6$)alkyloxy;

$R_{28}$ and $R_{29}$, at each occurrence, are independently hydrogen or $(C_1-C_8)$alkyl;

or $R_{28}$ and $R_{29}$ are taken together with the nitrogen to which both are attached to form a 3- to 8-membered ring, which may optionally contain 1-4 heteroatoms selected from N, O, and S.

5. The compound, enantiomer, diastereomer, tautomer, or salt thereof, of claim 1, wherein:

A is

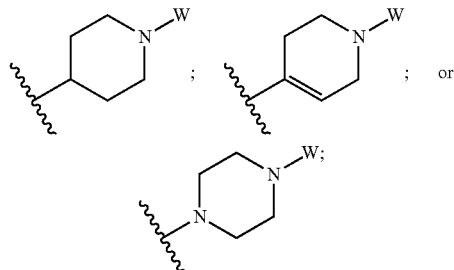

m is 0, 1 or 2;
n is 0-2;
o is 0-2;
p is 0, 1 or 2;
L is a bond, or —CR$_{1a}$R$_{1a}$—;
W is —S(=O)$_2$—R$_1$, —C(=O)—R$_1$, —C(=O)—O—R$_1$, —C(=O)—NR$_{1a}$R$_1$ or a 4- to 10-membered heteroaryl, which contains 1-4 heteroatoms selected from N, O, and S and may be optionally substituted with one or more $R_{20}$'s;
$R_1$ is $(C_1-C_6)$-alkyl, $(C_{6-10})$aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO($C_1-C_6$)-alkyl, —CO$_2$($C_1-C_6$)-alkyl, —CONR$_{18}$R$_{19}$, —NR$_{18}$R$_{19}$, —($C_1-C_6$)-alkylCOOH, —($C_1-C_6$)-alkylOH, —($C_1-C_6$)-alkylCONR$_{18}$R$_{19}$, ($C_{6-10}$)aryl, a 5- to 10-membered heteroaryl, which contains 1-4 heteroatoms selected from N, O, and S, a 5- to 10-membered heterocyclo, which contains 1-4 heteroatoms selected from N, O, and S; halo($C_1-C_6$)alkyl, and halo($C_1-C_6$)alkyloxy;
$R_{1a}$, at each occurrence, is independently hydrogen or $(C_1-C_6)$alkyl;
$R_2$, at each occurrence, is independently H, halo, —OH, $(C_1-C_6)$-alkyl, $(C_2-C_6)$-alkenyl, $(C_2-C_6)$-alkynyl, $(C_1-C_6)$-alkyloxy, cyano, —CONR$_{18}$R$_{19}$ or —NR$_{18}$R$_{19}$; wherein any alkyl may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, halo($C_1-C_6$)alkyl, and halo($C_1-C_6$)alkyloxy;
$R_3$ is hydrogen or $(C_1-C_6)$-alkyl;
$R_{3'}$ is hydrogen, —OH or halo;
$R_4$ is $(C_1-C_6)$-alkyl, —CO($C_1-C_6$)-alkyl, —CO$_2$($C_1-C_6$)-alkyl, —CO$_2$($C_3-C_{12}$)-cycloalkyl, —SO$_2$($C_1-C_6$)-alkyl, ($C_{6-10}$)aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_3-C_{12})$-cycloalkyl, $(C_1-C_6)$-alkyloxy, cyano, nitro, —COOH, —CO($C_1-C_6$)-alkyl, —CO$_2$($C_1-C_6$)-alkyl, —CONR$_{18}$R$_{19}$, —NR$_{18}$R$_{19}$, —(C$_1$-C$_6$)-alkylCOOH, —(C$_1$-C$_6$)-alkylOH, —(C$_1$-C$_6$)-alkylCONR$_{18}$R$_{19}$, (C$_{6-10}$)aryl, a 5- to 10-membered heteroaryl, which contains 1-4 heteroatoms selected from N, O, and S, a 5- to 10-membered heterocyclo, which contains 1-4 heteroatoms selected from N, O, and S; halo(C$_1$-C$_6$)alkyl, and halo(C$_1$-C$_6$)alkyloxy;

R$_5$, at each occurrence, is independently H, halo, —OH or (C$_1$-C$_6$)-alkyl;

or two R$_5$'s are taken together with the atom or atoms to which both are attached to form a 3- to 8-membered ring, which may optionally contain 1-4 heteroatoms selected from N, O, and S and be optionally substituted with one or more R$_{20}$'s;

R$_{18}$ and R$_{19}$, at each occurrence, are independently hydrogen or (C$_1$-C$_8$)alkyl, wherein the alkyl may be optionally substituted with one or more R$_{20}$'s;

or R$_{18}$ and R$_{19}$ are taken together with the nitrogen to which both are attached to form a 3- to 8-membered ring, which may optionally contain 1-4 heteroatoms selected from N, O, and S and be optionally substituted with one or more R$_{20}$'s;

R$_{20}$ is halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —(C$_1$-C$_6$)-alkylCOOH, —(C$_1$-C$_6$)-alkylOH, —(C$_1$-C$_6$)-alkylCONR$_{28}$R$_{29}$, —O—P(=O)(OH)$_2$, —O—CR$_{1a}$R$_{1a}$—P(=O)(OH)$_2$, —P(=O)(OH)$_2$, (C$_{6-10}$)aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{28}$R$_{29}$, —NR$_{28}$R$_{29}$, —O(C=O)—(C$_1$-C$_6$)-alkyl, —O(C=O)NR$_{28}$R$_{29}$; —(C$_1$-C$_6$)-alkylCOOH, —(C$_1$-C$_6$)-alkylOH, —(C$_1$-C$_6$)-alkylCONR$_{28}$R$_{29}$, (C$_{6-10}$)aryl, a 5- to 10-membered heteroaryl, which contains 1-4 heteroatoms selected from N, O, and S, a 5- to 10-membered heterocyclo, which contains 1-4 heteroatoms selected from N, O, and S; halo(C$_1$-C$_6$)alkyl, and halo(C$_1$-C$_6$)alkyloxy;

R$_{28}$ and R$_{29}$, at each occurrence, are independently hydrogen or (C$_1$-C$_8$)alkyl;

or R$_{28}$ and R$_{29}$ are taken together with the nitrogen to which both are attached to form a 3- to 8-membered ring, which may optionally contain 1-4 heteroatoms selected from N, O, and S.

6. The compound, enantiomer, diastereomer, tautomer, or salt thereof, of claim 1, wherein:

A is

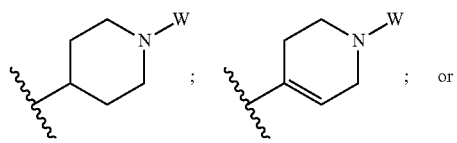

; or

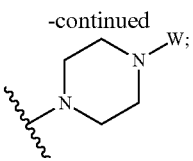

m is 0, 1 or 2;
n is 0-2;
o is 0-1;
p is 0, 1 or 2;
L is a bond, or —CR$_{1a}$R$_{1a}$—;
W is —S(=O)$_2$—R$_1$, —C(=O)—R$_1$, —C(=O)—O—R$_1$, —C(=O)—NR$_{1a}$R$_1$ or a 4- to 10-membered heteroaryl, which contains 1-4 heteroatoms selected from N, O, and S and may be optionally substituted with one or more R$_{20}$'s;

R$_1$ is (C$_1$-C$_6$)-alkyl, (C$_{6-10}$)aryl, or a 5- to 10-membered heteroaryl, which contains 1-4 heteroatoms selected from N, O, and S; wherein any alkyl, aryl and heteroaryl may be optionally substituted with one or more substituents selected from the group consisting of: halo, —OH, (C$_1$-C$_6$)-alkyl, (C$_2$-C$_6$)-alkenyl, (C$_1$-C$_6$)-alkyloxy, cyano, nitro, —COOH, —CO(C$_1$-C$_6$)-alkyl, —CO$_2$(C$_1$-C$_6$)-alkyl, —CONR$_{18}$R$_{19}$, —NR$_{18}$R$_{19}$, —(C$_1$-C$_6$)-alkylCOOH, —(C$_1$-C$_6$)-alkylOH, —(C$_1$-C$_6$)-alkylCONR$_{18}$R$_{19}$, (C$_{6-10}$)aryl, a 5- to 10-membered heteroaryl, which contains 1-4 heteroatoms selected from N, O, and S, a 5- to 10-membered heterocyclo, which contains 1-4 heteroatoms selected from N, O, and S; halo(C$_1$-C$_6$)alkyl, and halo(C$_1$-C$_6$)alkyloxy;

R$_{1a}$, at each occurrence, is independently hydrogen or (C$_1$-C$_5$)alkyl;

R$_2$, at each occurrence, is independently H, halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano or —NR$_{18}$R$_{19}$; wherein any alkyl, may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_1$-C$_6$)-alkyloxy, cyano, nitro, —COOH, —CO(C$_1$-C$_6$)-alkyl, —CO$_2$(C$_1$-C$_6$)-alkyl, —NR$_{18}$R$_{19}$, —(C$_1$-C$_6$)-alkylCOOH, —(C$_1$-C$_6$)-alkylOH, (C$_{6-10}$)aryl, a 5- to 10-membered heteroaryl, which contains 1-4 heteroatoms selected from N, O, and S, a 5- to 10-membered heterocyclo, which contains 1-4 heteroatoms selected from N, O, and S; halo(C$_1$-C$_6$)alkyl, and halo(C$_1$-C$_6$)alkyloxy;

R$_3$ is hydrogen or (C$_1$-C$_6$)-alkyl;
R$_{3'}$ is hydrogen, —OH or halo;
R$_4$ is (C$_1$-C$_6$)-alkyl, —CO$_2$(C$_1$-C$_6$)-alkyl, —CO$_2$(C$_3$-C$_{12}$)-cycloalkyl, —SO$_2$(C$_1$-C$_6$)-alkyl, (C$_{6-10}$)aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, (C$_1$-C$_6$)-alkyl, (C$_2$-C$_6$)-alkenyl, (C$_2$-C$_6$)-alkynyl, (C$_3$-C$_{12}$)-cycloalkyl, (C$_1$-C$_6$)-alkyloxy, cyano, nitro, —COOH, —CO(C$_1$-C$_6$)-alkyl, —CO$_2$(C$_1$-C$_6$)-alkyl, —NR$_{18}$R$_{19}$, —(C$_1$-C$_6$)-alkylCOOH, —(C$_1$-C$_6$)-alkylOH, (C$_{6-10}$)aryl, a 5- to 10-membered heteroaryl, which contains 1-4 heteroatoms selected from N, O, and S, a 5- to 10-membered heterocyclo, which contains 1-4 heteroatoms selected from N, O, and S; halo(C$_1$-C$_6$)alkyl, and halo(C$_1$-C$_6$)alkyloxy;

$R_5$, at each occurrence, is independently H, halo, —OH or $(C_1-C_6)$-alkyl;

$R_{18}$ and $R_{19}$, at each occurrence, are independently hydrogen or $(C_1-C_8)$alkyl, wherein the alkyl may be optionally substituted with one or more $R_{20}$'s;

or $R_{18}$ and $R_{19}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —NR$_{28}$R$_{29}$, —$(C_1-C_6)$-alkylCOOH, —$(C_1-C_6)$-alkylOH, —O—P(=O)(OH)$_2$, —O—CR$_{1a}$R$_{1a}$—P(=O)(OH)$_2$, —P(=O)(OH)$_2$, $(C_{6-10})$aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —NR$_{28}$R$_{29}$, —O(C=O)—$(C_1-C_6)$-alkyl, —$(C_1-C_6)$-alkylCOOH, —$(C_1-C_6)$-alkylOH, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy;

$R_{28}$ and $R_{29}$, at each occurrence, are independently hydrogen or $(C_1-C_8)$alkyl;

or $R_{28}$ and $R_{29}$ are taken together with the nitrogen to which both are attached to form a 3- to 8-membered ring, which may optionally contain 1-4 heteroatoms selected from N, O, and S.

7. The compound, enantiomer, diastereomer, tautomer, or salt thereof, of claim 1, wherein:

A is

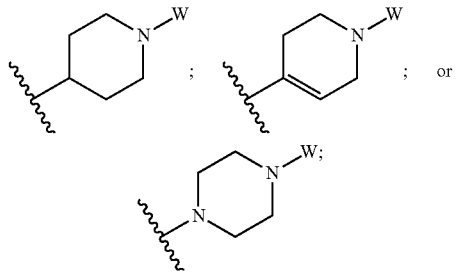

m is 0, 1 or 2;
n is 0-2;
o is 0;
p is 0, 1 or 2;
L is a bond, or —CR$_{1a}$R$_{1a}$—;
W is —S(=O)$_2$—R$_1$, —C(=O)—R$_1$, —C(=O)—O—R$_1$, or —C(=O)—NR$_{1a}$R$_1$;
R$_1$ is $(C_1-C_6)$-alkyl or $(C_{6-10})$aryl; wherein the alkyl and aryl may be optionally substituted with one or more substituents selected from the group consisting of: halo, —OH, $(C_1-C_6)$-alkyl, $(C_2-C_6)$-alkenyl, $(C_1-C_6)$-alkyloxy, cyano, nitro, —COOH, —CO$(C_1-C_6)$-alkyl, —CO$_2(C_1-C_6)$-alkyl, —NR$_{18}$R$_{19}$, —$(C_1-C_6)$-alkyl-COOH, —$(C_1-C_6)$-alkylOH, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy;

$R_{1a}$, at each occurrence, is independently hydrogen or $(C_1-C_4)$alkyl;

$R_2$, at each occurrence, is independently H, halo, —OH, $(C_1-C_6)$-alkyl, $(C_1-C_6)$-alkyloxy, cyano or —NR$_{18}$R$_{19}$; wherein any alkyl may be optionally substituted with one or more substituents selected from the group consisting of: halo, —OH, $(C_1-C_6)$-alkyl, $(C_1-C_6)$-alkyloxy, cyano, nitro, —COOH, —CO$(C_1-C_6)$-alkyl, —CO$_2(C_1-C_6)$-alkyl, —NR$_{18}$R$_{19}$, —$(C_1-C_6)$-alkylCOOH, —$(C_1-C_6)$-alkylOH, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy;

$R_3$ is hydrogen or $(C_1-C_6)$-alkyl;

$R_{3'}$ is hydrogen or halo;

$R_4$ is $(C_1-C_6)$-alkyl, —CO$_2(C_1-C_6)$-alkyl, —CO$_2(C_3-C_{12})$-cycloalkyl, —SO$_2(C_1-C_6)$-alkyl, $(C_{6-10})$aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, $(C_1-C_6)$-alkyl, $(C_3-C_{12})$-cycloalkyl, $(C_1-C_6)$-alkyloxy, cyano, nitro, —COOH, —CO$(C_1-C_6)$-alkyl, —CO$_2(C_1-C_6)$-alkyl, —NR$_{18}$R$_{19}$, —$(C_1-C_6)$-alkylCOOH, —$(C_1-C_6)$-alkylOH, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy;

$R_{18}$ and $R_{19}$, at each occurrence, are independently hydrogen or $(C_1-C_8)$alkyl, wherein the alkyl may be optionally substituted with one or more $R_{20}$'s;

$R_{20}$ is halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —NR$_{28}$R$_{29}$, —$(C_1-C_6)$-alkylCOOH, —$(C_1-C_6)$-alkylOH, $(C_{6-10})$aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, $(C_1-C_6)$-alkyl, $(C_2-C_6)$-alkenyl, $(C_2-C_6)$-alkynyl, $(C_1-C_6)$-alkyloxy, cyano, nitro, —COOH, —CO$(C_1-C_6)$-alkyl, —CO$_2(C_1-C_6)$-alkyl, —NR$_{28}$R$_{29}$, —O(C=O)—$(C_1-C_6)$-alkyl, —$(C_1-C_6)$-alkylCOOH, —$(C_1-C_6)$-alkylOH, $(C_{6-10})$aryl, a 5- to 10-membered heteroaryl, which contains 1-4 heteroatoms selected from N, O, and S, a 5- to 10-membered heterocyclo, which contains 1-4 heteroatoms selected from N, O, and S; halo$(C_1-C_6)$alkyl, and halo$(C_1-C_6)$alkyloxy;

$R_{28}$ and $R_{29}$, at each occurrence, are independently hydrogen or $(C_1-C_8)$alkyl.

8. The compound, enantiomer, diastereomer, tautomer, or salt thereof, of claim 1, wherein:

A is

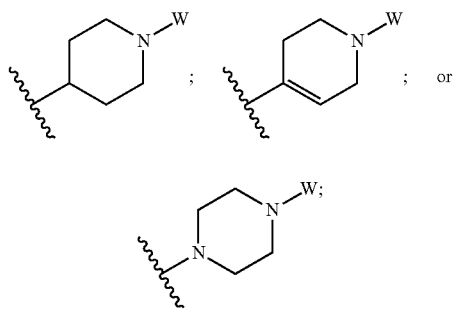

m is 0, 1 or 2;
n is 0-2;
o is 0;
p is 0, 1 or 2;
L is a bond, or —$CR_{1a}R_{1a}$—;
W is —$S(=O)_2$—$R_1$, —$C(=O)$—$R_1$ or —$C(=O)$—$O$—$R_1$;
$R_1$ is ($C_1$-$C_6$)-alkyl; wherein the alkyl may be optionally substituted with one or more substituents selected from the group consisting of: halo, —OH, ($C_1$-$C_6$)-alkyl, ($C_1$-$C_6$)-alkyloxy, cyano, nitro, —CO($C_1$-$C_6$)-alkyl, —$CO_2$($C_1$-$C_6$)-alkyl, —$NR_{18}R_{19}$, —($C_1$-$C_6$)-alkylCOOH, —($C_1$-$C_6$)-alkylOH, ($C_{6-10}$)aryl, a 5- to 10-membered heteroaryl, which contains 1-4 heteroatoms selected from N, O, and S, a 5- to 10-membered heterocyclo, which contains 1-4 heteroatoms selected from N, O, and S; halo($C_1$-$C_6$)alkyl, and halo($C_1$-$C_6$)alkyloxy;
$R_{1a}$, at each occurrence, is independently hydrogen or ($C_1$-$C_4$)alkyl;
$R_2$, at each occurrence, is independently H, halo, —OH, ($C_1$-$C_6$)-alkyl, ($C_1$-$C_6$)-alkyloxy, cyano or —$NR_{18}R_{19}$; wherein any alkyl may be optionally substituted with one or more substituents selected from the group consisting of: halo, —OH, ($C_1$-$C_6$)-alkyl, ($C_1$-$C_6$)-alkyloxy, cyano, nitro, —COOH, —CO($C_1$-$C_6$)-alkyl, —$CO_2$($C_1$-$C_6$)-alkyl, —$NR_{18}R_{19}$, —($C_1$-$C_6$)-alkylCOOH, —($C_1$-$C_6$)-alkylOH, ($C_{6-10}$)aryl, a 5- to 10-membered heteroaryl, which contains 1-4 heteroatoms selected from N, O, and S, a 5- to 10-membered heterocyclo, which contains 1-4 heteroatoms selected from N, O, and S; halo($C_1$-$C_6$)alkyl, and halo($C_1$-$C_6$)alkyloxy;
$R_3$ is hydrogen or ($C_1$-$C_4$)-alkyl;
$R_{3'}$ is hydrogen or halo;
$R_4$ is —$CO_2$($C_1$-$C_6$)-alkyl, —$CO_2$($C_3$-$C_{12}$)-cycloalkyl, —$SO_2$($C_1$-$C_6$)-alkyl, ($C_{6-10}$)aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, ($C_1$-$C_6$)-alkyl, ($C_3$-$C_{12}$)-cycloalkyl, ($C_1$-$C_6$)-alkyloxy, cyano, nitro, —COOH, —CO($C_1$-$C_6$)-alkyl, —$CO_2$($C_1$-$C_6$)-alkyl, —$NR_{18}R_{19}$, —($C_1$-$C_6$)-alkylCOOH, —($C_1$-$C_6$)-alkylOH, ($C_{6-10}$)aryl, a 5- to 10-membered heteroaryl, which contains 1-4 heteroatoms selected from N, O, and S, a 5- to 10-membered heterocyclo, which contains 1-4 heteroatoms selected from N, O, and S; halo($C_1$-$C_6$)alkyl, and halo($C_1$-$C_6$)alkyloxy;

$R_{18}$ and $R_{19}$, at each occurrence, are independently hydrogen or ($C_1$-$C_8$)alkyl, wherein the alkyl may be optionally substituted with one or more $R_{20}$'s;
$R_{20}$ is halo, —OH, ($C_1$-$C_6$)-alkyl, ($C_1$-$C_6$)-alkyloxy, cyano, nitro, —COOH, —CO($C_1$-$C_6$)-alkyl, —$CO_2$($C_1$-$C_6$)-alkyl, —$NR_{28}R_{29}$, —($C_1$-$C_6$)-alkylCOOH, —($C_1$-$C_6$)-alkylOH, ($C_{6-10}$)aryl, a 5- to 10-membered heteroaryl, which contains 1-4 heteroatoms selected from N, O, and S; or a 5- to 10-membered heterocyclo, which contains 1-4 heteroatoms selected from N, O, and S; wherein any alkyl, aryl, heteroaryl, and heterocyclo may be optionally substituted with one or more substituents selected from the group consisting of: halo, —OH, ($C_1$-$C_6$)-alkyl, ($C_1$-$C_6$)-alkyloxy, cyano, nitro, —COOH, —CO($C_1$-$C_6$)-alkyl, —$CO_2$($C_1$-$C_6$)-alkyl, —$NR_{28}R_{29}$, —O(C=O)—($C_1$-$C_6$)-alkyl, —($C_1$-$C_6$)-alkylCOOH, —($C_1$-$C_6$)-alkylOH, ($C_{6-10}$)aryl, a 5- to 10-membered heteroaryl, which contains 1-4 heteroatoms selected from N, O, and S, a 5- to 10-membered heterocyclo, which contains 1-4 heteroatoms selected from N, O, and S; halo($C_1$-$C_6$)alkyl, and halo($C_1$-$C_6$)alkyloxy;
$R_{28}$ and $R_{29}$, at each occurrence, are independently hydrogen or ($C_1$-$C_8$)alkyl.

9. The compound, enantiomer, diastereomer, tautomer, or salt thereof, of claim 1, wherein:

A is

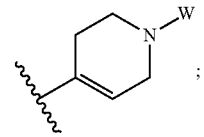

m is 1;
n is 0-2;
o is 0;
p is 1;
L is a bond, or —$CR_{1a}R_{1a}$—;
W is —$S(=O)_2$—$R_1$;
$R_1$ is ($C_1$-$C_6$)-alkyl; wherein the alkyl may be optionally substituted with one or more substituents selected from the group consisting of: F, Cl, —OH, ($C_1$-$C_6$)-alkyl, —$CO_2$($C_1$-$C_6$)-alkyl or phenyl;
$R_{1a}$, at each occurrence, is independently hydrogen or ($C_1$-$C_4$)alkyl;
$R_2$, at each occurrence, is independently H, Cl, F, —OH or ($C_1$-$C_6$)-alkyl;
$R_3$ is hydrogen or ($C_1$-$C_4$)-alkyl;
$R_{3'}$ is hydrogen; and
$R_4$ is —$CO_2$($C_1$-$C_6$)-alkyl, pyridinyl or pyrimidinyl, which is substituted with one or more substituents selected from the group consisting of: halo, —OH, ($C_1$-$C_6$)-alkyl, ($C_3$-$C_{12}$)-cycloalkyl, phenyl, a 5- to 10-membered heteroaryl, which contains 1-4 heteroatoms selected from N, O, and S; halo($C_1$-$C_6$)alkyl, and halo($C_1$-$C_6$)alkyloxy.

10. The compound, enantiomer, diastereomer, tautomer, or salt thereof, of claim 1, wherein the compound is selected from the group consisting of:

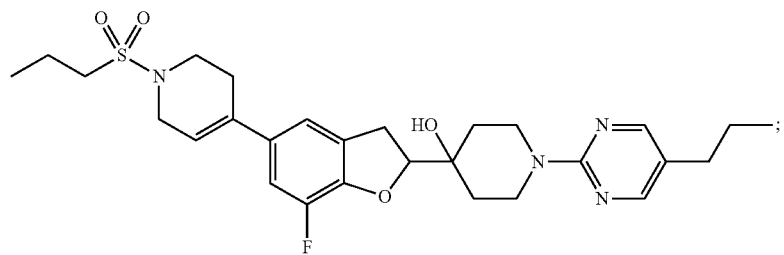
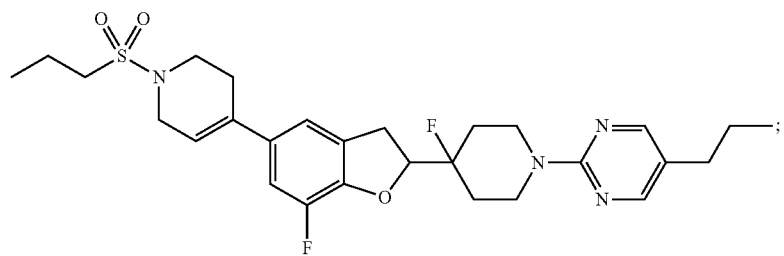
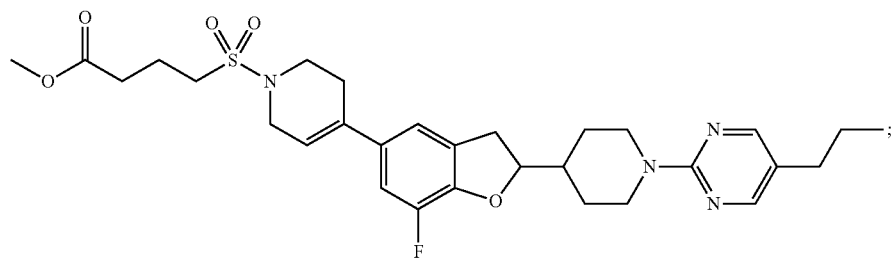
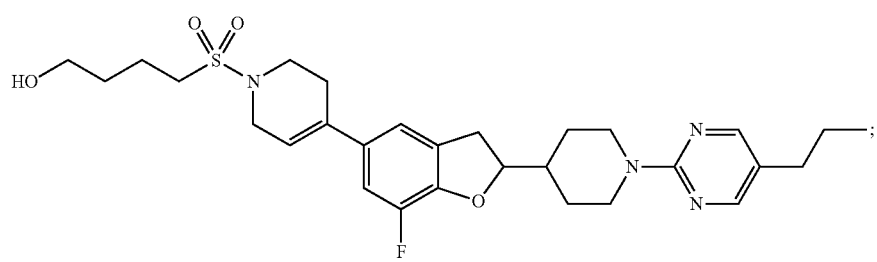
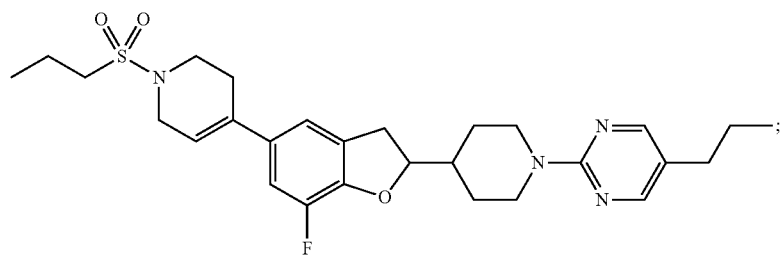
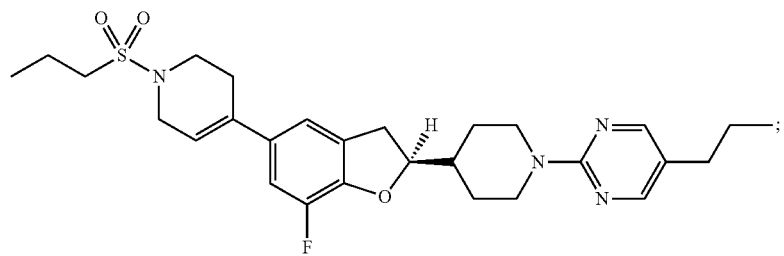

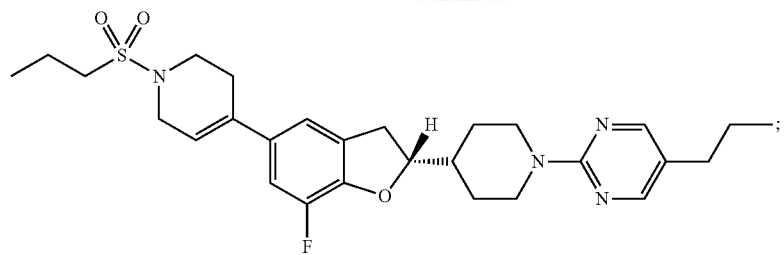
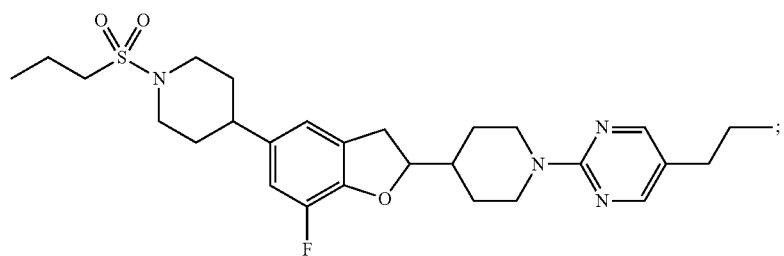
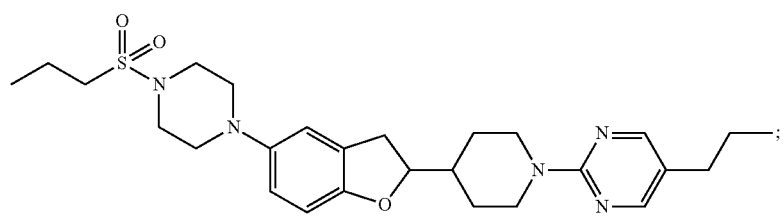
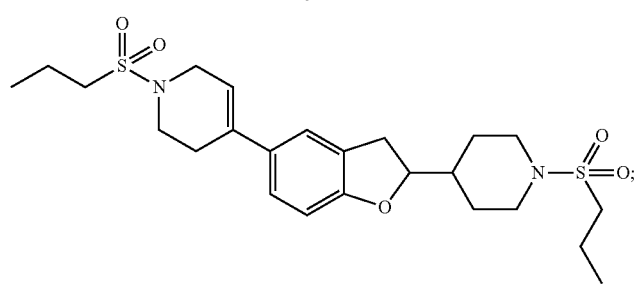
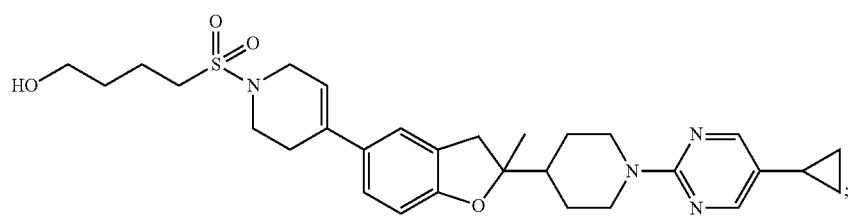
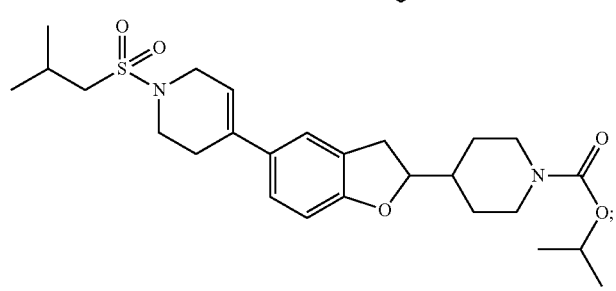
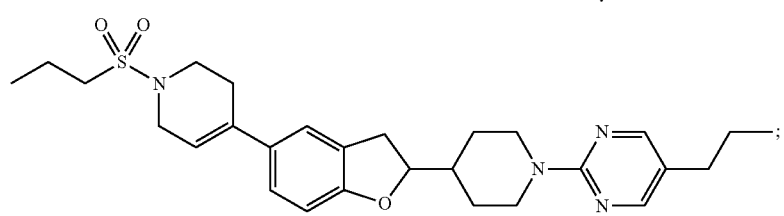

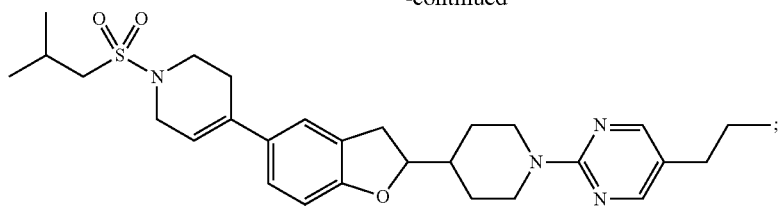
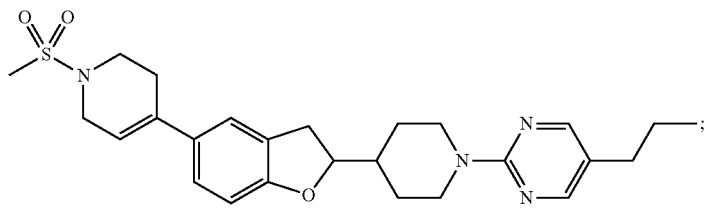
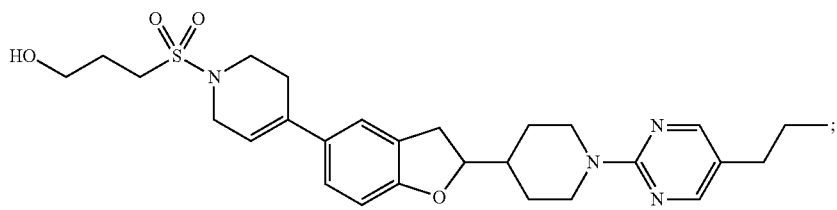
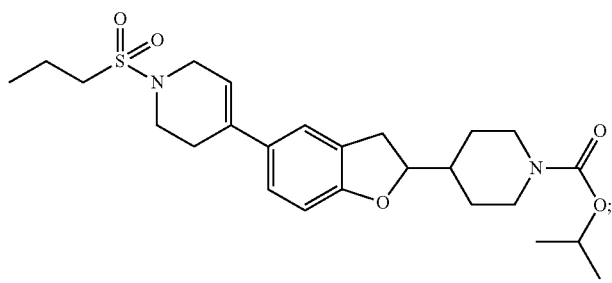
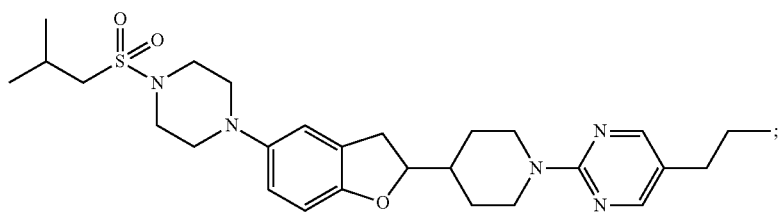
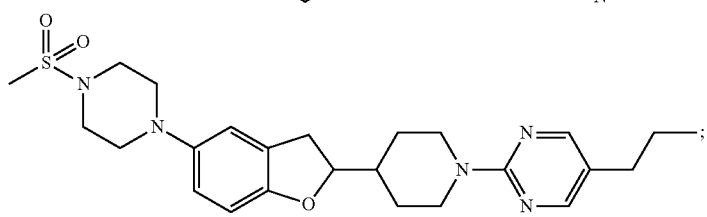
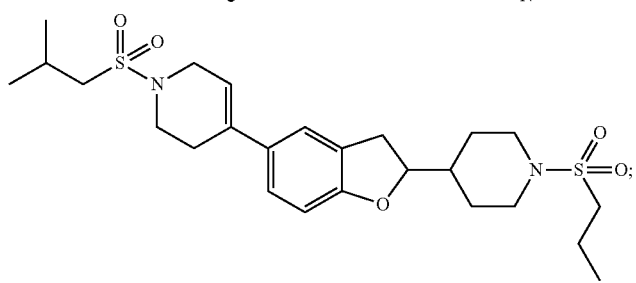

-continued
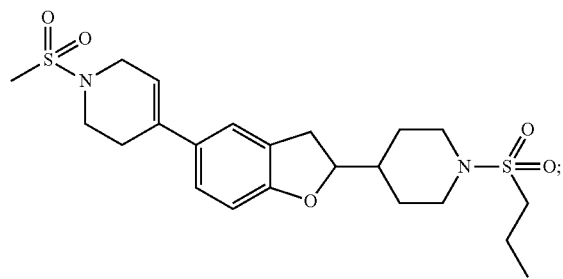
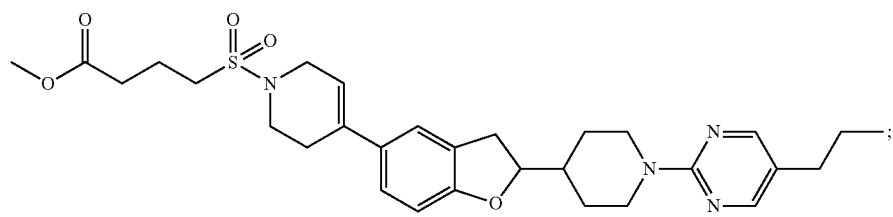
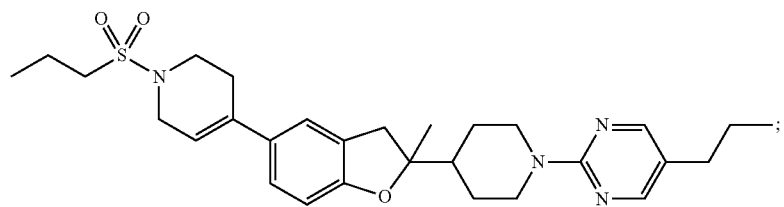
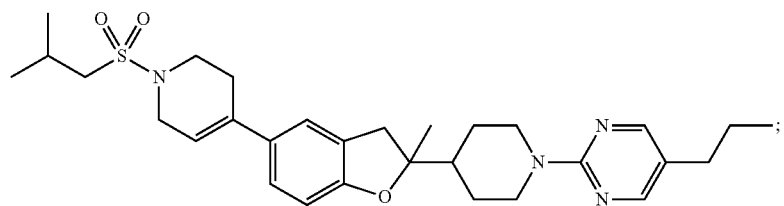
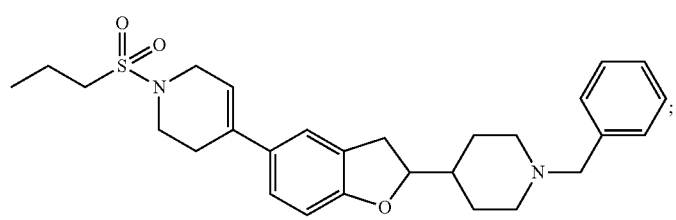
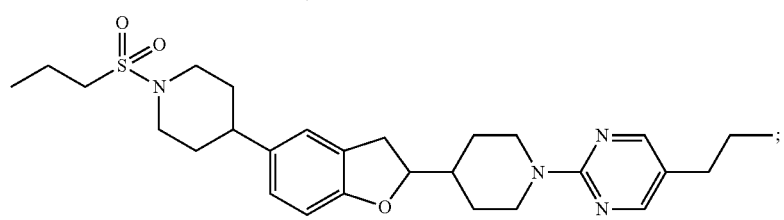
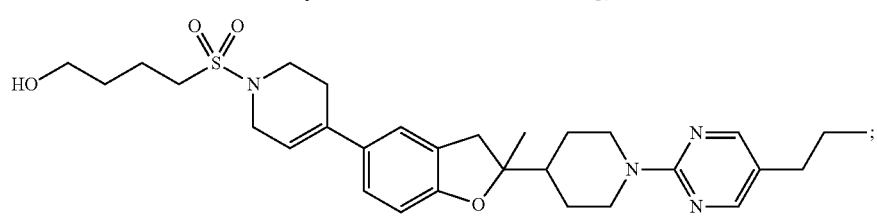

-continued
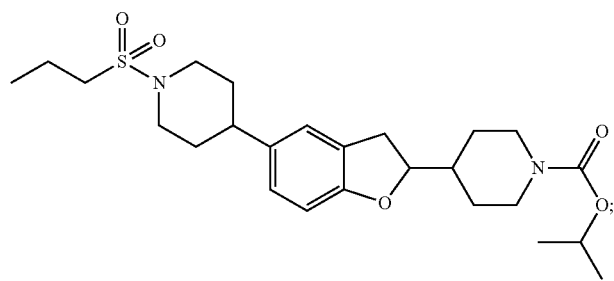
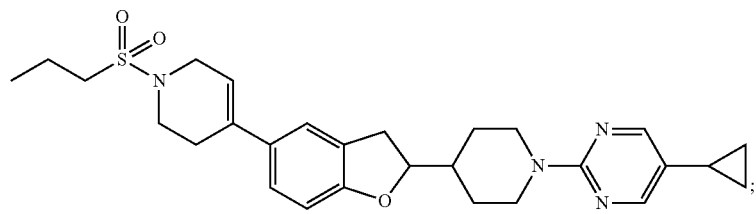
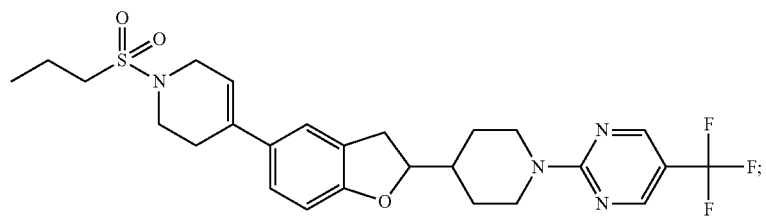
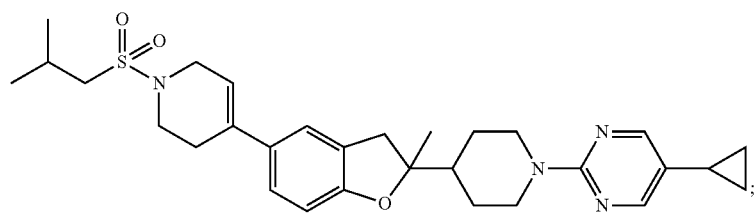
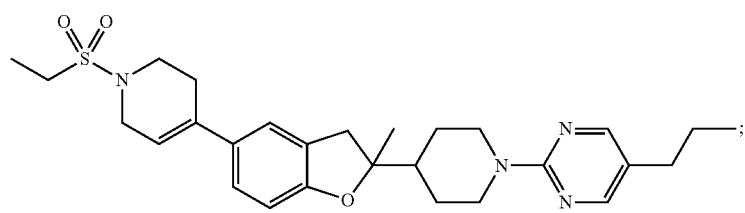
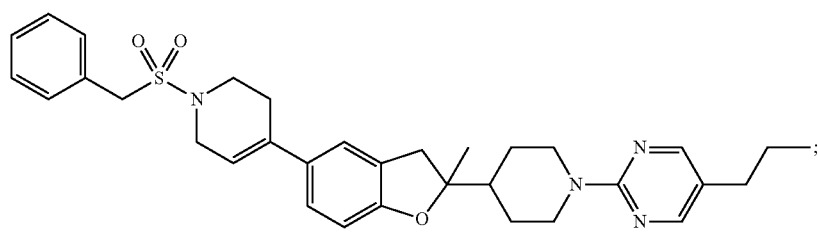
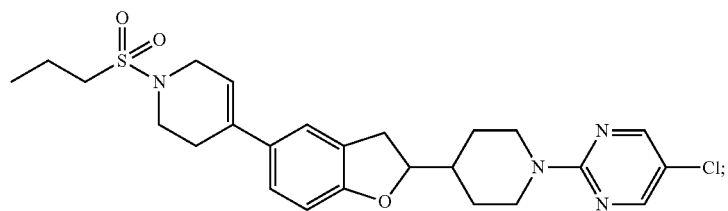

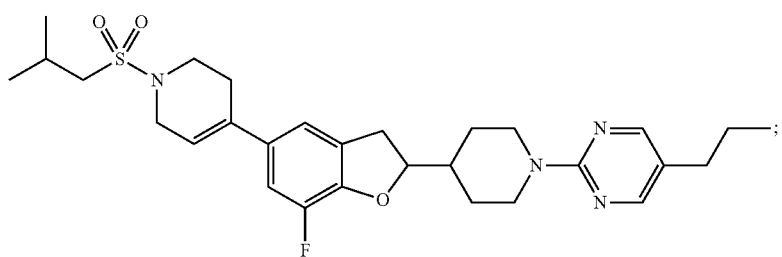
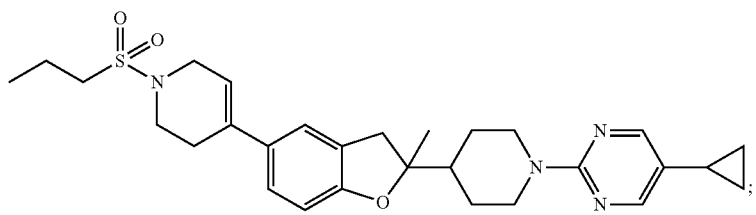
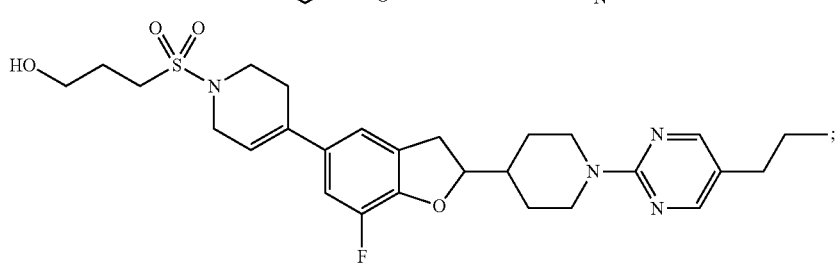
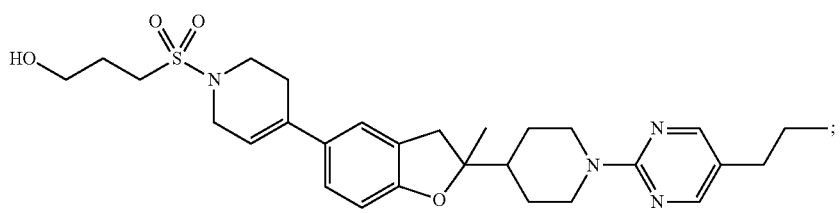
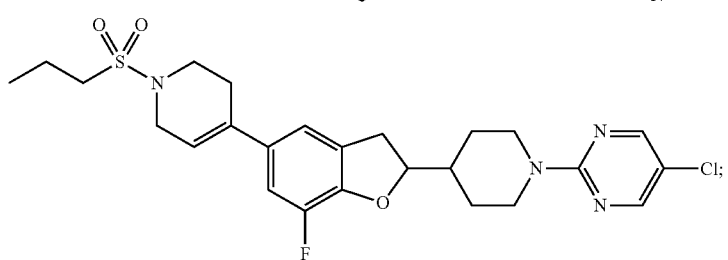
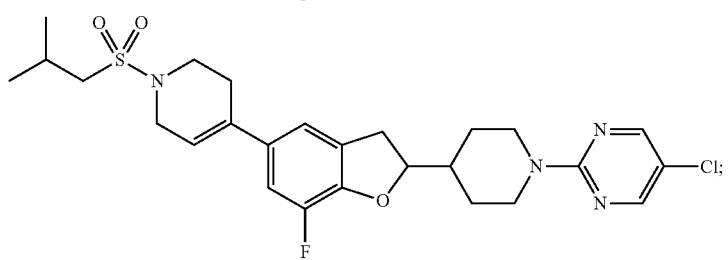
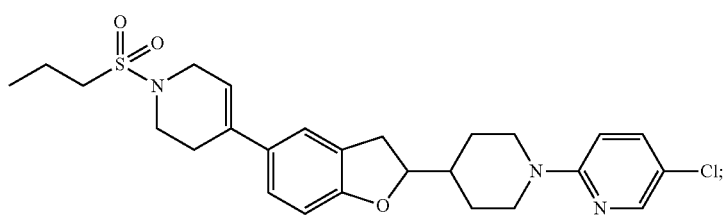

-continued
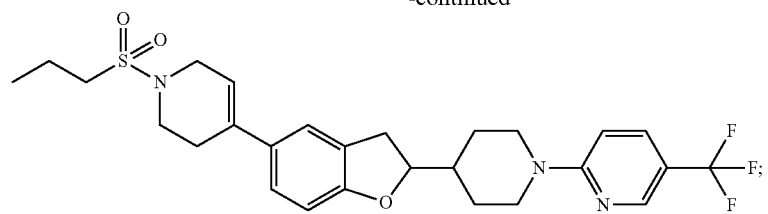
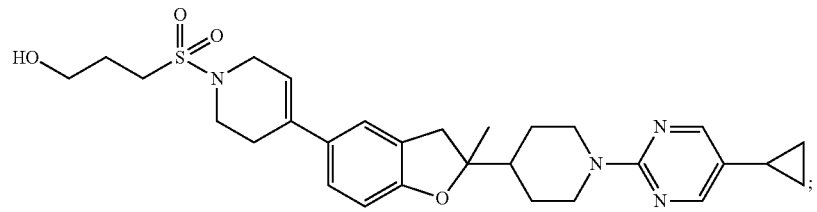
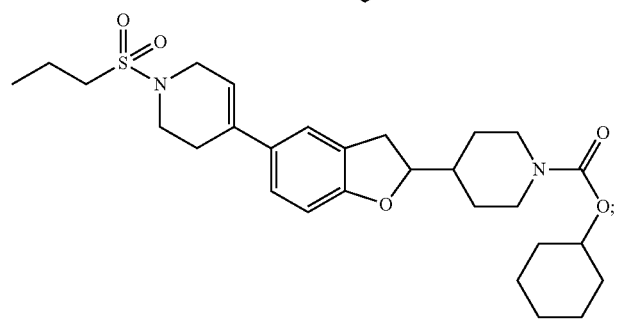
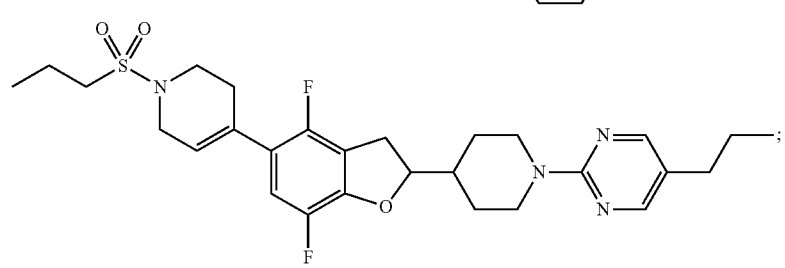
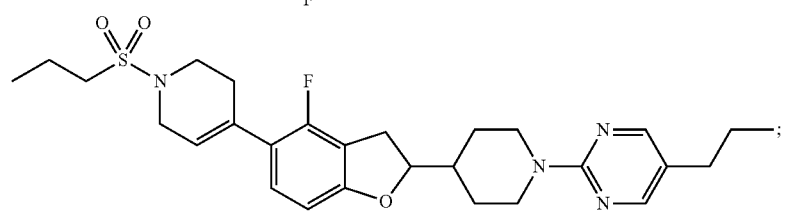
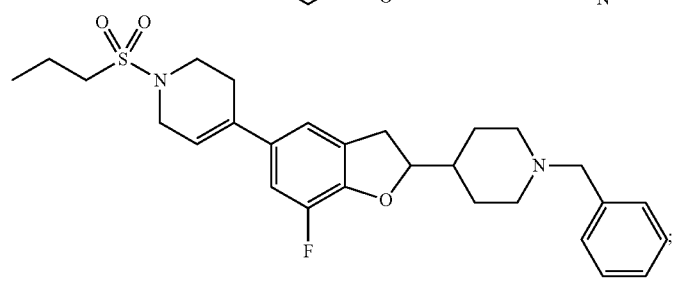
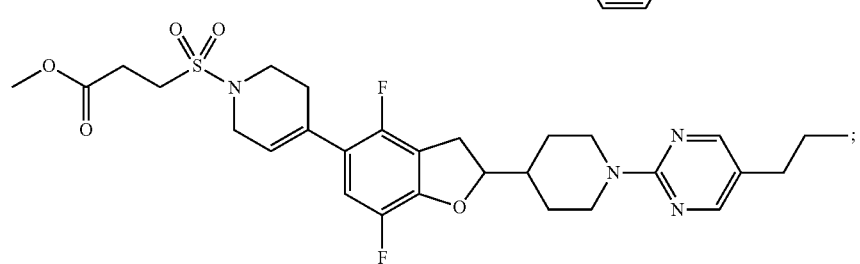

-continued

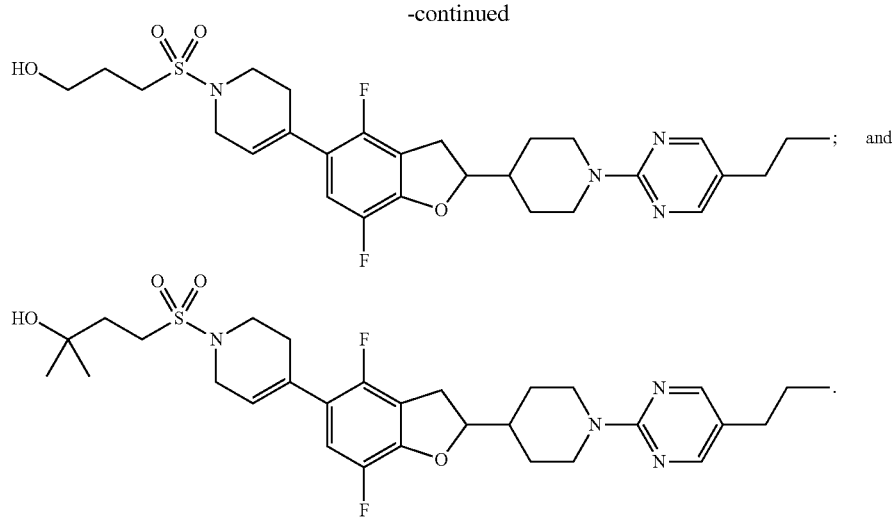

11. A pharmaceutical composition comprised of a therapeutically effective amount of a compound, enantiomer, diastereomer, tautomer or salt thereof, of claim 1, and optionally a pharmaceutically acceptable carrier.

12. The pharmaceutical composition of claim 11, further comprising a therapeutically effective amount of one or more other therapeutically active agents.

13. A pharmaceutical composition comprising a therapeutically effective amount of a compound, enantiomer, diastereomer, tautomer or salt thereof, of claim 1, and a therapeutically effective amount of a dipeptidyl peptidase-IV inhibitor.

14. The pharmaceutical composition of claim 13, wherein the dipeptidyl peptidase-IV inhibitor is selected from saxagliptin, sitagliptin, vildagliptin and alogliptin.

15. The pharmaceutical composition of claim 13, wherein the dipeptidyl peptidase-IV inhibitor is saxagliptin.

* * * * *

UNITED STATES PATENT AND TRADEMARK OFFICE
CERTIFICATE OF CORRECTION

PATENT NO. : 8,729,084 B2  
APPLICATION NO. : 13/696131  
DATED : May 20, 2014  
INVENTOR(S) : Xiang-Yang Ye, Dean A. Wacker and Jeffrey A. Robl Page 1 of 1

It is certified that error appears in the above-identified patent and that said Letters Patent is hereby corrected as shown below:

In the Specification

Column 1  
Line 10, "2010," should read -- 2010. --.

Column 84  
Line 40-41, "—(C=O)—($C_1$-$C_6$)-alkyl," should read -- —O(C=O)—($C_1$-$C_6$)-alkyl, --.

In the Claims

Column 90  
Claim 7, Line 16, "alkyl, –$NR_{18}R_{19}$," should read -- alkyl, —$NR_{18}R_{19}$, --.

Signed and Sealed this  
Fourteenth Day of October, 2014

Michelle K. Lee  
*Deputy Director of the United States Patent and Trademark Office*